US007053104B2

(12) United States Patent
Van Wagenen et al.

(10) Patent No.: US 7,053,104 B2
(45) Date of Patent: May 30, 2006

(54) METABOTROPIC GLUTAMATE RECEPTOR ANTAGONISTS AND THEIR USE FOR TREATING CENTRAL NERVOUS SYSTEM DISEASES

(75) Inventors: Bradford C. Van Wagenen, Salt Lake City, UT (US); Scott T. Moe, Ann Arbor, MI (US); Daryl L. Smith, Fishers, IN (US); Susan M. Sheehan, Dexter, MI (US); Irina Shcherbakova, Salt Lake City, UT (US); Ruth Walton, Bountiful, UT (US); Richard Trovato, Salt Lake City, UT (US); Robert Barmore, Salt Lake City, UT (US); Eric G. Delmar, Salt Lake City, UT (US); Thomas M. Stormann, Salt Lake City, UT (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 122 days.

(21) Appl. No.: 10/211,523

(22) Filed: Aug. 5, 2002

(65) Prior Publication Data

US 2003/0013715 A1   Jan. 16, 2003

Related U.S. Application Data

(60) Division of application No. 09/573,347, filed on May 19, 2000, now Pat. No. 6,429,207, which is a continuation-in-part of application No. PCT/US98/24833, filed on Nov. 20, 1998.

(60) Provisional application No. 60/137,272, filed on Jun. 2, 1999, provisional application No. 60/066,758, filed on Nov. 21, 1997.

(51) Int. Cl.
*A61K 31/47* (2006.01)
*C07D 215/14* (2006.01)

(52) U.S. Cl. .................. 514/311; 546/169; 546/90; 514/291

(58) Field of Classification Search ............ 514/311, 514/291; 546/169, 90
See application file for complete search history.

(56) References Cited

U.S. PATENT DOCUMENTS

| 3,632,581 A | | 1/1972 | Potoski et al. ........ 260/247.5 R |
| 4,450,167 A | * | 5/1984 | Le Martret et al. ......... 514/312 |
| 4,933,342 A | | 6/1990 | Takahashi et al. .......... 514/249 |
| 5,106,976 A | | 4/1992 | Okabe et al. ............... 544/354 |

FOREIGN PATENT DOCUMENTS

| DE | 2 050 074 | 10/1970 |
| DE | 27 28 248 | 6/1977 |
| EP | 0 002 066 | 5/1979 |
| EP | 0 407 192 A2 | 1/1991 |
| EP | 0 694 599 | 1/1996 |
| JP | 7-179371 | 7/1995 |
| WO | 95/09159 | 4/1995 |
| WO | 96/05818 | 2/1996 |
| WO | 96/40641 | 12/1996 |
| WO | 97/02247 | 1/1997 |
| WO | 98/3900 | 9/1998 |
| WO | WO 98/50364 | * 11/1998 ............ 514/311 |
| WO | 01/32632 | 5/2001 |
| WO | 01/32644 | 5/2001 |

OTHER PUBLICATIONS

N.S. Kozlov et al, "Synthesis of adamantane-type beta-amino ketones", XP002101994, abstract & Vestsi Akad. Navuk BSSR, Ser. Khim. Navuk, No. 1, (1991), pp. 60-65.
B. Prager et al. "Beilsteins Handbuch der Organischen Chemie, 9. Bd.", (1926), Verlag Von Julius Springer Berlin, XP002101990, p. 114.
B. Prager et al. "Beilsteins Handbuch der Organischem Chemie, 12. Bd.", (1929) Verlag Von Julius Springer Berlin XP002101991, p. 7.
V. Bruno et al., "Neuroprotective activity of the potent . . . ," Neuropharmacology 38 (1999), pp. 199-207.
A. G. Chapman, "Glutamate and Epilepsy," American Society for Nutritional Sciences, 2000, pp. 1043S-1045S.
A. Palucha et al., "On the role of metabotropic . . . ," Polish Journal of Pharmacology, 2002, 54, pp. 581-586.
G. Battaglia et al., "Endogenous activation of mGlu5 . . . ," The Journal of Neuroscience, Jan. 28, 2004, 24(4), pp. 828-835.
J. Schiefer et al., "The metabotropic glutamate receptor 5 antagonist MPEP . . . ,"Brain Research 1019 (2004), pp. 246-254.
M.O. Urban et al., "Role of metabotropic glutamate receptor subtype 5 . . . ," Neuropharmacology, 44 (2003), pp. 983-993.
C.Z. Zhu et al., "Role of central and peripheral mGluR5 receptors . . . ," Pain, 114 (2005), pp. 195-202.
J. Brodkin et al., "Reduced stress-induced hyperthermia . . . ," European Journal of Neuroscience, vol. 16, 2002, pp. 2241-2244.
M. Pietraszek et al., "mGluR5, but not mGluR1, antagonist . . . ," Neuropharmacology, 49 (2005), pp. 73-85.
M.J. Bradbury et al., "Metabotropic glutamate receptor 5 antagonist—induced . . . ," Neuropharmacology, 44 (2003), pp. 562-572.
P. Gubellini et al., "Induction of corticostriatal LTP . . . ," Neuropharmacology, 46, (2004), pp. 761-769.

(Continued)

*Primary Examiner*—Charanjit S. Aulakh
(74) *Attorney, Agent, or Firm*—Birch, Stewart, Kolasch & Birch, LLP

(57) ABSTRACT

The present invention provides compounds, and pharmaceutical compositions containing those compounds, that are active at metabotropic glutamate receptors. The compounds are useful for treating neurological diseases and disorders. Methods of preparing the compounds also are disclosed.

23 Claims, 14 Drawing Sheets

OTHER PUBLICATIONS

E. Meli et al., "Activation of mGlu1 but not mGlu5 metabotropic . . . ," Pharmacology, Biochemistry and Behavior, 73 (2002), pp. 439-446.

B.G. Lyeth et al., "Group I metabotropic glutamate antagonist . . . ," Experimental Neurology, 169 (2001), pp. 191-199.

R.X. Moldrich et al. "Glutamate metabotropic receptors as targets . . . ," European Journal of Pharmacology, 476 (2003), pp. 3-16.

I.A. Paul et al., "Glutamate and depression . . . ," Analysis New York Academy of Sciences, 1003 (2003), pp. 250-272.

A.G. Chapman et al., "Anticonvulsant activity of two . . . ," Neuropharmacology 39 (2000), pp. 1567-1574.

A.G. Chapman et al., "Anticonvulsant actions of LY 367385 . . . ," European Journal of Pharmacology 368 (1999), pp. 17-24.

* cited by examiner

FIG. 1B

| | |
|---|---|
| 120 |  |
| 121 |  |
| 122 |  |
| 123 |  |
| 124 |  |
| 125 |  |
| 126 |  |
| 127 |  |
| 128 |  |
| 129 |  |
| 130 |  |
| 131 |  |
| 132 |  |

| | |
|---|---|
| 133 |  |
| 134 |  |
| 135 |  |
| 136 |  |
| 137 |  |
| 138 |  |
| 139 |  |
| 140 |  |
| 141 |  |
| 142 |  |
| 143 |  |
| 144 |  |
| 145 |  |
| 146 |  |

FIG. 1H

METABOTROPIC GLUTAMATE RECEPTOR ANTAGONISTS AND THEIR USE FOR TREATING CENTRAL NERVOUS SYSTEM DISEASES

This application is a continuation-in-part of PCT International Application No. PCT/US98/24833, filed Nov. 20, 1998, which was a continuation-in-part of U.S. Provisional Application Ser. No. 60/066,758, filed Nov. 21, 1997, and is a continuation-in-part of U.S. Provisional Application Ser. No. 60/137,272, filed Jun. 2, 1999, the specifications of which are hereby incorporated by reference in their entirety.

FIELD OF THE INVENTION

The present invention provides compounds that are active at metabotropic glutamate receptors and that are useful for treating neurological and psychiatric diseases and disorders.

BACKGROUND OF THE INVENTION

Recent advances in the elucidation of the neurophysiological roles of metabotropic glutamate receptors have established these receptors as promising drug targets in the therapy of acute and chronic neurological and psychiatric disorders and diseases. However, the major challenge to the realization of this promise has been the development of metabotropic glutamate receptor subtype-selective compounds.

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993); Schoepp, *Neurochem. Int.* 24:439 (1994); Pin et al., *Neuropharmacology* 34:1 (1995).

Eight distinct mGluR subtypes, termed mGluR1 through mGluR8, have been identified by molecular cloning. See, for example, Nakanishi, *Neuron* 13:1031 (1994); Pin et al., *Neuropharmacology* 34:1 (1995); Knopfel et al., *J. Med. Chem.* 38:1417 (1995). Further receptor diversity occurs via expression of alternatively spliced forms of certain mGluR subtypes. Pin et al., *PNAS* 89:10331 (1992); Minakami et al., *BBRC* 199:1136 (1994); Joly et al., *J. Neurosci.* 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Nakanishi, *Neuron* 13:1031 (1994); Pin et al., *Neuropharmacology* 34:1 (1995); Knopfel et al., *J. Med. Chem.* 38:1417 (1995).

Group I mGluRs comprise mGluR1, mGluR5, and their alternatively spliced variants. The binding of agonists to these receptors results in the activation of phospholipase C and the subsequent mobilization of intracellular calcium. Electrophysiological measurements have been used to demonstrate these effects in, for example, *Xenopus oocytes* expressing recombinant mGluR1 receptors. See, for example Masu et al., *Nature* 349:760 (1991); Pin et al., *PNAS* 89:10331 (1992). Similar results have been achieved with oocytes expressing recombinant mGluR5 receptors. Abe et al., *J. Biol. Chem.* 267:13361 (1992); Minakami et al., *BBRC* 199:1136 (1994); Joly et al., *J. Neurosci.* 15:3970 (1995). Alternatively, agonist activation of recombinant mGluR1 receptors expressed in Chinese hamster ovary (CHO) cells stimulates PI hydrolysis, cAMP formation, and arachidonic acid release as measured by standard biochemical assays. Aramori et al., *Neuron* 8:757 (1992).

In comparison, activation of mGluR5 receptors expressed in CHO cells stimulates PI hydrolysis and subsequent intracellular calcium transients, but no stimulation of cAMP formation or arachidonic acid release is observed. Abe et al., *J. Biol. Chem.* 267:13361 (1992). However, activation of mGluR5 receptors expressed in LLC-PK1 cells results in PI hydrolysis and increased cAMP formation. Joly et al., *J. Neurosci.* 15:3970 (1995). The agonist potency profile for Group I mGluRs is quisqualate>glutamate=ibotenate>(2S, 1'S,2'S)-2-carboxycyclopropyl)glycine (L-CCG-1)>(1S, 3R)-1-aminocyclopentane-1,3-dicarboxylic acid (ACPD). Quisqualate is relatively selective for Group I receptors, as compared to Group II and Group III mGluRs, but it also is a potent activator of ionotropic AMPA receptors. Pin et al., *Neuropharmacology* 34:1, Knopfel et al., *J. Med. Chem.* 38:1417 (1995).

The lack of subtype-specific mGluR agonists and antagonists has impeded elucidation of the physiological roles of particular mGluRs, and the mGluR-associated pathophysiological processes that affect the CNS have yet to be defined. However, work with the available non-specific agonists and antagonists has yielded some general insights about the Group I mGluRs as compared to the Group II and Group III mGluRs.

Attempts at elucidating the physiological roles of Group I mGluRs suggest that activation of these receptors elicits neuronal excitation. Various studies have demonstrated that ACPD can produce postsynaptic excitation upon application to neurons in the hippocampus, cerebral cortex, cerebellum, and thalamus, as well as other brain regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992); Schoepp, *Neurochem. Int.* 24:439 (1994); Pin et al., *Neuropharmacology* 34:1(1995).

Pharmacological experiments implicate Group I mGluRs as the mediators of this excitatory mechanism. The effects of ACPD can be reproduced by low concentrations of quisqualate in the presence of iGluR antagonists. Hu et al., *Brain Res.* 568:339 (1991); Greene et al., *Eur. J. Pharmacol.* 226:279 (1992). Two phenylglycine compounds known to activate mGluR1, namely (S)-3-hydroxyphenylglycine ((S)-3HPG) and (S)-3,5-dihydroxyphenylglycine ((S)-DHPG), also produce excitation. Watkins et al., *Trends Pharmacol. Sci.* 15:33 (1994). In addition, the excitation can be blocked by (S)-4-carboxyphenylglycine ((S)-4CPG), (S)-4-carboxy- 3-hydroxyphenylglycine ((S)-4C3HPG), and (+)-alpha-methyl-4-carboxyphenylglycine ((+)-MCPG), compounds known to be mGluR1 antagonists. Eaton et al., *Eur. J. Pharmacol.* 244:195 (1993); Watkins et al., *Trends Pharmacol. Sci.* 15:333 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993); Bortolotto et al., *Nature* 368:740 (1994); Aiba et al., *Cell* 79:365 (1994); Aiba et al., *Cell* 79:377 (1994). A role for mGluR activation in nociception and analgesia also has been demonstrated. Meller et al., *Neuroreport* 4: 879 (1993). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control, and control of the vestibulo-ocular reflex. For reviews, see Nakanishi, *Neuron* 13: 1031 (1994); Pin et al., *Neuropharmacology* 34:1; Knopfel et al., *J. Med. Chem.* 38:1417 (1995).

Metabotropic glutamate receptors also have been suggested to play roles in a variety of pathophysiological processes and disease states affecting the CNS. These include stroke, head trauma, anoxic and ischemic injuries, hypoglycemia, epilepsy, and neurodegenerative diseases such as Alzheimer's disease. Schoepp et al., *Trends Pharmacol. Sci.* 14:13 (1993); Cunningham et al., *Life Sci.* 54:135 (1994); Hollman et al., *Ann. Rev. Neurosci.* 17:31 (1994); Pin et al., *Neuropharmacology* 34:1 (1995); Knopfel et al., *J. Med. Chem.* 38:1417 (1995). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents or anticonvulsants.

Preliminary studies assessing therapeutic potentials with the available mGluR agonists and antagonists have yielded seemingly contradictory results. For example, it has been reported that application of ACPD onto hippocampal neurons leads to seizures and neuronal damage (Sacaan et. al., *Neurosci. Lett.* 139:77 (1992); Lipparti et al., *Life Sci.* 52:85 (1993). Other studies indicate, however, that ACPD inhibits epileptiform activity, and also can exhibit neuroprotective properties. Taschenberger et al., *Neuroreport* 3:629 (1992); Sheardown, *Neuroreport* 3:916 (1992); Koh et al., *Proc. Natl. Acad. Sci. USA* 88:9431 (1991); Chiamulera et al., *Eur. J. Pharmacol.* 216:335 (1992); Siliprandi et al., *Eur. J. Pharmacol.* 219:173 (1992); Pizzi et al., *J. Neurochem.* 61:683 (1993).

It is likely that these conflicting results are due to the lack of selectivity of ACPD, which causes activation of several different mGluR subtypes. In the studies finding neuronal damage it appears that Group I mGluRs were activated, thereby enhancing undesirable excitatory neurotransmission. In the studies showing neuroprotective effects it appears that activation of Group II and/or Group III mGluRs occurred, inhibiting presynaptic glutamate release, and diminishing excitatory neurotransmission.

This interpretation is consistent with the observation that (S)-4C3HPG, a Group I mGluR antagonist and Group II mGluR agonist, protects against audiogenic seizures in DBA/2 mice, while the Group II mGluR selective agonists DCG-IV and L-CCG-I protect neurons from NMDA- and KA-induced toxicity. Thomsen et al., *J. Neurochem.* 62:2492 (1994); Bruno et al., *Eur. J. Pharmacol.* 256:109 (1994); Pizzi et al., *J. Neurochem.* 61:683 (1993).

Based on the foregoing, it is clear that currently available mGluR agonists and antagonists have limited value, due to their lack of potency and selectivity. In addition, most currently available compounds are amino acids or amino acid derivatives that have limited bioavailabilities, thereby hampering in vivo studies to assess mGluR physiology, pharmacology and their therapeutic potential. Compounds that selectively inhibit activation of metabotropic glutamate receptor Group I subtypes should be useful for treatment of neurological disorders and diseases such as senile dementia, Parkinson's disease, Alzheimer's disease, Huntington's Chorea, pain, epilepsy, head trauma, anoxic and ischemic injuries, psychiatric disorders such as schizophrenia, depression, and anxiety, ophthalmological disorders such as various retinopathies, for example, diabetic retinopathies, glaucoma, and neurological disorders of a auditory nature such as tinnitus, and neuropathic pain disorders, including neuropathic diseases states such as diabetic neuropathies, chemotherapy induced neuropathies, post-herpetic neuralgia, and trigeminal neuralgia.

It is apparent, therefore, that identification of potent mGluR agonists and antagonists with high selectivity for individual mGluR subtypes, particularly for Group I receptor subtypes, are greatly to be desired.

SUMMARY OF THE INVENTION

It is an object of the present invention, therefore, to identify metabotopic glutamate receptor-active compounds which exhibit a high degree of potency and selectivity for individual metabotropic glutamate receptor subtypes, and to provide methods of making these compounds.

It is a further object of this invention to provide pharmaceutical compositions containing compounds which exhibit a high degree of potency and selectivity for individual metabotropic glutamate receptor subtypes, and to provide methods of making these pharmaceutical compositions.

It is yet another object of this invention to provide methods of inhibiting activation of an mGluR Group I receptor, and of inhibiting neuronal damage caused by excitatory activation of an mGluR Group I receptor.

It is still another object of the invention to provide methods of treating a disease associated with glutamate-induced neuronal damage.

To accomplish these and other objectives, the present invention provides potent antagonists of Group I metabotropic glutamate receptors. These antagonists may be represented by the formula I,

wherein R is an optionally substituted straight or branched chain alkyl, arylalkyl, cycloalkyl, or alkylcycloalkyl group containing 5–12 carbon atoms. Ar is an optionally substituted aromatic, heteroaromatic, arylalkyl, or heteroaralkyl moiety containing up to 10 carbon atoms and up to 4 heteroatoms, and [linker] is —(CH$_2$)$_n$—, where n is 2–6, and wherein up to 4 CH$_2$ groups may independently be substituted with groups selected from the group consisting of C$_1$–C$_3$ alkyl, CHOH, CO, O, S, SO, SO$_2$, N, NH, and NO. Two heteroatoms in the [linker] may not be adjacent except when those atoms are both N (as in —N=N— of —NH—NH—) or are N and S as in a sulfonamide. Two adjacent CH$_2$ groups in [linker] also may be replaced by a substituted or unsubstituted alkene or alkyne group. Pharmaceutically acceptable salts of the compounds also are provided.

In one embodiment of the invention, Ar comprises a ring system selected from the group consisting of benzene, thiazole, furyl, pyranyl, 2H-pyrrolyl, thienyl, pyrrolyl, imidazolyl, pyrazolyl, pyridyl, pyrazinyl, pyrimidinyl, pyridazinyl benzothiazole, benzimidazole, 3H-indolyl, indolyl, indazolyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl rings. Ar optionally may independently be substituted with up to two C$_1$–C$_3$ alkyl groups, or up to two halogen atoms, where halogen is selected from F, Cl, Br, and I.

In another embodiment of the invention, R contains 4, 5, 6, 7, 8, 9, 10 or 11 carbon atoms, where some or all of the hydrogen atoms on two carbon atoms optionally may be replaced with substituents independently selected from the group consisting of F, Cl, OH, OMe, =O, and —COOH.

In yet another embodiment [linker] comprises an amide, ester, or thioester group.

In a preferred embodiment, R comprises a moiety selected from the group consisting of substituted or unsubstituted adamantyl, 2-adamantyl, (1S,2S,3S,5R)-isopinocamphenyl, tricyclo[4.3.1.1(3,8)]undec-3-yl, (1S,2R,5S)-cis-myrtanyl, (1R,2R,4S)-isobornyl, (1R,2R,3R,5S)-isopinocamphenyl, (1S,2S,5S)-trans-myrtanyl, (1R,2R,5R)-trans-myrtanyl, (1R,2S,4S)-bornyl, 1-adamantanemethyl, 3-noradamantyl, (1S,2S,3S,5R)-3-pinanemethyl, cyclooctyl, α,α-dimethylphenethyl, (S)-2-phenyl-1-propyl, cycloheptyl, 4-methyl-2-hexyl groups, 2,2,3,3,4,4,4-heptafluorobutyl, 4-ketoadamantyl, 3-phenyl-2-methylpropyl, 3,5-dimethyladamantyl, trans-2-phenylcyclopropyl, 2-methylcyclohexyl, 3,3,5-trimethylcyclohexyl, 2-(o-methoxyphenyl)ethyl, 2-(1,2,3, 4-tetrahydronaphthyl), 4-phenylbutyl, 2-methyl-2-phenylbutyl, 2-(m-fluorophenyl)ethyl, 2-(p-fluorophenyl)ethyl, 2-(3-hydroxy-3-phenyl)propyl, (S)-2-hydroxy-2-phenylethyl, (R)-2-hydroxy-2-phenylethyl, 2-(3-m-chlorophenyl-2-methyl) propyl, 2-(3-p-chlorophenyl-2-methyl)propyl, 4-tert-butylcyclohexyl, (S)-1-(cyclohexyl)ethyl, 2-(3-(3,4-dimethylphenyl)-2-methyl)propyl, 3,3-dimethylbutyl, 2-(5-methyl)hexyl, 1-myrtanyl, 2-bornyl, 3-pinanemethyl, 2,2,3, 3,4,4,5,5-octafluoropentyl, p-fluoro-α,α-dimethylphenethyl, 2-naphthyl, 2-bornanyl, cyclohexylmethyl, 3-methylcyclohexyl, 4-methylcyclohexyl, 3,4-dimethylcyclohexyl, 5-chloro-tricyclo[2.2.1]heptyl, o-α,α-dimethylphenethyl, 2-indanyl, 2-spiro[4.5]decyl, 2-phenylethyl, 1-adamantylethyl, 1-(1-bicyclo[2.2.1]hept-2-yl)ethyl, 2-(2-methyl-2-phenylpropyl), 2-(o-fluorophenyl)ethyl, 1-(cyclohexyl) ethyl, and cyclohexyl.

In a still further embodiment of the invention, Ar comprises a group having the formula

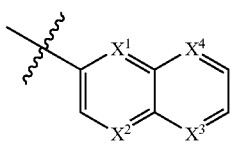

where X$^1$, X$^2$, X$^3$, and X$^4$ independently can be N or CH, provided that not more than two of X$^1$, X$^2$, X$^3$, and X$^4$ can be N. In a preferred embodiment, X$^1$ is N, and/or X$^2$ is N. In another embodiment, X$^3$ is N. In still another embodiment, X$^1$ is CH and X$^2$ is N.

In yet another embodiment, Ar is an optionally substituted 2-, 3-, or 4-pyridyl moiety, or Ar is a 6-benzothiazolyl moiety. The compound is selected from the group consisting of N-[6-(2-Methylquinolyl)]-1-adamantanecarboxamide, N-(6-Quinolyl)-1-adamantanecarboxamide, N-(2-Quinolyl)-1-adamantanecarboxamide, N-(3-Quinolyl)-1-adamantane-carboxamide, 6-Quinolyl-1-adamantanecarboxylate, 1-Adamantyl-6-quinolinecarboxylate, 2,2,3,3,4,4, 5,5-Octafluoro-1-pentyl-6-quinolinecarboxylate, 1-Adamantanemethyl-6-quinolinecarboxylate, 1-Adamantyl-2-quinoxalinecarboxylate, N-(1-Adamantyl)-3-quinoline-carboxamide, N-(1-Adamantyl)-2-quinolinecarboxamide, N-(2-Adamantyl)-2-quinoxalinecarboxamide, N-[(1R, 2R,3R,5S)-3-Pinanemethyl]-2-quinoxaline-carboxamide, N-(1-Adamantyl)-2-quinoxalinecarboxamide, N-(1-Adamantyl)-6-quinolinecarboxamide, N-(exo-2-Norbornanyl)-2-quinoxalinecarboxamide, N-[(1R,2S, 4S)-Bornyl]-2-quinoxalinecarboxamide, N-(3-Noradamantyl)-2-quinoxalinecarboxamide, N-[(1R,2R,3R,5S)Isopinocamphenyl]-2-quinoxalinecarboxamide, N-[(1S,2S,3S, 5R)-Isopinocamphenyl]-2-quinoxaline-carboxamide, N-(5-Chloro-[2.2.1.0]tricyclo-2,6-hepta-3-yl)-2-quinoxalinecarboxamide, N-([4.3.1.1]Tricyclo-3,8-undeca-3-yl)-2-quinoxalinecarboxamide, N-[(1S,2R,5S)-cis-Myrtanyl]-2-quinoxalinecarboxamide, N-[(1R,2R,4S) Isobornyl]-2-quinoxalinecarboxamide, N-[endo-(±)-2-Norbornanyl]-2-quinoxalinecarboxamide, N-[(R)-2-Phenyl-1 propyl]-2-quinoxalinecarboxamide, N-[(S)-2-Phenyl-1-propyl]-2-quinoxalinecarboxamide, N-(2-Indanyl)-2-quinoxalinecarboxamide, 1-Adamantanemethyl 6-quinolyl ether, 1-Adamantyl-3-quinolinecarboxylate, N-(α,α-Dimethylphenethyl)-2-quinoxalinecarboxamide, N-(α,α-Dimethyl-2-chlorophenethyl)-2-quinoxalinecarboxamide, N-(α,α-Dimethyl-4-fluorophenethyl)-2-quinoxalinecarboxamide, N-(β-Methylphenethyl)-2-quinoxalinecarboxamide, N-(3-Methylcyclohexyl)-2-quinoxalinecarboxamide, N-(2,3-Dimethylcyclohexyl)-2-quinoxalinecarboxamide, N-[(1S,2S,3S,SR)-3-Pinanemethyl]-2-quinoxaline-carboxamide, N-(1-Adamantanemethyl)-2-quinoxaline-carboxamide, N-(4-Methylcyclohexyl)-2-quinoxaline-carboxamide, N-[(1S,2S, 5S)-trans-Myrtanyl]-2-quinoxaline-carboxamide, and N-[(1R,2R,5R)-trans-Myrtanyl]-2-quinoxalinecarboxamide, and pharmaceutically acceptable salts thereof.

In a preferred embodiment, the compound is selected from the group consisting of N-(1-Adamantyl)-3-quinolinecarboxamide, N-(1-Adamantyl)-2-quinolinecarboxamide, N-(2-Adamantyl)-2-quinoxaline-carboxamide, N-[(1R,2R, 3R,5S)-3-Pinanemethyl]-2-quinoxaline-carboxamide, N-(1-Adamantyl)-2-quinoxaline-carboxamide, N-(1-Adamantyl)-6-quinolinecarboxamide, N-(exo-2-Norbornanyl)-2-quinoxaline-carboxamide, N-[(1R,2S,4S)-Bornyl]-2-quinoxaline-carboxamide, N-(3-Noradamantyl)-2-quinoxaline-carboxamide, N-[ (1R,2R,3R,5S)-Isopinocamphenyl]-2-quinoxaline-carboxamide, N-[(1S,2S, 3S,5R)-Isopinocamphenyl]-2-quinoxaline-carboxamide, N-(5-Chloro-[2.2.1.0]tricyclo-2,6-hepta-3-yl)-2-quinoxaline-carboxamide, N-([4.3.1.1]Tricyclo-3,8-undeca-3-yl)-2-quinoxaline-carboxamide, N-[(1S,2R,5S)-cis-Myrtanyl]-2-quinoxaline-carboxamide, N-[(1R,2R,4S)Isobornyl]-2-quinoxaline-carboxamide, N-[endo-(±)-2-Norbornanyl]-2-quinoxaline-carboxamide, N-[(1S,2S,3S,5R)-3-Pinanemethyl]-2-quinoxalinecarboxamide, N-(1-Adamantanemethyl)-2-quinoxalinecarboxamide, N-[(1S,2S, 5S)-trans-Myrtanyl]-2-quinoxalinecarboxamide, and N-[(1R,2R,5R)-trans-Myrtanyl]-2-quinoxalinecarboxamide, and pharmaceutically acceptable salts thereof.

In another embodiment, the compound is selected from the group consisting of N-[6-(2-Methylquinolyl)]-1-adamantanecarboxamide, N-(6-Quinolyl)-1-adamantane-carboxamide, N-(2-Quinolyl)-1-adamantanecarboxamide, and N-(3-Quinolyl)-1-adamantanecarboxamide, N-(3-Methylcyclohexyl)-2-quinoxalinecarboxamide, N-(2,3-Dimethylcyclohexyl)-2-quinoxalinecarboxamide, N-[(1S,2S,3S,5R)-3-Pinanemethyl]-2-quinoxalinecarboxamide, N-(1-Adamantanemethyl)-2-quinoxalinecarboxamide, and N-(4-Methylcyclohexyl)-2-quinoxalinecarboxamide, N-[(R)-2-Phenyl-1-propyl-2-quinoxalinecarboxamide, N-[(S)-2-Phenyl-1-propyl]-2-quinoxalinecarboxamide, N-(2-Indanyl)-2-2-quinoxalinecarboxanride, N-(α-α-Dimethylphenethyl)-2-quinoxalinecarboxamide, N-(α,α-Dimethyl-2-chlorophenethyl)-2-quinoxalinecarboxamide, N-(α,α-Dimethyl-4-fluorophenethyl)-2-quinoxaline-carboxamide, and N-(β-Methylphenethyl)-2-quinoxaline-carboxamide, 1-Adamantanemethyl 6-quinolyl ether, 6-Quinolyl-1-adamantanecarboxylate, 1-Adamantyl-6-quinolinecarboxylate, 2,2,3,3,4,4,5,5-Octafluoro-1-pentyl 6-quinolinecarboxylate, 1-Adamantanemethyl 6-quinolinecarboxylate, 1-Adamantyl-2-quinoxalinecarboxylate, and 1-Adamantyl-3-quinolinecarboxylate, and pharmaceutically acceptable salts thereof.

In yet another embodiment, the compound is selected from the group consisting of 3-(1-Adamantanemethoxy)-2-chloroquinoxaline, 2-(1-Adamantanemethoxy)-3-methylquinoxaline, 3-(1-Adamantanemethoxy)-2-fluoroquinoxaline, 2-(1-Adamantanemethoxy)-3-trifluoromethylquinoxaline, N-[2-(4-Phenylthiazolyl)]-1-adamantanecarboxamide, N-[2-(5-Methyl-4-phenylthiazolyl)]-1-adamantanecarboxamide, 1-(1-Adamantyl)-2-(benzothiazol-2-ylsulfanyl)ethanone, N-(1-Adamantyl)-2-chloroquinoxaline-3-carboxamide, N-(1-Adamantyl)-3-methylquinoxaline-2-carboxamide, and N-(1-Adamantyl)-1-oxyquinoxaline-3-carboxamide, 4-Chlorophenyl 3-coumarincarboxylate, 2-(1-Adamantanemethylsulfanyl)quinoxaline, 3-(1-Adamantanemethoxy)-2-chloropyrazine, 1-(1-Adamantyl)-2-(4,6-dimethylpyrimidin-2-ylsulfanyl)ethanone, 1-(1-Adamantyl)-2-(2-anisylsulfanyl)ethanone, 3-(1-Adarnantanemethoxy)-1H-quinoxalin-2-one, 1-(1-Adamantyl)-2-(3-anisylsulfanyl)ethanone, 1-(1-Adamantyl)-2-(4-anisylsulfanyl)ethanone, 1-(1-Adamantyl)-2-(4-chlorophenylsulfanyl)ethanone, 1-(1-Adamantyl)-2-(2-naphthylsulfanyl)ethanone, N-(2-[6-(1-Piperidinyl)pyrazinyl])-1-adamantanecarboxamide, N-(2-[6-(1-Piperidinyl)pyrazinyl])adamantan-1-ylmethylcarboxamide, 1-(1-Adamantyl)-2-(1-naphthylsulfanyl)ethanone, 1-(1-Adamantyl)-2-(8-quinotylsulfanyl)ethanone hydrochloride, 1-(1-Adamantyl)-2-(4-trifluoromethoxyphenoxy)ethanone, 2-(1-Adamantanemethoxy)quinoxaline, N-(trans-4-Methylcyclohexyl)-2-quinoxalinecarboxamide, N-(cis-4-Methylcyclohexyl)-2-quinoxalinecarboxamide, N-(trans-4-Methylcyclohexyl)-2-quinolinecarboxamide, N-(trans-4-Methylcyclohexyl)-3-quinolinecarboxamide, and N-(trans-4-Methylcyclohexyl)-6-quinolinecarboxamide, 2-(1-Adamantanemethylsulfinyl)-benzothiazole, N-(4-Phenylbutyl)-2-quinoxalinecarboxamide, 1-(1-Adamantyl)-2-(4,6-dimethylpyrimidin-2-ylsulfanyl)ethanol, 1-(1-Adamantyl)-2-(3-chloroquinoxal-2-yl)ethanone, 2-(1-Adamantanemethylsulfanyl)-3-methylquinoxaline, N-(1-Adamantyl)-2-anisamide, N-(1-Adamantanemethyl)-2-anisamide, 1-(1-Adamantyl)-2-(4-chlorophenylsulfanyl)ethanone, 2-(1-Adamantanemethylsulfonyl)-3-methylquinoxaline, 1-(1-Adamantyl)-2-(4-fluorophenylsulfanyl)ethanone, 1-(1-Adamantyl)-2-(3-fluorophenylsulfanyl)ethanone, 1-(1-Adamantyl)-2-(2-methoxyphenoxy)ethanone, 1-(4-Anisylsulfanyl)butan-2-one, 1-(1-Adamantyl)-2-(4-anisidinyl)ethanone hydrochloride, 3,3-Dimethyl-1-(4-anisylsulfanyl)butan-2-one, 1-(4-Biphenyl)-2-(4-anisylsulfanyl)ethanone, 1-(1-Adamantyl)-2-(2-trifluoromethoxyphenylsulfanyl)ethanone, 1-(1-Adarnantyl)-2-(3-methylquinoxal-2-ylsulfanyl) ethanone, 1-(1-Adamantyl)-2-(2-anisidinyl)ethanone hydrochloride, 1-(1-Adamantyl)-2-(4-trifluoromethoxyphenylamino)ethanone hydrochloride, 1-(1-Adamantyl)-2-(N-methyl-4-anisidinyl)ethanone hydrochloride, N-(1-Adamantyl)-7-trifluoromethylquinoline-3-carboxamide, N-(1-Adamantyl)-2-(1-piperizinyl)quinoxaline-3-carboxamide, N-(1-Adamantyl)-2-(2-aminoethylamino)quinoxaline-3-carboxamide, Methyl N-(3-quinolyl)-3-carboxyadamantane-1-carboxamide, 1-(1-Adamantyl)-2-[(R)-1-(1-naphthyl)ethan-1-ylamino]ethanone, N-(1-Adamantyl)-2-methoxyquinoxaline-3-carboxamide, Ethyl N-(1-adamantyl)-2-(3-propanoylamino)quinoxaline-3-carboxamide, N-(4-Chlorophenyl)-2,3-dimethylquinoxaline-6-carboxamide, N-(1-Adamantyl)-6,7-dimethylquinoxaline-2-carboxamide, N-((S)-1-Tetralinyl)-2-quinoxalinecarboxamide, N-(4-Chlorophenyl)-2-quinoxalinecarboxamide, N-(6-Quinolyl)-2-quinoxalinecarboxamide, N-(1-Tetralinmethyl)-2-quinoxalinecarboxamide, N-(1-Indanmethyl)-2-quinoxalinecarboxamide, N-(4,4-Dimethylcyclohexyl)-2-quinoxalinecarboxamide, and pharmaceutically acceptable salts thereof.

In yet other embodiments, the compound is selected from the group consisting of N-[2-(2-fluorophenyl)propyl]quinoxaline-2-carboxamide, N-(pentyl)quinoxaline-2-carboxamide, N-(trans-4-phenylcyclohexyl)quinoxaline-2-carboxamide, N-(trans-4-methylcyclohexyl)indole-5-carboxamide, N-(6-quinolinyl)-4-methylcyclohexane-1-carboxamide, N-(1-methyl-4-phenylcyclohexyl)quinoxaline-2-carboxamide, N-(trans-4-methylcyclohexyl)benzothiaphene-2-carboxamide, N-(trans-4-methylcyclohexyl)benzofuran-2-carboxamide, N-(3-quinolinyl)quinoxaline-2-carboxamide hydrochloride, N-(trans-4-methylcyclohexyl)-6-bromopicolinamide, N-(adamantyl)-5-(1-piperidine)nicotinamide, N-(trans-4-methylcyclohexyl)-2-carboxamidebenzothiazole, N-[2-(2,6-difluorophenyl)ethyl]quinoxaline-2-carboxamide, N-(trans-4-methylcyclohexyl)-6-methoxyquinoline-3-carboxamide, N-(trans-4-methylcyclohexyl)-7-methoxyquinoline-3-carboxamide, N-(trans-4-methylcyclohexyl)-5-fluoroquinoline-3-carboxamide, N-(trans-4-methylcyclohexyl)-7-fluoroquinoline-3-carboxamide, N-(trans-4-methylcyclohexyl)-6-fluoroquinoline-3-carboxamide, N-(trans-4-methylcyclohexyl)-8-fluoroquinoline-3-carboxamide, N-(trans-4-methylcyclohexyl)-6,7-methylenedioxyquinoline-3-carboxamide, N-(trans-4-methylcyclohexyl)-6,7-ethylenedioxyquinoline-3-carboxamide, N-(trans-4-methylcyclohexyl)-6,8-difluoroquinoline-3-carboxamide, N-(trans-4-methylcyclohexyl)-6-methoxy-7-fluoroquinoline-3-carboxamide, N-(trans-4 -methylcyclohexyl)-7-trifluoromethylquinoline-3-carboxamide, N-(trans-4-methylcyclohexyl)-8-trifluoromethylquinoline-3-carboxamide, N-(trans-4-methylcyclohexyl)-6-fluoroquinoxaline-2-carboxamide, N-(trans-4-methylcyclohexyl)-5-fluoroquinoxaline-2-carboxamide, N-(trans-4-methylcyclohexyl)-6-trifluoromethylquinoxaline-2-carboxamide, N-(trans-4-methylcyclohexyl)-6-methoxyquinoxaline-2-carboxamide, and N-(trans-4-methylcyclohexyl)-6,7-methylenedioxyquinoxaline-2-carboxamide, N-(1-adamantyl)-2-quinoxalinecarboxamide, N-(α,α-dimethylphenethyl)-2-quinoxalinecarboxamide, N-(3-noradamantyl)-2-quinoxalinecarboxamide, N-[(1S,2R,5S)-cis-myrtanyl]-2-quinoxalinecarboxamide, (1-adamantylmethyl)-2-(3-chloro)quinoxalyether, (1-adamantylmethyl)-2-(3-methyl)quinoxalyether, N-(6-quinolinyl)quinoxaline-2-carboxamide, N-(trans-4-methylcyclohexyl)-2-quinoxalinecarboxamide, N-(4,4-dimethylcyclohexyl)quinoxaline-2-carboxamide, N-(trans-4-methylcyclohexyl)quinoline-2-carboxamide, N-(trans-4-methylcyclohexyl)quinoline-3-carboxamide, and N-(trans-4-methylcyclohexyl)quinoline-6-carboxamide, and pharmaceutically acceptable salts thereof.

In another embodiment, the compound has the structure

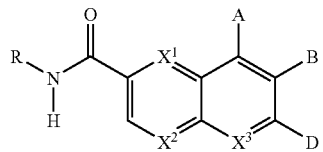

Where $X^1$ and $X^2$ independently are CH or N, $X^3$ is N or C-E, A, B, D, and E independently are selected from the group consisting of H, OMe, F, and $CF_3$, (preferably at least two of A, B, D, and E are H), or B and D together are —O—$(CH_2)$—O— or O—$(CH_2)_2$—O—, R is selected from the group consisting of $C_4$–$C_6$ alkyl,

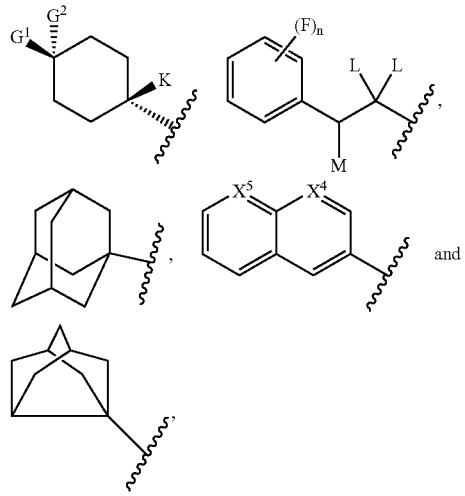

where K is H or Me, $G^1$ is H, Me, or phenyl, $G^2$, K, L, and M independently are H or Me, n is 0, 1 or 2, and $X^4$ and $X^5$ independently are N or CH.

In accordance with another embodiment of the invention, there has been provided a pharmaceutical composition comprising a compound as set forth above, together with a pharmaceutically acceptable diluent or excipient.

In accordance with still another embodiment of the invention, there has been provided a method of making a compound as set forth above, comprising reacting a compound containing an activated carboxylic acid group with a compound containing an amine, hydroxyl, or thiol group.

In accordance with a still further embodiment of the invention, there has been provided a method of inhibiting activation of an mGluR Group I receptor, comprising treating a cell containing said mGluR Group I receptor with an effective amount of a compound as set forth above.

In yet another embodiment of the invention, there has been provided a method of inhibiting neuronal damage caused by excitatory activation of an mGluR Group I receptor, comprising treating neurons with an effective amount of a compound as set forth above.

In accordance with a further embodiment of the invention, there has been provided a method of treating a disease associated with glutamate-induced neuronal damage, comprising administering to a patient suffering from said disease an effective amount of a composition as set forth above.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1A:
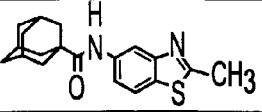
FIGS. 1A–1N show illustrative compounds of the present invention.
Figure 1C:
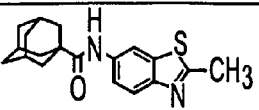
Figure 1D:
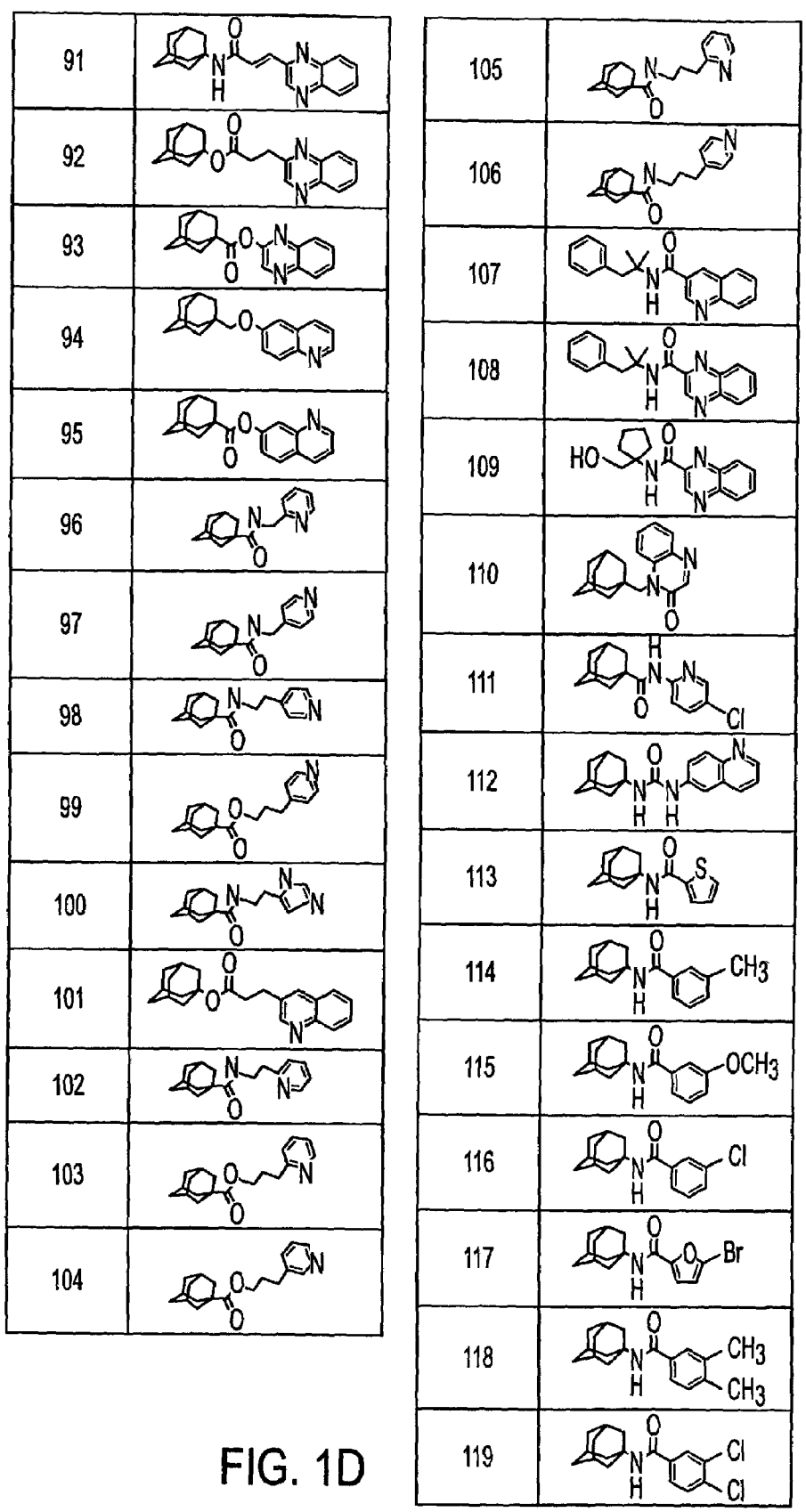
Figure 1E:
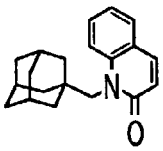
Figure 1E:
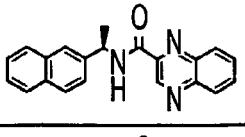
Figure 1E:
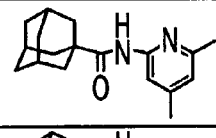
Figure 1E:
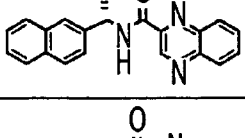
Figure 1E:
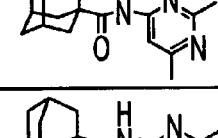
Figure 1E:
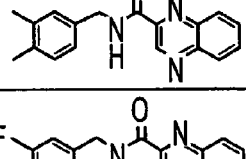
Figure 1E:
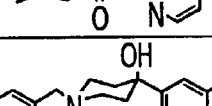
Figure 1E:
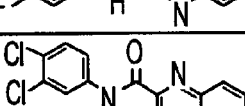
Figure 1E:
Figure 1E:
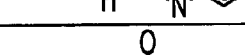
Figure 1E:
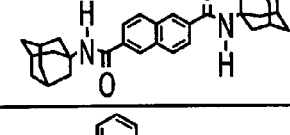
Figure 1E:
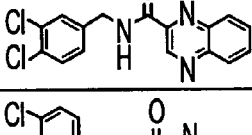
Figure 1E:
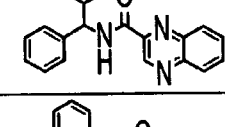
Figure 1E:
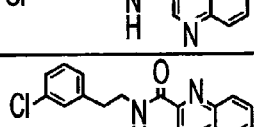
Figure 1E:
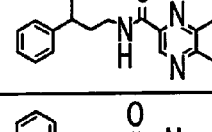
Figure 1E:
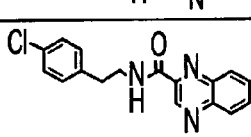
Figure 1E:
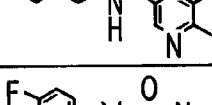
Figure 1E:
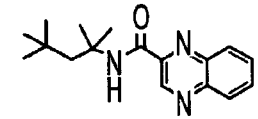
Figure 1E:
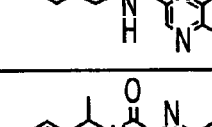
Figure 1E:
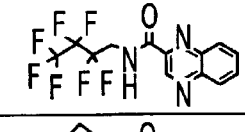
Figure 1E:
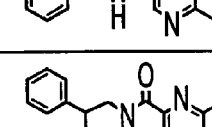
Figure 1E:
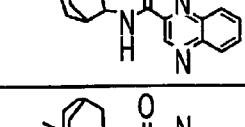
Figure 1E:
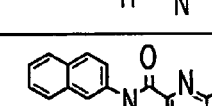
Figure 1E:
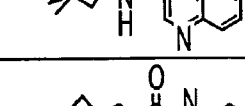
Figure 1E:
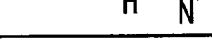
Figure 1E:
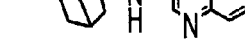
Figure 1E:
Figure 1F:
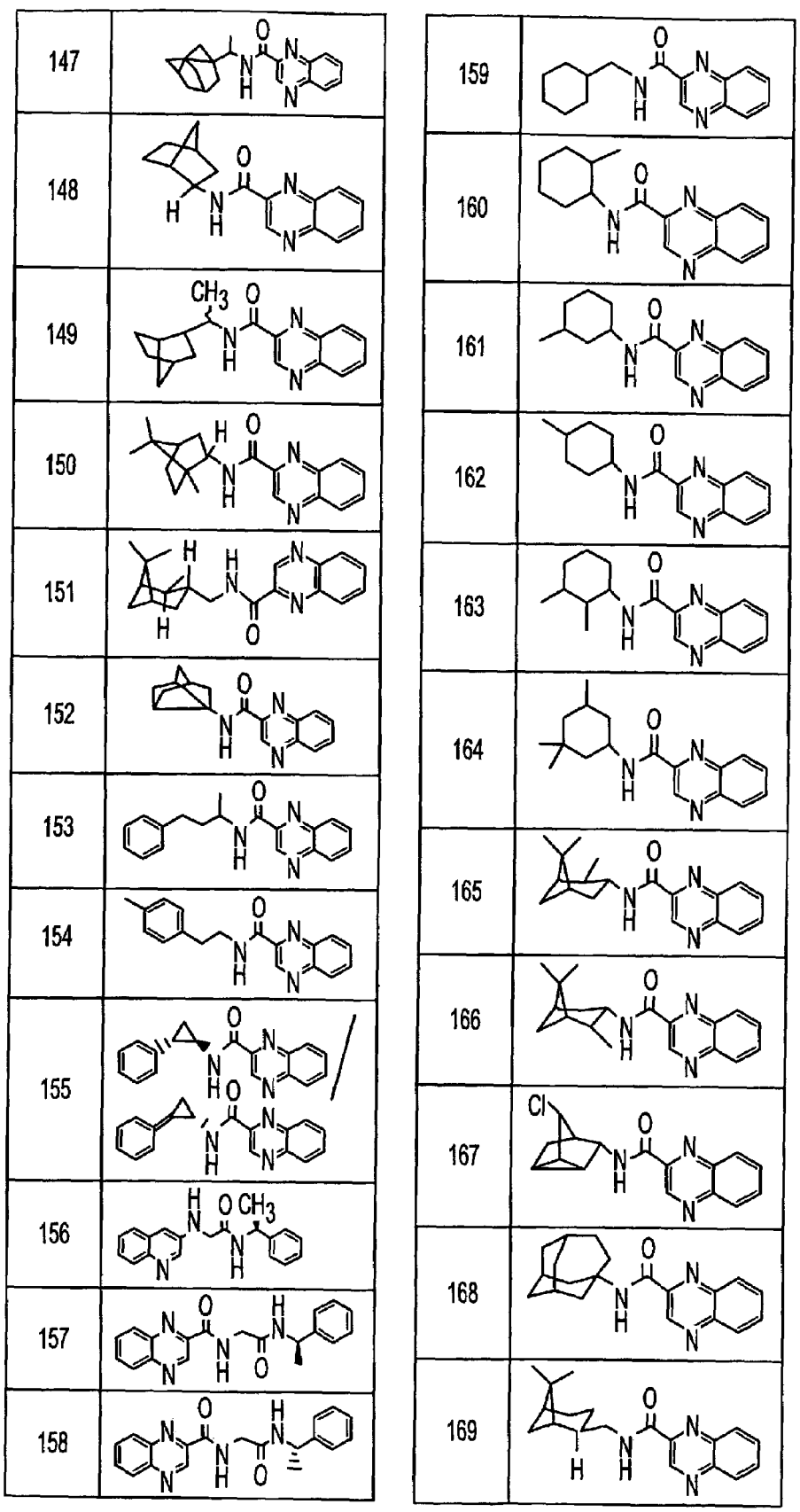
Figure 1G:
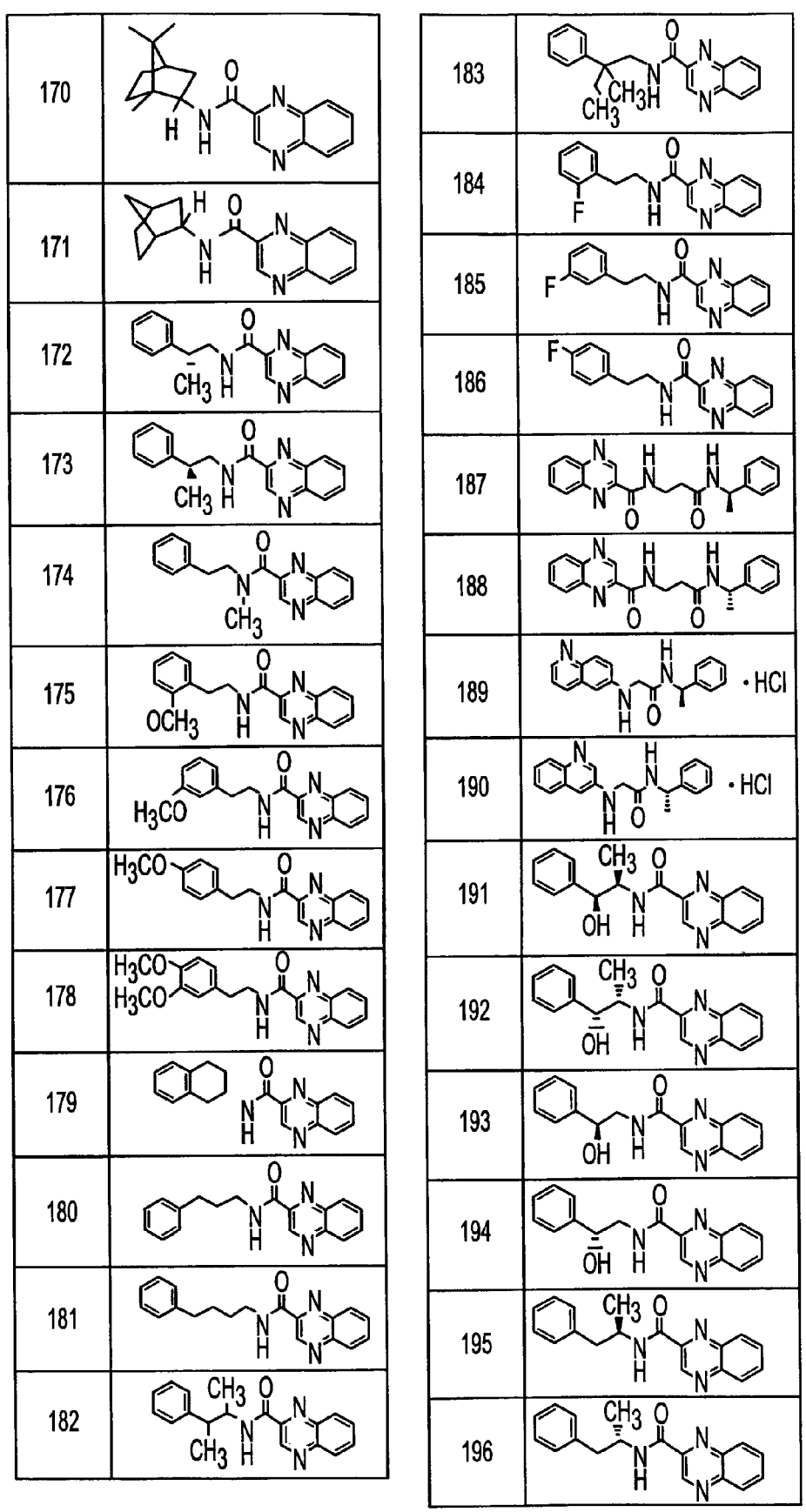
Figure 1I:
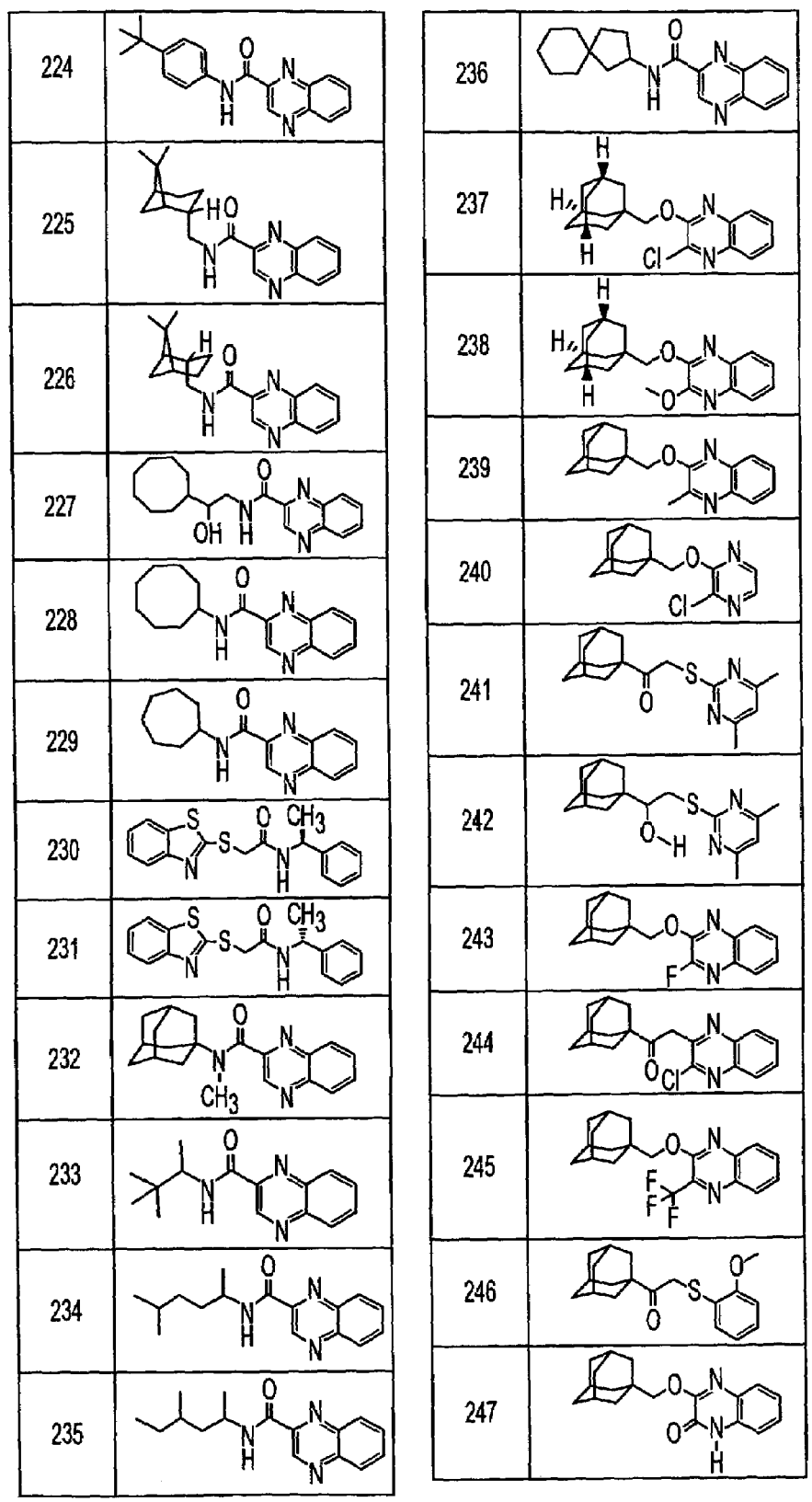
Figure 1J:
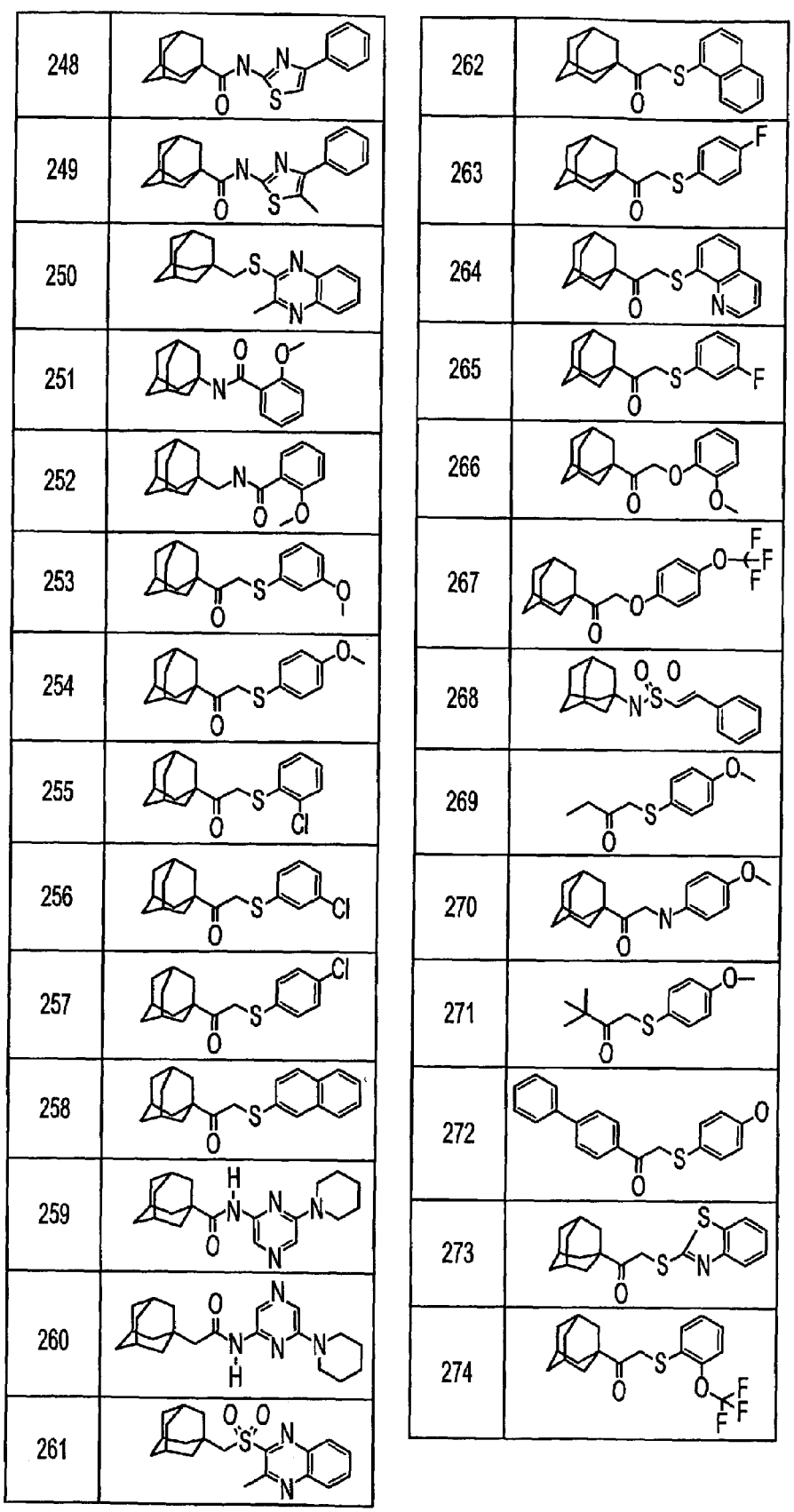
Figure 1K:
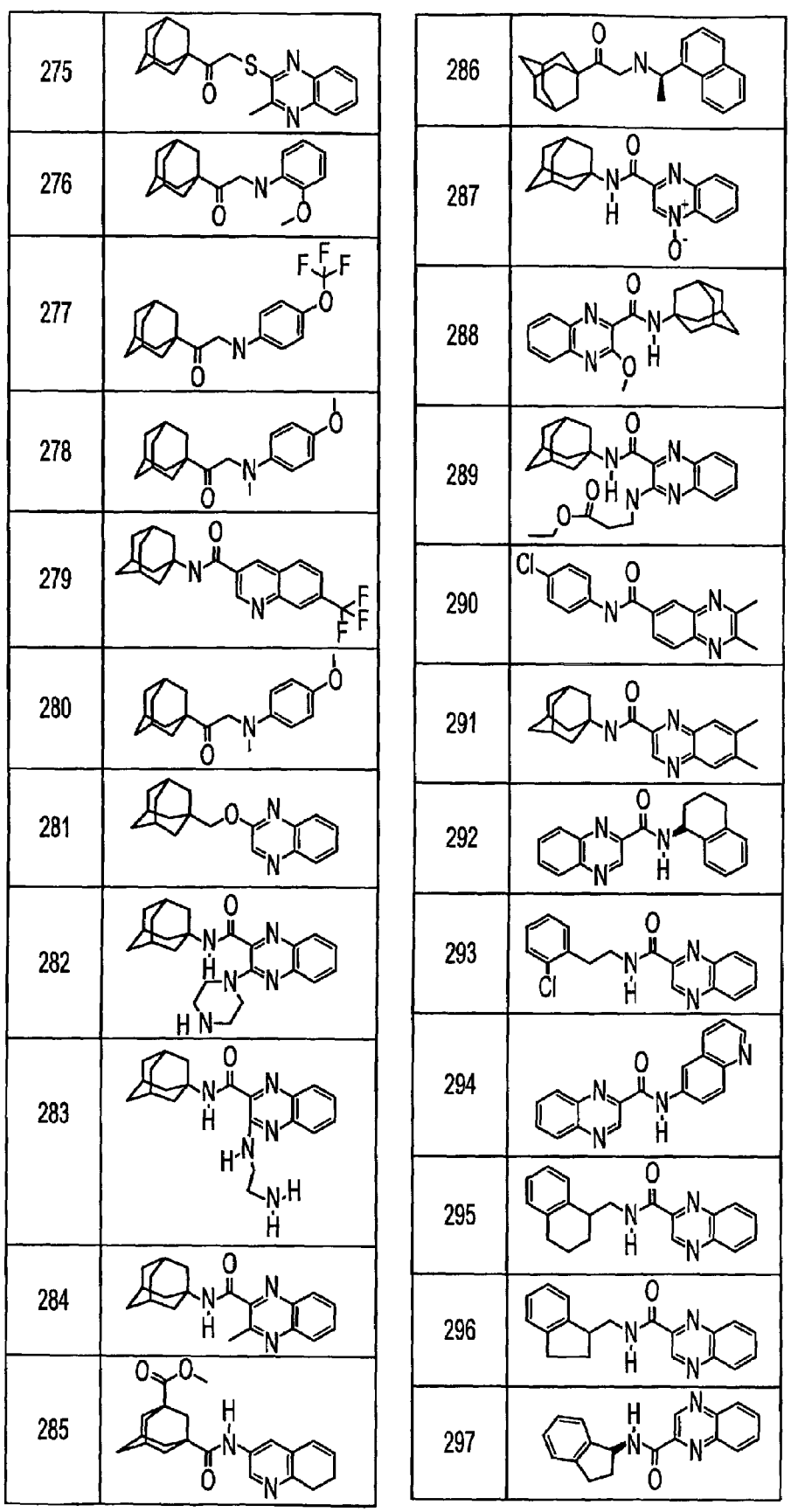
Figure 1L:
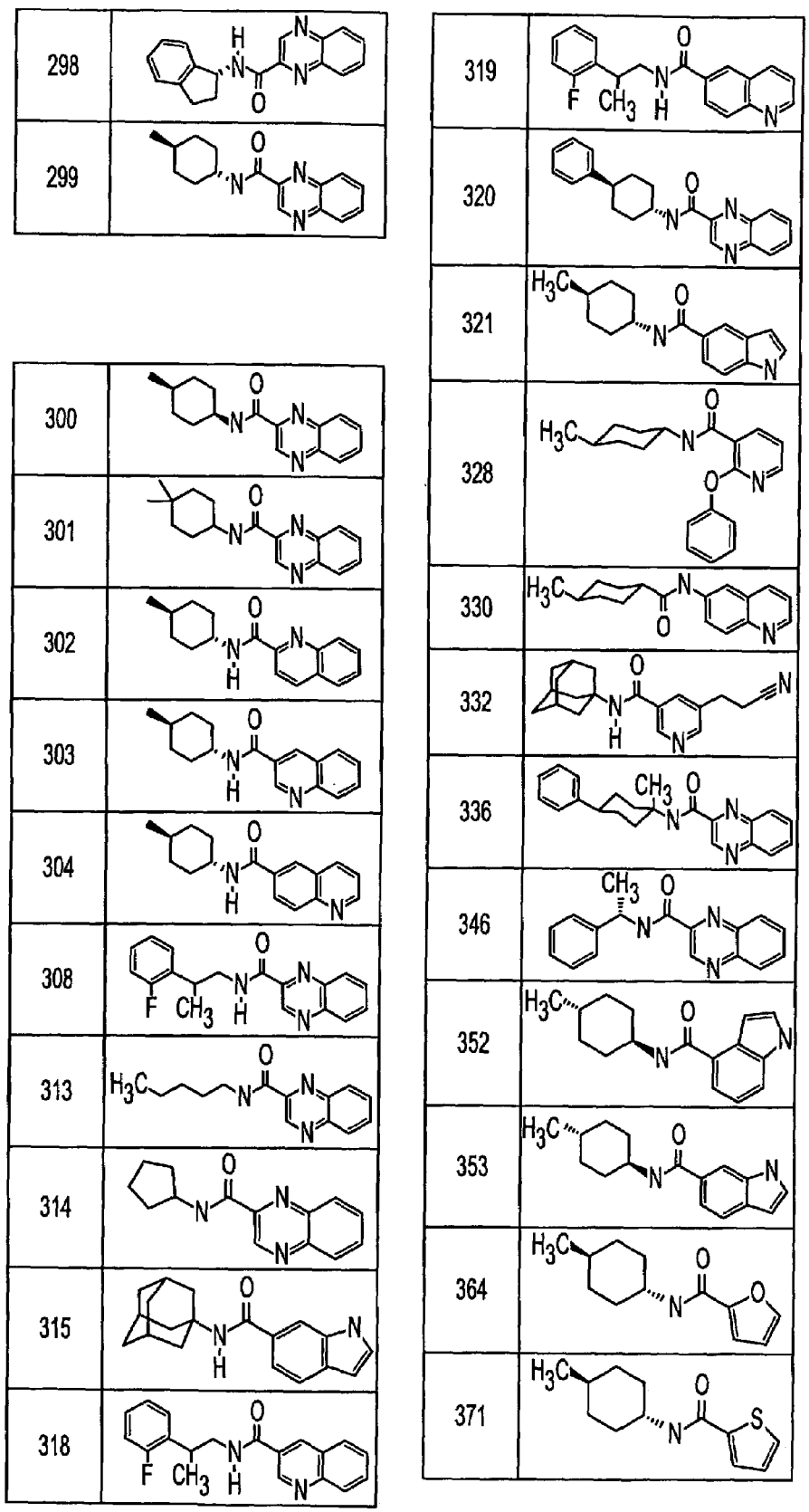
Figure 1M:
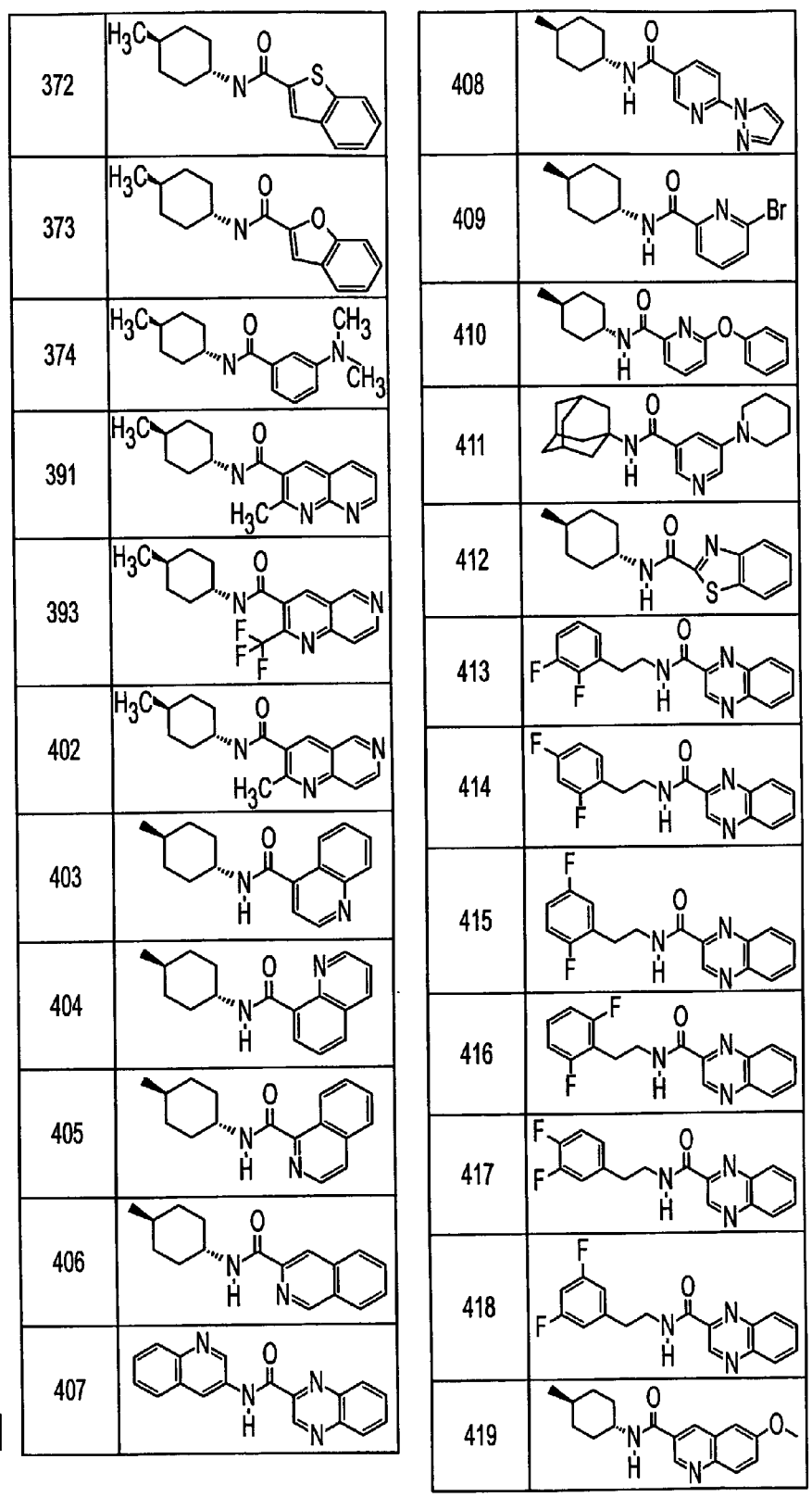
Figure 1N:
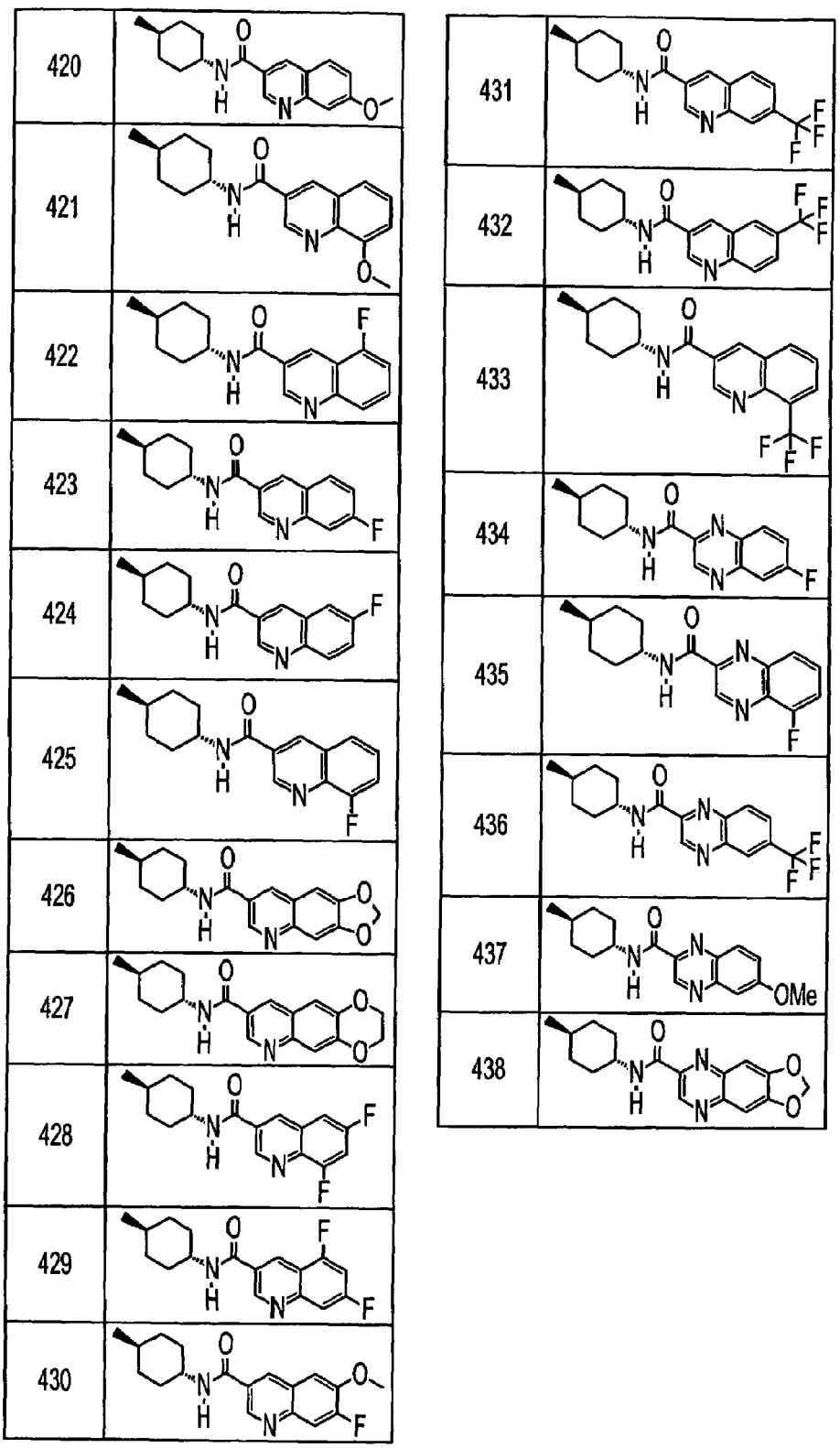

The invention provides compounds that are potent and selective antagonists of Group I metabotropic glutamate receptors. The compounds contemplated by the invention can be represented by the general formula I:

R–[Linker]–Ar where R is a straight or branched chain alkyl, arylalkyl, or optionally substituted alicyclic group, and Ar is an optionally substituted aromatic, heteroaromatic, arylalkyl, or heteroaralkyl moiety. The [linker] moiety is a group that not only covalently binds to the Ar and R moieties, but also facilitates adoption of the correct spatial orientation by Ar and R to allow receptor binding.

Structure of the Ar moiety

The Ar moiety generally may contain up to ten carbon atoms, although the skilled artisan will recognize that Ar groups with more than ten carbon atoms are within the scope of the invention. Ar can be a monocyclic or fused bicyclic aryl, alkaryl, heteroaryl or heteroarylalkyl group. The ring systems encompassed by Ar can contain up to four heteroatoms, independently selected from the group consisting of N, S, and O. When Ar is a heteroaryl ring or ring system, it preferably contains one or two heteroatoms. At least one of the heteroatoms preferably is N.

Monocyclic Ar groups include, but are not limited to: phenyl, thiazoyl, furyl, pyranyl, 2H-pyrrolyl, thienyl, pyrroyl, imidazoyl, pyrazoyl, pyridyl, pyrazinyl, pyrimidinyl, and pyridazinyl moieties. Fused bicyclic Ar groups include, but are not limited to: benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl moieties. Ar preferably is a quinoxalinyl, quinolinyl, or pyridyl moiety.

Other Ar moieties include the 3,4-methylenedioxy and 3,4-dioxane rings. The Ar moiety optionally may independently be substituted with up to two $C_1$–$C_3$ alkyl groups, or up to two halogen atoms, where halogen is selected from F, Cl, Br, and I.

Structure of the R moiety

The R moiety generally may contain between four and eleven carbon atoms, although the skilled artisan will recognize that R moieties with 12, 13, 14, 15, or 16 carbon atoms will be possible. Although R can contain 4, 5 or 6 carbon atoms, preferably R contains at least 7 carbon atoms. Preferably, R is optionally substituted alkyl, cycloalkyl, cycloalkylmethyl, or optionally substituted phenylalkyl. Generally, some or all of the hydrogen atoms on up to two methine, methylene, or methyl groups of R may be replaced by substituents independently selected from the group consisting of F, Cl, OH, OMe, =O, and —COOH groups. However, more than two hydrogen atoms may be replaced with fluorine, and R may be perfluorinated.

Exemplary R moieties include, but are not limited to: adamantyl, 2-adamantyl, (1S,2S,3S,5R)-isopinocamphenyl, tricyclo[4.3.1.1(3,8)]undec-3-yl, (1S,2R,5S)-cis-myrtanyl, (1R,2R,4S)-isobornyl, (1R,2R,3R,5S)-isopinocamphenyl (1S,2S ,5S)-trans-myrtanyl (1R,2R,5R)-trans-myrtanyl, (1R,2S, 4S)-bornyl, 1-adamantanemethyl, 3-noradamantyl (1S,2S,3S,5R)-3-pinanemethyl, cyclooctyl, dimethylphenethyl, (S)-2-phenyl-1-propyl, cycloheptyl, and 4-methyl-2-hexyl groups. Each of these exemplary R moieties may also be substituted in the manner set forth above.

Other preferred R groups include 2,2,3,3,4,4,4-heptafluorobutyl, 4-ketoadamantyl, 3-phenyl-2-methylpropyl, 3,5-dimethyladamantyl, trans-2-phenylcyclopropyl, 2-methylcyclohexyl, 3,3,5-trimethylcyclohexyl, 2-(o-methoxyphenyl)ethyl, 2-(1,2,3,4-tetrahydronaphthyl), 4-phenylbutyl, 2-methyl-2-phenylbutyl, 2-(m-fluorophenyl) ethyl, 2-(p-fluorophenyl)ethyl, 2-(3-hydroxy-3-phenyl)propyl, (S)-2-hydroxy-2-phenylethyl, (R)-2-hydroxy-2-phenylethyl, 2-(3-m-chlorophenyl-2-methyl)propyl, 2-(3-p-chlorophenyl-2-methyl)propyl, 4-tert-butyl-cyclohexyl, (S)-1-(cyclohexyl)ethyl, 2-(3-(3,4-dimethylphenyl)-2-methyl) propyl, 3,3-dimethylbutyl, 2-(5-methyl)hexyl, 1-myrtanyl, 2-bornyl, 3-pinanemethyl, 2,2,3,3,4,4,5,5-octafluoropentyl, p-fluoro-2,2-dimethylphenethyl, 2-naphthyl, 2-bornanyl, cyclohexylmethyl, 3-methylcyclohexyl, 4-methylcyclohexyl, 3,4-dimethylcyclohexyl, 5-chloro-tricyclo[2.2.1]heptyl, o- , -dimethylphenethyl, 2-indanyl, 2-spiro[4.5]decyl, 2-phenylethyl, 1-adamantylethyl, 1-(1-bicyclo[2.2.1]hept-2-yl)ethyl, 2-(2-methyl-2-phenylpropyl), 2-(o-fluorophenyl) ethyl, 1-(cyclohexyl)ethyl, cyclohexyl, butan-2-onyl, diphenylene, 3-carboxyladamantyl, 1-tetrahydronaphthelenyl, 1-indanyl, 4-methylcyclohexyl, and 4,4-dimethylcyclohexyl moieties. Again, each of these exemplary R moieties may be substituted in the manner set forth above. When compounds may be present in alternative isomeric configurations, for example, trans or cis-4-methylcyclohexyl, the R moiety may have any of the possible configurations. Similarly, if a compound exists as enantiomers, the R moiety can be either of the enantiomers, or may be a racemate.

Structure of the [linker] Moiety

The [linker] moiety generally has the structure —$(CH_2)_n$—, where n is 2–6. Up to four $CH_2$ groups may independently be replaced with groups selected from the group consisting of a $C_1$–$C_3$ alkyl group, CHOH, CO, O, S, SO, SO2, N, NH, and NO, provided that two heteroatoms may not be adjacent except when those atoms are both N (forming an —N=N— or —NH—NH— linkage), or those atoms are N and S as in a sulfonamide. The sulfonamide can have either orientation with respect to the R and Ar moieties. Any two adjacent $CH_2$ groups also may be replaced by an alkene or alkyne group.

In a preferred embodiment, [linker] comprises an amide, ester, thioester, ketomethylene, ether, alkylether, ethylene, ethenyl, acetylenyl, hydroxyalkyl, alkylsulfone, or alkyl alkylsulfoxide group. Preferably, [linker] is an —O—$(CH_2)_m$—, —CO—Y—$(CH_2)_m$—, or —S(O)$_n$—$(CH_2)_m$— group, where Y is $CH_2$, NH, O, or S, and m is 1–4, and n is 0–2. The [linker] moiety may have either one of two possible orientations with respect to the R and Ar groups. Thus, for example, the invention encompasses compounds having the configuration R—O—$(CH_2)_m$—Ar and R—$(CH_2)_m$—O—R.

Design and Synthesis of mGluR Group I Antagonists

In one embodiment, compounds according to the invention are esters and amides of monocyclic or fused bicyclic aromatic and heteroaromatic carboxylic acids, phenols and amines. In a preferred embodiment, the compounds may be represented by the Formulae II or III:

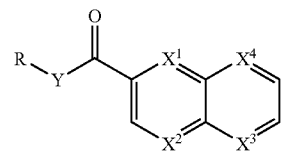

II

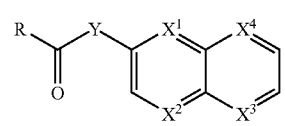

III

In Formulae II and III, Y can be either O, S, NH, or $CH_2$; and $X^1$, $X^2$, $X^3$, and $X^4$ independently can be N or CH. Preferably, one or two of $X^1$, $X^2$, $X^3$, and $X^4$ are N, and the remainder are CH. Preferred compounds contemplated by the invention have the formula IV or V, where R, Y and $X^1$ are as defined above.

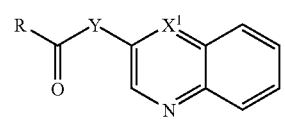

IV

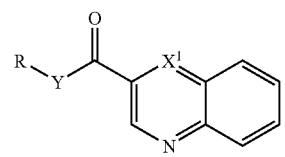

V

In another preferred embodiment of the invention, the compounds have the Formulae VI or VII:

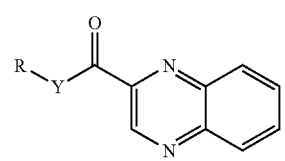

VI

-continued

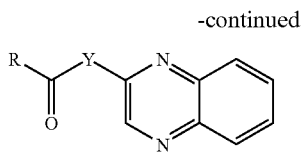

VII where R and Y are as defined above. In a first embodiment of the compounds of Formula VI, Y is N, R is an unsubstituted or monosubstituted 1,1,-dimethylphenylethylamine or 1,1-dimethylbenzylamine moiety, where the substitutuent preferably is an o-, m-, or p-chlorine or p-methoxy group. In a second embodiment of the compounds of Formula VI, Y is N, and R is an o-, m-, or p-methoxy substituted phenylethylamine. Compounds of the first and second embodiments appear to exhibit selectivity for the mGluR$_1$ receptor. In a third embodiment, of the compounds of Formula VI, Y is N, and R is an o, m, or p-fluoro-substituted phenylethylamine. Compounds of the third embodiment appear not to discriminate between the mGluR$_1$ and mGluR$_5$ receptor subtypes.

In yet another preferred embodiment of the invention, the compounds have the Formulae VIII or IX:

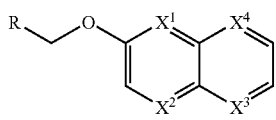

VIII

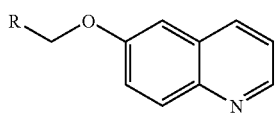

IX wherein $X^{1-4}$ and R are as defined above. In a first embodiment of compounds of Formula VIII, $X^1$ and $X^2$ are N, $X^3$ and $X^4$ are H, R is 1-adamantyl, and a substituent is present on the carbon atom ortho to both the linker and $X^2$. The substituent preferably is a halogen, such as chlorine, or an alkyl group, such as methyl. In a second embodiment of compound IX, R is 1-adamantyl. Compounds of these first and second embodiments appear to exhibit selectivity for the mGluR$_1$ receptor.

In still another embodiment, the compounds may have the Formulae X or XI, where Z is a pharmaceutically acceptable substituent. The skilled artisan will recognize that pharmaceutically acceptable Z groups are those groups that do not deleteriously reduce the receptor binding activity of the compound. Suitable Z groups include, but are not limited to halogen, lower alkyl, oxygen or amine, and their pharmaceutically acceptable derivatives including ethers, esters, and amides. Preferably, Z contains 0–4 carbon atoms.

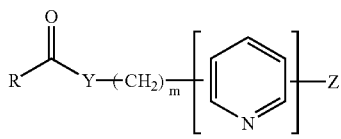

X

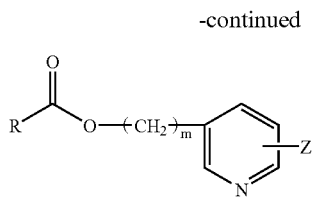

XI

In each of the compounds described above, "alkyl" denotes both straight and branched chain alkyl. In other embodiments, R is adamantyl, the linker is —CO—CH$_2$—S—, and Ar is m- or o-alkyloxyphenyl, or 3,4-methylenedioxy or 3,4-dioxane.

In general, it appears that selective antagonism of the mGluR1 receptor can be attained with compounds of the formula R—CO—N—Ar$_1$, where Ar$_1$ is an aromatic or heteroaromatic group such as a quinolinyl, quinoxalinyl, thiazolidinyl, phenyl, benzimidazoyl, or pyridyl group.

The skilled artisan also will recognize that the compounds of the invention encompass salts of the compounds described above. These salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, malonic, succinic, citric, mandelic, benzoic, cinnamic, methanesulfonic and similar ones, and include acids related to the pharmaceutically acceptable salts listed in the *Journal of Pharmaceutical Sciences,* 66:2 (1977) and incorporated herein by reference.

Examples of compounds according to the present invention are set forth in Table 1 below.

Preparation of mGluR Group I Antagonists

The skilled artisan will recognize that mGluR Group I antagonists according to the invention may be prepared by methods that are well known in the art, using widely recognized techniques of organic chemistry. Suitable reactions are described in standard textbooks of organic chemistry. For example, see March, *Advanced Organic Chemistry,* 2d ed., McGraw Hill (1977).

For example, the compounds generally may be prepared by formation of the [linker] moiety between two precursor compounds containing suitable Ar and R moieties. When the linker contains an amide linkage, the amide may be formed using well known techniques, such as reaction between an amine and an acid chloride, or by reaction in the presence of a coupling reagent such as carbonyldiimidazole, or a carbodiimide such as, for example, 1,3-dicyclohexylcarbodiimide (DCC). Formation of ester and thioester linkages can be achieved in similar fashion.

When the [linker] moiety contains an ether linkage, the ether function also can be prepared using standard techniques. For example, ethers can be formed using the Mitsunobu reaction, where a primary alcohol function is displaced by another hydroxy group via activation using PPh$_3$ and diethylazodicarboxylate (DEAD). Thioether linkages may be prepared by displacement of a leaving group such as halide with a thiolate anion, generated by deprotonation of a thiol group with base.

When the [linker] moiety contains a ketomethylene group, it can be formed by alkylation of a ketone enolate. Thus, for example, a methyl ketone can be deprotonated using a strong base such as lithium diisopropylamide (LDA), followed by reaction with an alkyl halide. Alternatively, a ketomethylene function can be prepared via addition of an organometallic compound, such as a Grignard reagent, to an aldehyde, followed by oxidation of the resultant hydroxyl group to a ketone. Suitable reagents for oxidizing alcohols to ketones are well known in the art.

[Linker] moieties containing other heteroatom groups also may be prepared using methods that are well known in the art. N,N'-Disubstituted hydrazine compounds may be prepared via reductive amination of hydrazones formed by reaction of a monosubstituted hydrazone with an aldehyde. N,N'-Disubstituted azo compounds can be formed, for example, by oxidation of the corresponding hydrazines.

In most cases, the precursor Ar and R moieties are readily available, or may be prepared using straightforward techniques of organic chemistry. Many compounds are commercially available, for example, from Aldrich Chemical Company, Milwaukee, Wis. When the compounds are not commercially available, they may readily prepared from available precursors using straightforward transformations that are well known in the art.

For example, carboxylic acids may be converted into the corresponding acid chlorides by reaction with, for example, thionyl chloride or oxalyl chloride. An example of such a reaction is provided below in Example 3. Compounds containing a hydroxy function may be converted into the corresponding amine by (i) conversion of the hydroxyl group into a leaving group, such as a sulfonic acid ester (such as a triflate, mesylate, or tosylate) or a halide, (ii) displacement with azide ion, and (iii) reduction of the resulting azide by, for example, hydrogenation over a platinum oxide catalyst. An illustration of such a transformation is provided below in Example 12.

Testing of Compounds for mGluR Group I Antagonist Activity

The pharmacological properties of the compounds of the invention can be analyzed using standard assays for functional activity. Examples of glutamate receptor assays are well known in the art, for example, see Aramori et al., *Neuron* 8:757 (1992); Tanabe et al., *Neuron* 8:169 (1992). The methodology described in those publications is incorporated herein by reference.

Conveniently, the compounds of the invention may be studied using an assay that measures inhibition of intracellular calcium mobilization in cells expressing recombinant receptors that can bind the compounds. Suitable receptor constructs are well known in the art and are also described, for example, in WO 97/05252, the contents of which are hereby incorporated by reference in their entirety.

Thus, HEK-293 cells (human embryonic kidney cells, available from the American Type Culture Collection, Rockville, Md., Accession Number CRL 1573) are stably transfected with a DNA construct expressing a recombinant receptor. The stably transfected cells are cultured in high glucose DMEM (Gibco 092) containing 0.8 mM glutamine, 10% FBS, and 200 µM hygromycin B.

A protocol for measuring intracellular calcium mobilization in response to changes in extracellular calcium using the calcium-sensitive dye Fura has been described previously. Briefly, HEK-293 cells, stably transfected with a DNA construct encoding a recombinant receptor, are loaded with Fura dye. The cells then are washed, resuspended, and maintained at 37° C. The cells are diluted into cuvettes for recording fluorescent signals. Measurements of fluorescence are performed at 37° C. using standard methods, and concentrations of intracellular $Ca^{2+}$ are calculated using a dissociation constant (Kd) of 224 nM and applying equation:

$$[Ca^{2+}]_i = (F - F_{min}/F_{max}) \times Kd$$

where F is fluorescence at any particular time of interest, $F_{min}$ is determined by chelating all calcium available, therefore, no fura 2 is bound to calcium, and $F_{max}$ is determined by fully saturating all the fura 2 available with calcium.

A detailed protocol for testing the compounds of the invention is provided below at Example 15.

Preparation of Pharmaceutical Compositions Containing mGluR Antagonists, and Their Use in Treating Neurological Disorders The compounds of the invention are useful for treating neurological disorders or diseases. While these compounds will typically be used in therapy for human patients, they may also be used in veterinary medicine to treat similar or identical diseases.

In therapeutic and/or diagnostic applications, the compounds of the invention can be formulated for a variety of modes of administration, including systemic and topical or localized administration. Techniques and formulations generally may be found in *Remington's Pharmaceutical Sciences*: Drug Receptors and Receptor Theory, 18th ed., Mack Publishing Co. (1990).

The compounds according to the invention are effective over a wide dosage range. For example, in the treatment of adult humans, dosages from about 0.01 to about 1000 mg, preferably from about 0.5 to about 100 mg, per day may be used. A most preferable dosage is about 2 mg to about 70 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/disphosphate, polygalacturonate, salicylate, stearate, subacetate, succinate, sulfate, tannate, tartrate, or teoclate. Other pharmaceutically acceptable salts may be found in, for example, *Remington's Pharmaceutical Sciences*; (18th ed.), Mack Publishing Co., Easton, Pa. (1990).

Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-release form as is known to those skilled in the art. Techniques for formulation and administration may be found in *Remington's Pharmaceutical Sciences*; (18th ed.), Mack Publishing Co., Easton, Pa. (1990). Suitable routes may include oral, buccal, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

The present invention, thus generally described, will be understood more readily by reference to the following examples, which are provided by way of illustration and are not intended to be limiting of the present invention.

EXAMPLES

General Experimental Methods

Capillary gas chromatographic and mass spectral data were obtained using a Hewlett-Packard (HP) 5890 Series II Gas Chromatograph coupled to an HP 5971 Series Mass Selective Detector [Ultra-2 Ultra Performance Capillary Column (crosslinked 5% PhMe silicone); column length, 25 m; column i.d., 0.20 mm; helium flow rate, 60 mL/min; injector temp., 250° C.; temperature program, 20 C/min from 125 to 325° C. for 10 min, then held constant at 325° C. for 6 min]. Thin-layer chromatography was performed using Analtech Uniplate 250-μm silica gel HF TLC plates. UV light sometimes in conjunction with ninhydrin and Dragendorff's spray reagents (Sigma Chemical Co.) were used for detecting compounds on the TLC plates. Reagents used in reactions were purchased from the Aldrich Chemical Co. (Milwaukee, Wis.), Sigma Chemical Co. (Saint Louis, Mo.), Fluka Chemical Corp. (Milwaukee, Wis.), Fisher Scientific (Pittsburgh, Pa.), TCI America (Portland, Oreg.), or Lancaster Synthesis (Windham, N.H.).

Example 1

Preparation of
N-[6-(2-Methylquinolyl)]-1-adamantanecarboxamide
(40)

2-Methyl-6-aminoquinoline

A mixture of 2-methyl-6-nitroquinoline (1.00 g, 5.31 mmol) and Pearlman's catalyst [palladium dihydroxide on activated charcoal (~20% palladium); 0.10 g] in ethyl acetate (40 mL) was stirred under hydrogen gas (1 atm) at 60° C. for 1.5 h. The reaction mixture was filtered and the filtrate was rotary evaporated. This provided 0.81. g (96%) of 2-methyl-6-aminoquinoline as a yellow solid.

N-[6-(2-Methylquinolyl)]-1-adamantanecarboxamide (40)

1-Adamantanecarbonyl chloride (1.02 g, 5.13 mmol) in pyridine (2 mL) was added to a solution of 2-methyl-6-aminoquinoline (0.81 g, 5.1 mmol) in pyridine (8 mL). The reaction was stirred for 17 h. To the stirring reaction mixture was added water (100 mL) which caused the product to precipitate. This precipitate was filtered and then washed with water (3×25 mL) and diethyl ether (3×25 mL). This provided 1.07 g (65%) of (40) as a cream-colored powder:

rt=13.49 min.; m/z (rel. int.) 320 (M+, 30), 235 (8), 158 (4), 157 (6), 136 (11), 135 (100), 130 (11), 107 (7), 93 (15), 91 (8), 79 (18), 77 (11), 67 (6).

In a similar manner, the following N-quinolyl-1-adamantanecarboxamides were prepared:

N-(6-Quinolyl)-1-adamantanecarboxamide (18)

Prepared from 1-adamantanecarbonyl chloride (1.37 g, 6.90 mmol), 6-aminoquinoline (0.59 g, 4.1 mmol), pyridine (20 mL), and water (200 mL) yielding 1.25 g (100%) of (18):

rt=13.24 min.; m/z (rel. int.) 306 (M+, 23), 221 (6), 144 (3), 136 (12), 135 (100), 116 (10), 107 (7), 93 (15), 91 (8), 79 (18), 77 (9), 67 (7), 41 (6).

N-(2-Quinolyl)-1-adamantanecarboxamide Hydrochloride (81)

Prepared from 1-adamantanecarbonyl chloride (0.75 g, 3.8 mmol), 2-aminoquinoline (0.60 g, 4.2 mmol), pyridine (10 mL), and water (100 mL). Forming the hydrochloride salt with diethyl ethereal hydrogen chloride yielded 0.19 g(15%)of(81):

rt=12.24 min; m/z (rel. int.) 306 (M+, 80), 305 (23), 277 (8), 263 (8), 221 (10), 172 (9), 171 (72), 145 (16), 144 (61), 143 (13), 136 (11), 135 (100), 128 (33), 117 (17), 116 (24), 107 (18), 105 (8), 101 (10), 93 (40), 91 (29), 89 (13), 81 (14), 79 (55), 77 (35), 67 (18), 65 (10), 55 (12), 53 (10), 41 (20).

N-(3-Quinolyl)-1-adamantanecarboxamide (86)

Prepared from 1-adamantanecarbonyl chloride (0.75 g, 3.8 mmol), 3-aminoquinoline (0.60 g, 4.2 mmol), pyridine (10 mL), and water (100 mL) yielding 0.33 g (29%) of (86):

rt=13.01 min.; m/z (rel. int.) 306 (M+, 22), 136 (11), 135 (100), 116 (11), 107 (8), 93 (15), 91 (8), 89 (7), 79 (17), 77 (8), 67 (6), 65 (3).

N-(trans-4-Methylcyclohexyl)-2-quinoxalinecarboxamide (299)

Using the method of Booth (J. Chem. Soc., 1958, 2688; J. Chem. Soc., 1971, 1047; Tetrahedron, 1967, 23, 2421), hydroxylamine (3.8 g, 55 mmol), ethanol (50 mL), pyridine (4.44 mL, 55 mmol), and 4-methyl cyclohexanone (6.1 mL, 50 mmol) were stirred at ambient temperature for 16 hours and then heated at reflux for 15 minutes. The ethanol was then removed in vacuo and the residual oil dissolved in ethylacetate (100 mL). The organic layer was washed with water (2×), brine, dried over anhydrous $MgSO_4$, filtered, and concentrated to a clear oil (the oxime product), which crystallized upon standing.

Without further purification 1.9 g (15 mmol) of the intermediate oxime in absolute ethanol (40 mL) was heated to reflux and treated with (in small portions) sodium metal (4 g). The reaction was heated at reflux until the sodium was consumed. The reaction was cooled and treated with water (10 mL). The reaction was transferred into a flask containing ice and concentrated HCl (6 mL). The ethanol was removed in vacuo and the remaining aqueous phase washed with diethyl ether (3×, to remove unreduced oxime). The remaining aqueous phase was concentrated to afford 1.8 g of a white crystalline solid (the trans-4-methylcyclohexylamine hydrochloride product).

Without further purification 750 mg (5 mmol) of trans-4-methylcyclohexyl amine hydrochloride in dichloromethane (10 mL) was treated with pyridine (1.62 mL, 20 mmol) followed by the addition of 2-quinoxaloyl chloride (963 mg, 55 mmol). The reaction was stirred at ambient temperature for 16 hours and diluted with chloroform (25 mL). The organics were washed with 10% HCl (3×), 1 N NaOH (3×), brine, dried over anhydrous $MgSO_4$, filtered and concentrated to a solid. Chromatography (MPLC) of the crude reaction material through silica (7×4 cm i.d., BIOTAGE, KP-SIL, 60 angstroms) using ethylacetate-hexane (1:4) afforded 470 mg of the desired product, N-(trans-4-methylcyclohexyl)-2-quinoxalinecarboxamide. Thin-layer chromatography (TLC, silica) using ethylacetate-hexane (1:4) showed a single UV active component at $R_f$ 0.19. GC/EI-MS gave m/z (rel. int.) 269 (M+, 39), 212 (8), 198 (6), 174 (15), 157 (21), 129 (100), 112 (43), and 102 (46).

Example 2

Preparation of 6-Quinolyl 1-adamantanecarboxylate (41)

1-Adamantanecarbonyl chloride (1.37 g, 6.90 mmol) in pyridine (5 mL) was added to a solution of 6-hydroxyquinoline (1.00 g, 6.89 mmol) in pyridine (15 mL). The reaction was stirred for 16 h. To the stirring reaction mixture was added water (200 mL) which caused the product to precipitate. This precipitate was filtered, washed with water (3×50 mL), and dried under high vacuum. This provided 1.56 g (73.7%) of (41) as a light-brown powder:

rt=11.41 min.; m/z (rel. int.) 307 (M+, 2), 136 (11), 135 (100), 116 (11), 107 (7), 93 (14), 92 (2), 91 (8), 89 (7), 79 (16), 77 (8).

Example 3

Preparation of 1-Adamantyl 6-quinolinecarboxylate (61)

6-Quinolinecarbonyl Chloride Hydrochloride

6-Quinolinecarboxylic acid was refluxed in thionyl chloride for 30 min. The excess thionyl chloride was then removed by rotary evaporation (90° C.) to provide 6-quinolinecarbonyl chloride hydrochloride.

1-Adamantyl 6-quinolinecarboxylate (61)

6-Quinolinecarbonyl chloride hydrochloride (0.76 g, 3.3 mmol) in pyridine (2 mL) was added to a solution of 1-adamantanol (0.60 g, 3.9 mmol) in pyridine (8 mL). The reaction was stirred at 70° C. for 16 h. To the stirring reaction mixture was added water (100 mL) which caused the product to precipitate. This precipitate was filtered and then washed with water (3×25 mL). The filter cake was dissolved in ethanol (20 mL) and water was then added to the cloud point (16 mL). The crystallizing solution was allowed to stand for 15 h. Filtering and drying under high vacuum for 7 h provided 0.32 g (26%) of (61) as light brown needle-like crystals:

rt=11.48 min.; m/z (rel. int.) 307 (M+, 99), 306 (92), 262 (15), 174 (12), 173 (13), 157 (10), 156 (88), 135 (81), 134(33), 129 (13), 128 (100), 127 (10), 119 (11), 107 (18), 102 (16), 101 (37), 93 (51), 92 (76), 91 (35), 81 (14), 79 (55), 78 (15), 77 (49), 75 (17), 67 (24), 55 (18), 53 (13), 51 (13), 41 (31).

In a similar manner, the following alkyl 6-quinoline- and 2-quinoxalinecarboxylates were prepared:

2,2,3,3,4,4,5,5-Octafluoro-1-pentyl-6-quinoline-carboxylate Hydrochloride (68)

Prepared from 6-quinolinecarbonyl chloride hydrochloride (0.75 g, 3.3 mmol), 2,2,3,3,4,4,5,5-octafluoro-1-pentanol (0.60 mL, 4.3 mmol), pyridine (10 mL), and water (100 mL). Forming the hydrochloride salt with ethereal hydrogen chloride yielded 0.88 g (69%) of (68):

rt=7.11 min.; m/z (rel. int.) 387 (M+, 26), 156 (100), 129 (6), 128 (48), 102 (6), 101 (16), 77 (6), 76 (2), 75 (8), 50 (14).

1-Adamantanemethyl 6-quinolinecarboxylate (73)

Prepared from 6-quinolinecarbonyl chloride hydrochloride (0.80 g, 3.5 mmol), 1-adamantanemethanol (0.60 g, 3.6 mmol), pyridine (10 mL), and water (100 mL) yielding 0.75 g (65%) of (73):

rt=11.90 min.; (rel. int.) 321 (M+, 35), 320 (12), 263 (15), 156 (30), 148 (23), 136 (11), 135 (100), 135 (100), 129 (9), 128 (52), 107 (15), 106 (7), 105 (9), 102 (7), 101 (16), 93

(34), 92 (20), 91 (20), 81 (11), 80 (7), 79 (40), 78 (6), 77 (24), 75 (7), 67 (14), 55 (9), 53 (6), 51 (6), 41 (14).

1-Adamantyl 2-quinoxalinecarboxylate (92)

Prepared from 2-quinoxaloyl chloride (0.84 g, 4.4 mmol), 1-adamantanol (0.60 g, 3.9 mmol), pyridine (10 mL), and water (100 mL) yielding 0.20 g (16%) of (92):

rt=11.21 min.; m/z (rel. int.) 308 (M+, 26), 264 (6), 136 (11), 136 (11), 135 (100), 134 (5), 130 (11), 129 (25), 107 (12), 102 (19), 93 (24), 92 (9), 91 (11), 81 (7), 79 (26), 77 (12), 76 (6), 75 (7), 67 (10), 55 (7), 51 (6), 41 (11).

Example 4

Preparation of
N-(1-Adamantyl)-3-quinolinecarboxamide (72)

1,1'-Carbonyldiimidazole (161 mg, 1.00 mmol) in N,N-dimethylformamide (1 mL) was added in one portion to a suspension of 3-quinolinecarboxylic acid (173 mg, 1.00 mmol) in N,N-dimethylformamide is (1 mL). The resulting reaction solution was stirred for 2.5 h. 1-Adamantanamine (151 mg, 1.00 mmol) in N,N-dimethylformamide (0.5 mL) was added in one portion. The reaction mixture was stirred at 60° C. for 2 h. The reaction was then diluted with chloroform and washed with water (3×30 mL). The organic layer was dried (anhydrous magnesium sulfate), filtered through silica gel, and rotary evaporated. This provided 73 mg (24%) of (72) as a crystalline solid:

rt=11.02 min.; m/z (rel. int.) 306 (M+, 78), 305 (42), 250 (19), 249 (100), 213 (7), 173 (5), 157 (10), 156 (89), 129 (12), 128 (92), 102 (5), 101 (36), 94 (6), 93 (O), 92 (12), 91 (14), 79 (10), 77 (14), 77 (14), 75 (10), 67 (7), 41 (11).

In a similar manner, the following N-alkyl-2-quinoline- and 2-quinoxalinecarboxamides were prepared:

N-(1-Adamantyl)-2-quinolinecarboxamide (74)

Prepared from 1,1'-carbonyldiimidazole (160 mg, 0.987 mmol), quinaldic acid (173 mg, 1.00 mmol), and N,N-dimethylformamide (2.5 mL) yielding 77 mg (25%) of (74):

rt=10.53 min.; m/z (rel. int.) 306 (M+, 91), 305 (26), 277 (9), 263 (9), 221 (11), 172 (9), 171 (73), 145 (15), 144 (60), 143 (15), 136 (11), 135 (100), 128 (36), 117 (19), 116 (27), 107 (20), 105 (8), 101 (10), 93 (42), 91 (30), 89 (14), 81 (13), 79 (55), 77 (37), 67 (18), 65 (11), 55 (12), 53 (10), 41 (18).

N-(2-Adamantyl)-2-quinoxalinecarboxamide (144)

Prepared from 1,1'-carbonyldiimidazole (161 mg, 1.00 mmol), 2-quinoxalinecarboxylic acid (174 mg, 1.00 mmol), 2-adamantanamine (136 mg, 0.90 mmol), and dichloromethane (3.5 mL) yielding 98 mg (35%) of (144):

rt=11.79 min.; m/z (rel. int.) 307 (M+, 33), 151 (12), 150 (100), 130 (24), 129 (35), 103 (11), 102 (20), 91 (13),79 (11), 77 (8), 76 (6), 75 (5), 70 (6), 67 (5), 41 (6).

N-[(1R,2R,3R,5S)-3-Pinanemethyl]-2-quinoxalinecarboxamide (151)

Prepared from 1,1'-carbonyldiimidazole (161 mg, 1.00 mmol), 2-quinoxalinecarboxylic acid (174 mg, 1.00 mmol), (−)-3-pinanemethylamine (150 mg, 0.90 mmol), and dichloromethane (3.5 mL) yielding 50 mg (17%) of (151):

rt=11.46 min.; m/z (rel. int.) 323 (M+, 7), 187 (76), 186 (10), 174 (25), 166 (15), 158 (44), 157 (20), 144 (6), 131 (10), 130 (78), 129 (100), 107 (8), 103 (21), 102 (44), 95 (15), 93 (10), 91 (9), 81 (11), 79 (13), 77 (12), 76 (14), 75 (11), 69 (8), 67 (17), 55 (20), 53 (10), 51 (7), 43 (10), 41 (30).

Example 5

Preparation of
N-(1-Adamantyl)-2-quinoxalinecarboxamide (91)

2-Quinoxaloyl chloride (0.84 g, 4.4 mmol) was added to a solution of 1-adamantanamine (0.60 g, 4.0 mmol) in pyridine (10 mL). The reaction was then stirred for 30 min. To the stirring reaction mixture was added water (100 mL) which caused the product to precipitate. This precipitate was filtered, washed with water (3×25 mL), and dried under high vacuum for 16 h. This provided 1.00 g (82%) of (91):

rt=11.73 min.; m/z (rel. int.) 307 (M+, 39), 279 (5), 157 (5), 151 (11), 150 (100), 130 (21), 129 (58), 103 (12), 102 (24), 94 (7), 93 (8), 91 (10), 79 (9), 77 (9), 76 (7), 75 (6), 67 (5), 41 (8), 41 (8).

In a similar manner, the following N-substituted 6-quino-line- and 2-quinoxalinecarboxamides were prepared:

N-(1-Adamantyl)-6-quinolinecarboxamide (42)

Prepared from 6-quinolinecarbonyl chloride hydrochloride (1.51 g, 10 mmol), 1-adamantanamine (1.73 g, 10 mmol), pyridine (5 mL), and water (200 mL) yielding 330 mg (11%) of (42):

rt=11.04 min.; m/z (rel. int.) 306 (M+, 34), 305 (15), 250 (11), 249 (56), 156 (11), 155 (100), 130 (5), 128 (10), 127 (69), 126 (5), 102 (8), 101 (16), 93 (8), 92 (9), 91 (12), 79 (10), 77 (16), 67 (6), 41 (11), 41 (11).

N-(exo-2-Norbornanyl)-2-quinoxalinecarboxamide (148)

Prepared from 2-quinoxaloyl chloride (193 mg, 1.0 mmol), exo-2-aminonorbornane (133 mg, 0.90 mmol), pyridine (5 mL), and water (50 mL) yielding 35 mg (15%) of (148):

rt=10.22 min.; m/z (rel. int.) 267 (M+, 36), 198 (10), 158 (7), 157 (9), 131 (7), 130 (47), 129 (78), 111 (8), 111 (8), 110 (100), 103 (16), 102 (39), 77 (5), 76 (12), 75 (11), 67 (11), 51 (7), 41 (10).

N-[(1R,2S,4S)-Bornyl]-2-quinoxalinecarboxamide (150)

Prepared from 2-quinoxaloyl chloride (193 mg, 1.0 mmol), (R)-(+)-bornylamine (138 mg, 0.90 mmol), pyridine (5 mL), and water (50 mL) yielding 140 mg (50%) of (150):

rt=10.79 min.; m/z (rel. int.) 309 (M+, 27), 199 (8), 187 (10), 174 (10), 158 (11), 157 (14), 153 (10), 152 (82), 144 (9), 135 (11), 131 (7), 130 (51), 129 (100), 109 (20), 103 (18), 102 (43), 95 (38), 93 (12), 91 (7), 79 (9), 77 (11), 76 (13), 75 (11), 67 (17), 55 (14), 53 (8), 51 (8), 43 (8), 41 (25).

N-(3-Noradamantyl)-2-quinoxalinecarboxamide (152)

Prepared from 2-quinoxaloyl chloride (193 mg, 1.0 mmol), 3-noradamantanamine (157 mg, 0.90 mmol), pyridine (5 mL), and water (50 mL) yielding 167 mg (63%) of (152):

rt=11.00 min.; m/z (rel. int.) 293 (M+, 50), 265 (12), 250 (18), 232 (6), 222 (20), 157 (12), 144 (6), 137 (7), 136 (64), 131 (6), 130 (35), 130 (35), 129 (100), 103 (19), 102 (35), 94 (15), 91 (6), 80 (6), 79 (11), 77 (11), 76 (12), 75 (9), 67 (6), 53 (6), 51 (6), 41 (13).

N-[(1R,2R,3R,5S)-Isopinocamphenyl]-2-quinoxalinecarboxamide (165)

Prepared from 2-quinoxaloyl chloride (193 mg, 1.0 mmol), (1R,2R,3R,5S)-(−)-isopinocamphenylamine (138 mg, 0.90 mmol), pyridine (5 mL), and water (50 mL) yielding 230 mg (83%) of (165):

rt=10.88 min.; m/z (rel. int.) 309 (M+, 4), 226 (19), 200 (17), 199 (5), 198 (7), 186 (9), 175 (7), 174 (16), 158 (6), 157 (14), 152 (6), 130 (42), 129 (100), 103 (16), 102 (42), 102 (42), 95 (13), 93 (10), 79 (6), 77 (7), 76 (11), 75 (9), 67 (7), 55 (12), 53 (6), 51 (5), 43 (5), 41 (18).

N-[(1S,2S,3S,5R)-Isopinocamphenyl]-2-quinoxalinecarboxamide (166)

Prepared from 2-quinoxaloyl chloride (193 mg, 1.0 mmol), (1S,2S,3S,5R)-(+)-isopinocamphenylamine (138 mg, 0.90 mmol), pyridine (5 mL), and water (50 mL) yielding 208 mg (75%) of (166):

rt=10.88 min.; m/z (rel. int.) 309 (M+, 4), 226 (16), 200 (14), 198 (7), 186 (8), 175 (6), 174 (14), 158 (5), 156 (13), 130 (42), 130 (42), 129 (100), 103 (18), 102 (46), 95 (11), 93 (10), 91 (5), 79 (5), 77 (8), 76 (12) 75 (11), 67 (8), 55 (13), 53 (6), 51 (6), 43 (6), 41 (20).

N-(5-Chlorotricyclo[2.2.1.0(2,6)]hept-3-yl)-2-quinoxalinecarboxamide (167)

Prepared from 2-quinoxaloyl chloride (193 mg, 1.0 mmol), 5-chlorotricyclo[2.2.1.0(2,6)]hept-3-ylamine (129 mg, 0.90 mmol), pyridine (5 mL), and water (50 mL) yielding 100 mg (37%) of (167):

rt=11.29 min.; m/z (rel. int.) 299 (M+, 2), 264 (76), 246 (12), 199 (7), 198 (47), 186 (16), 185 (6), 144 (6), 142 (16), 130 (30), 129 (100), 106 (15), 103 (20), 102 (55), 102 (55), 91 (24), 80 (7), 79 (18), 78 (6), 77 (18), 76 (19), 75 (19), 65 (10), 53 (6), 52 (6), 51(14), 50(7).

N-(Tricyclo[4.3.1.1(3,8)]undec-3-yl)-2-quinoxalinecarboxamide (168)

Prepared from 2-quinoxaloyl chloride (135 mg, 0.70 mmol), tricyclo[4.3.1.1(3,8)]undec-3-ylamine hydrochloride (100 mg, 0.60 mmol), pyridine (5 mL), and water (50 mL) yielding 110 mg (57%) of (168):

rt=12.52 min.; m/z (rel. int.) 321 (M+, 48), 165 (13), 164 (100), 157 (9), 131 (8), 130 (32), 130 (32), 129 (79), 107 (5), 106 (5), 105 (11), 103 (17), 102 (31), 94 (9), 93 (8), 92 (9), 91 (15), 81 (6), 80 (7), 79 (16), 77 (10), 76 (9), 75 (7), 67 (8), 55 (5), 53 (5), 41 (10).

N-[(1S,2R,5S)-cis-Myrtanyl]-2-quiinoxalinecarboxamide (169)

Prepared from 2-quinoxaloyl chloride (193 mg, 1.0 mmol), (−)-cis-myrtanylamine (138 mg, 0.90 mmol), pyridine (5 mL), and water (50 mL) yielding 224 mg (81%) of (169):

rt=11.32 min.; m/z (rel. int.) 309 (M+, 18), 186 (30), 174 (20), 158 (12), 157 (27), 152 (16), 131 (6), 130 (47), 130 (47), 129 (100), 121 (5), 103 (17), 102 (45), 93 (12), 91 (6), 81 (11), 79 (12), 77 (10), 76 (13), 75 (11), 69 (13), 67 (15), 55 (8), 54 (6), 53 (8), 51 (7), 43 (6), 41 (26).

N-[(1R,2R,4S)-Isobornyl]-2-quinoxalinecarboxamide (170)

Prepared from 2-quinoxaloyl chloride (193 mg, 1.0 mmol), (R)-(−)-isobornylamine (138 mg, 0.90 mmol), pyridine (5 mL), and water (50 mL) yielding 130 mg (81%) of (170):

rt=10.76 min.; m/z (rel. int.) 309 (M+, 24), 199 (7), 197 (6), 187 (8), 174 (8), 158 (9), 157 (12), 153 (7), 152 (58), 144 (9), 135 (8), 130 (46), 129 (100), 109 (14), 103 (21), 102 (48), 95 (31), 93 (10), 91 (7), 79 (8), 77 (10), 76 (13), 75 (12), 67 (15), 55 (12), 53 (7), 51 (6), 43 (6), 41 (18).

N-[endo-(±)-2-Norbornanyl]-2-quinoxalinecarboxamide (171)

Prepared from 2-quinoxaloyl chloride (193 mg, 1.0 mmol), endo-(±)-2-aminonorbornane (133 mg, 0.90 mmol), pyridine (5 mL), and water (50 mL) yielding 175 mg (73%) of (171):

rt=10.15 min.; m/z (rel. int.) 267 (M+, 35), 198 (11), 185 (6), 158 (7), 157 (11), 144 (5), 131 (7), 130 (55), 129 (100), 111 (6), 110 (81) 103 (24), 102 (56), 77 (7), 76 (19), 75 (17), 75 (17), 67 (13), 55 (5), 53 (7), 51 (9), 50 (5), 41 (14).

N-[(R)-2-Phenyl-1-propyl]-2-quinoxalinecarboxamide (172)

Prepared from 2-quinoxaloyl chloride (0.47 g, 2.4 mmol), (R)-2-phenyl-1-propylamine (0.30 g, 2.2 mmol), pyridine (5 mL), and water (50 mL) yielding 0.49 g (76%) of (172):

rt=10.63 min.; m/z (rel. int.) 291 (M+, 14), 186 (9), 158 (5), 157 (32), 130 (25), 129 (100), 118 (22), 105 (24), 104 (5), 103 (21), 102 (48), 91 (9), 79 (11), 78 (6), 77 (18), 76 (13), 75 (13), 75 (13), 51 (9).

N-[(S)-2-Phenyl-1-propyl]-2-quinoxalinecarboxamide (173)

Prepared from 2-quinoxaloyl chloride (0.47 g, 2.4 mmol), (S)-2-phenyl-1-propylamine (0.30 g, 2.2 mmol), pyridine (5 mL), and water (50 mL) yielding 0.48 g (74%) of (173):

rt=10.72 min.; m/z (rel. int.) 291 (M+, 13), 186 (68), 158 (5), 157 (37), 130 (21), 129 (100), 118 (29), 105 (21), 103 (16), 102 (37), 91 (7), 79 (10), 77 (15), 76 (11), 75 (10), 51 (9), 51 (9).

N-(2-Indanyl)-2-quinoxalinecarboxamide (221)

Prepared from 2-quinoxaloyl chloride (0.32 g, 1.7 mmol), 2-aminoindan (0.20 g, 1.5 mmol), pyridine (3 mL), and water (30 mL) yielding 0.23 g (53%) of (221):

rt=11.33 min.; m/z (rel. int.) 289 (M+, 10), 132 (6), 130 (28), 129 (41), 117 (15), 116 (100), 115 (37), 104 (7), 103 (26), 102 (37), 91 (7), 78 (7), 77 (13), 76 (16), 75 (14), 51 (9), 51 (9), 50 (5).

N-Cyclooctyl-2-quinoxalinecarboxamide (228)

Prepared from 2-quinoxaloyl chloride (193 mg, 1.0 mmol), cyclooctylamine (123 µL, 114 mg, 0.90 mmol), pyridine (5 mL), and water (100 mL) yielding 100 mg (39%) of (228):

rt=10.86 min.; m/z (rel. int.) 283 (M+, 27), 212 (6), 199 (9), 198 (20), 198 (20), 185 (16), 184 (6), 174 (8), 157 (15), 144 (7), 131 (6), 130 (48), 129 (100), 126 (42), -103 (20), 102 (50), 76 (13), 75 (12), 67 (6), 56 (7), 55 (9), 51 (6), 43 (6), 41 (16).

N-Cycloheptyl-2-quinoxalinecarboxamide (229)

Prepared from 2-quinoxaloyl chloride (193 mg, 1.0 mmol), cycloheptylamine (115 µL, 102 mg, 0.90 mmol), pyridine (5 mL), and water (100 mL) yielding 30 mg (12%) of (229):

rt=10.30 min.; m/z (rel. int.) 269 (M+, 39), 212 (6), 198 (20), 185 (13), 174 (14), 174 (14), 157 (20), 131 (7), 130 (49), 129 (100), 112 (44), 103 (23), 102 (51), 76 (15), 75 (13), 56 (6), 55 (8), 51 (7), 42 (5), 41 (15).

N-[2-Spiro(4.5)decyl]-2-quinoxalinecarboxamide (236)

Prepared from 2-quinoxaloyl chloride (193 mg, 1.0 mmol), 2-aminospiro(4.5)decane (150 mg, 0.79 mmol), pyridine (5 mL), and water (100 mL) yielding 206 mg (74%) of (236): rt=10.94 min.;

m/z (rel. int.) 282 (M+, 25), 199 (7), 186 (6), 157 (10), 130 (32), 129 (96), 125 (40), 110 (10), 109 (100), 108 (15), 103 (14), 102 (55), 98 (6), 97 (27), 96 (25), 84 (9), 82 (18), 76 (15), 75 (16), 70 (55), 69 (7), 68 (13), 56 (7), 55 (8), 53 (6), 51 (9), 43 (8), 42 (36), 41 (14).

Example 6

Preparation of 1-Adamantanemethyl 6-quinolyl Ether (94)

A mixture of 1-adamantanemethanol (5.00 g, 30.0 mmol) and 6-hydroxyquinoline (13.1 g, 90.2 mmol) in tetrahydrofuran (75 mL) was stirred for 15 min. Then, triphenylphosphine (10.2 g, 39.0 mmol) was added, followed by diethyl azodicarboxylate (6.14 mL, 39.0 mmol). The reaction mixture was refluxed for 18 h. The solvent was then removed by rotary evaporation. The resulting gel was filtered through paper with diethyl ether (3×25 mL). The filtrate was rotary evaporated, and the resulting gel was filtered through paper with hexanes (3×25 mL). Again the filtrate was rotary evaporated, the resulting gel was filtered through paper with hexanes (3×25 mL), and the filtrate was rotary evaporated. This provided 3.8 g (43%) of crude product as a red oil. This oil was chromatographed (2:1 hexanes/ethyl acetate) to provide 1.6 g (18%) of (94):

rt=11.29 min.; m/z (rel. int.) 293 (M+, 15), 149 (100), 145 (6), 128 (13), 121 (6), 116 (12), 116 (12), 107 (17), 93 (29), 91 (18), 89 (10), 81 (16), 79 (25), 77 (17), 67 (14), 65 (5), 55 (8), 53 (6), 41 (14).

Example 7

Preparation of 1-Adamantyl 3-quinolinecarboxylate (101)

A mixture of 1-adamantanol (152 mg, 1.0 mmol), 3-quinolinecarboxylic acid (173 mg, 1.0 mmol), and dimethylaminopyridine (122 mg, 1.0 mmol) in dichloromethane (2 mL) and N,N-dimethylformamide (2 mL) was cooled to 0° C. 1,3-Dicyclohexylcarbodiimide (227 mg, 1.1 mmol) in dichloromethane (1 mL) was added in one portion. The reaction mixture was stirred at 25° C. for 20 h. The reaction mixture was then diluted with dichloromethane (40 mL) and washed with 1 M sodium hydroxide (3×30 mL). The organic layer was dried (anhydrous magnesium sulfate), filtered through Celite, and rotary evaporated. The resulting material was purified by spinning thin-layer chromatography (3% methanol in chloroform). The purest fraction was rotary evaporated, and the resulting material was recrystallized from ethanol. This provided 42 mg (14%) of (101):

rt=7.78 min.; m/z (rel. int.) 307 (M+, 96), 306 (100), 173 (11), 155 (38), 135 (6), 127 (55), 119 (6), 106 (9), 100 (23), 93 (25), 92 (33), 91 (14), 78 (23), 77 (6), 76 (13), 74 (8), 67 (9), 54 (7), 41 (12).

Example 8

Preparation of N-(α,α-Dimethylphenethyl)-2-quinoxalinecarboxamide (108)

2-Quinoxaloyl chloride (207 mg, 1.07 mmol) in dichloromethane (1 mL) was added to a solution of phentermine (160 mg, 1.07 mmol) in dichloromethane (3 mL) cooled to 0° C. The reaction was allowed to warm to 25° C. After 5 min, the reaction mixture was diluted with ethyl acetate (40 mL) and washed with 1 M sodium hydroxide (2×40 mL). The organic layer was dried (anhydrous magnesium sulfate), filtered through silica gel, and rotary evaporated. This provided 51 mg (16%) of (108):

rt=9.31 min.; m/z (rel. int.) 305 (M+, 0.0), 214 (96), 186 (30), 157 (16), 130 (22), 129 (100), 103 (10), 102 (31), 92 (4), 91 (47), 76 (5), 75 (5), 65 (10).

N-(2-Chlorobenzyl)-2,4,6-triphenylpyridinium Tetrafluoroborate

2-Chlorobenzylamine (2.0 g, 14 mmol) was added dropwise to a suspension of 2,4,6-triphenylpyrylium tetrafluoroborate (5.1 g, 13 mmol) in dichloromethane (40 mL). The reaction mixture was stirred for 16 h. Ethanol (4 mL) and excess diethyl ether were added to precipitate the product. The precipitate was filtered and dried. This provided 6.14 g (92%) of N-(2-chlorobenzyl)-2,4,6-triphenylpyridinium tetrafluoroborate.

1-(2-Chlorophenyl)-2-methyl-2-nitropropane

2-Nitropropane (3.19 mL, 35.5 mmol) was added to a mixture of sodium hydride (0.85 g, 35 mmol) in methanol (15 mL) cooled to 0° C. The reaction mixture was then stirred and allowed to warm to 25° C. for 10 min. The solvent was rotary evaporated to provide a white solid. A mixture of this solid and N-(2-chlorobenzyl)-2,4,6-triphenylpyridinium tetrafluoroborate (6.14 g, 11.8 mmol) in dimethyl sulfoxide (45 mL) was stirred under nitrogen gas for 16 h. Water was then added to quench the reaction. This mixture was then extracted with diethyl ether (3×100 mL). The organic layer was washed with saturated aqueous sodium chloride, dried (anhydrous sodium sulfate), and filtered. The filtrate was stirred in strongly acidic Amberlyst 15 ion-exchange resin (1 g/mmol) for 4 h. The reaction mixture was filtered and rotary evaporated. This provided 2.35 g (93%) of 1-(2-chlorophenyl)-2-methyl-2-nitropropane.

α,α-Dimethyl-2-chlorophenethylamine

A mixture of Raney nickel (50% by weight in water; 2.3 g) and 1-(2-chlorophenyl)-2-methyl-2-nitropropane (2.35 g, 11 mmol) in ethanol (35 mL) was shaken under hydrogen gas (60 psig) for 3.5 h. The reaction mixture was then filtered, and the filtrate was rotary evaporated. This provided 2.3 g (110%) of α,α-dimethyl-2-chlorophenethylamine.

N-(α,α-Dimethyl-2-chlorophenethyl)-2-quinoxalinecarboxamide (197)

In a similar manner to (108), (197) was prepared from 2-quinoxaloyl chloride (158 mg, 0.82 mmol), α,α-dimethyl-2-chlorophenethylamine (151 mg, 0.82 mmol), and dichloromethane (3 mL) yielding 196 mg (70%) of (197):

rt=10.04 min.; m/z (rel. int.) 339 (M+, 0.0), 213 (58), 186 (24), 156 (12), 129 (25), 128 (100), 126 (14), 124 (44), 102 (14), 101 (38), 98 (5), 90 (5), 88 (18), 75 (10), 75 (10), 75 (9), 62 (5), 50 (5), 41 (9).

Example 9

Preparation of N-(α,α-Dimethyl-4-fluorophenethyl)-2-quinoxalinecarboxamide (129)

To a solution of 1-(4-fluorophenyl)-2-methyl-2-propylamine (105 mg, 0.628 mmol) in pyridine (2 mL) was added 2-quinoxaloyl chloride (133 mg, 0.691 mmol). The reaction was then stirred for 30 min. To the stirring reaction mixture was added water (20 mL) which caused the product to separate as an oil. This mixture was extracted with ethyl acetate (1×10 mL), washed with water (2×5 mL), dried (anhydrous magnesium sulfate), rotary evaporated, and put under high vacuum for 15 h. This provided 146 mg (71.9%) of (129):

rt=10.45 min.; m/z (rel. int.) 323 (M+, 0.1), 214 (73), 186 (22), 157 (14), 135 (4), 130 (19), 129 (100), 109 (22), 103 (9), 102 (30), 83 (7), 76 (9), 75 (8), 42 (6).

In a similar manner, the following N-substituted 2-quinoxalinecarboxamides were prepared:

N-(β-Methylphenethyl)-2-quinoxalinecarboxamide (131)

Prepared from 2-quinoxaloyl chloride (193 mg, 0.84 mmol), β-methylphenethylamine (103 mg, 0.76 mmol), and pyridine (2 mL) yielding 154 mg (69%) of (131):

rt=10.71 min.; m/z (rel. int.) 291 (M+, 12), 186 (66), 158 (5), 157 (37), 130 (20), 129 (100), 118 (28), 105 (21), 103

(17), 102 (37), 91 (7), 79 (10), 78 (5), 77 (15), 76 (11), 75 (10), 51(10), 51(10).

N-(3-Methylcyclohexyl)-2-quinoxalinecarboxamide (161)

Prepared from 2-quinoxaloyl chloride (193 mg, 1.0 mmol), 3-methylcyclohexylamine (119 mg, 0.90 mmol), and pyridine (5 mL) yielding 190 mg (78%) of (161):

rt=9.99 min.; m/z (rel. int.) 269 (M+, 37), 226 (6),-198 (11), 174 (23), 157 (23), 131 (7), 130 (44), 129 (100), 113 (5), 112 (59), 103 (20), 102 (41), 95 (5), 81 (6), 76 (15), 75 (12), 56 (5), 55 (9), 51 (7), 41 (15), 41 (15).

N-(2,3-Dimethylcyclohexyl)-2-quinoxalinecarboxamide (163)

Prepared from 2-quinoxaloyl chloride (193 mg, 1.0 mmol), 2,3-dimethylcyclohexylamine (115 mg, 0.90 mmol), and pyridine (5 mL) yielding 150 mg (59%) of (163): rt=10.12 min.; m/z (rel. int.) 283 (M+, 35), 212 (6), 198 (14), 175 (6), 174 (39), 158 (7), 157 (22), 131 (6), 130 (46), 129 (100), 126 (44), 109 (8), 103 (20), 103 (20), 102 (45), 76 (13), 75 (11), 67 (7), 56 (10), 55 (12), 51 (6), 43 (6), 41 (16).

N-[(1S,2S,3S,5R)-3-Pinanemethyl]-2-quinoxalinecarboxamide (207)

Prepared from 2-quinoxaloyl chloride (193 mg, 1.0 mmol), (+)-3-pinanemethylamine (150 mg, 0.90 mmol), and pyridine (5 mL) yielding 229 mg (79%) of (207):

rt=12.07 min.; m/z (rel. int.) 323 (M+, 12), 187 (100), 186 (12), 174 (33), 166 (24), 159 (8), 158 (66), 157 (26), 150 (9), 144 (7), 131 (11), 130 (80), 129 (85), 107 (10), 103 (14), 102 (31), 95 (22), 93 (11), 91 (8), 83 (7), 81 (11), 79 (11), 77 (8), 76 (8), 69 (8), 67 (13), 55 (17), 43 (9), 41 (25).

Example 10

N-(1-Adamantanemethyl)-2-quinoxalinecarboxamide (146)

2-Quinoxaloyl chloride (429 mg, 2.6 mmol) was added to a solution of 1-adamantanemethylamine (500 mg, 2.6 mmol) in chloroform (5 mL). The reaction mixture was heated until everything had dissolved. The reaction mixture was stirred at 25° C. for 1 h. To the stirring reaction mixture was added water (100 mL) which caused the product to precipitate. The precipitate was filtered, washed with water (2×), and dried under high vacuum. This provided 375 mg (45%) of (146):

rt=12.27 min.; m/z (rel. int.) 321 (M+, 101), 186 (7), 174 (6), 164 (34), 158 (6), 157 (8), 136 (11), 135 (100), 131 (7), 130 (46), 129 (75), 107 (23), 105 (6), 103 (20), 102 (53), 93 (44), 92 (6), 91 (23), 81 (13), 79 (47), 77 (24), 76 (16), 75 (13), 67 (16), 65 (6), 55 (9), 53 (8), 51 (8), 41 (13).

Example 11

Preparation of N-(4-Methylcyclohexyl)-2-quinoxalinecarboxamide (162)

To a solution of 4-methylcyclohexylamine (119 mg, 0.90 mmol) in pyridine (2 mL) was added 2-quinoxaloyl chloride (193 mg, 1.0 mmol). The reaction was then stirred for 1 h. To the stirring reaction mixture was added water (20 mL) which caused the product to precipitate as an oil. This mixture was extracted with 30% dichloromethane in diethyl ether (2×25 mL), washed with water (2×25 mL), dried (anhydrous sodium sulfate), and rotary evaporated. This provided 123 mg (51%) of (162):

rt=10.00 min.; m/z (rel. int.) 269 (M+, 53), 212 (15), 212 (15), 198 (7), 174 (25), 158 (6), 157 (36), 131 (7), 130 (44), 129 (100), 113 (6), 112 (66), 103 (18), 102 (36), 95 (9), 81 (6), 76 (12), 75 (9), 56 (5), 55 (10), 51 (6), 41 (12).

Example 12

Preparation of N-[(1S,2S,5S)-trans-Myrtanyl]-2-quinoxalinecarboxamide (225)

(1S,2S,5S)-trans-Myrtanyl Trifluoroacetate

Trifluoroacetic anhydride (5.50 mL, 39.0 mmol) was added to (−)-trans-myrtanol (5.10 mL, 32.5 mmol) in dry tetrahydrofuran (100 mL). This reaction mixture was stirred for 1 h. The reaction mixture was rotary evaporated. This provided 7.60 g (94%) of (1S,2S,5S)-trans-myrtanyl trifluoroacetate.

(1R,2R,5R)-trans-Myrtanyl Trifluoroacetate

In a similar manner, (1R,2R,5R)-trans-myrtanyl trifluoroacetate was prepared from trifluoroacetic anhydride (5.40 mL, 38.0 mmol, 1.2 equiv) (+)-trans-myrtanol (5.00 mL, 4.90 g, 31.7 mmol), and tetrahydrofuran (100 mL) yielding 7.60 g (94%) of (1R,2R,5R)-trans-myrtanyl trifluoroacetate.

(1S,2S,5S)-trans-Myrtanylazide

A mixture of (1S,2S,5S)-trans-myrtanyl trifluoroacetate (1.0 g, 4.0 mmol), sodium azide (0.39 g, 6.0 mmol), and N,N-dimethylformamide (50 mL) was stirred at 80° C. for 24 h. After cooling to 25° C., water (100 mL) was added, and this mixture was extracted with diethyl ether (2×50 mL). The organic layer was then dried (anhydrous sodium sulfate) and rotary evaporated. This provided 1.12 g (100%) of (1S,2S,5S)-trans-myrtanylazide as a colorless oil.

(1R,2R,5R)-trans-Myrtanylazide

In a similar manner, (1R,2R,5R)-trans-myrtanylazide was prepared from (1R,2R,5R)-trans-myrtanyl trifluoroacetate (7.60 g, 30.4 mmol), sodium azide (3.00 g, 45.6 mmol), and N,N-dimethylformamide (100 mL) yielding 4.10 g (48.2%) of (1R,2R,5R)-trans-myrtanylazide.

(1S,2S,5S)-trans-Myrtanylamine

A mixture of (1S,2S,5S)-trans-myrtanylazide (1.12 g, 7.32 mmol) and platinum(IV) oxide hydrate (0.34 g) in ethanol (50 mL) was shaken under hydrogen gas (50 psig) for 2 h. The reaction mixture was then filtered through paper, and the filtrate was rotary evaporated. The resulting material was taken up in 0.12 M hydrochloric acid (100 mL), and the aqueous solution was washed with diethyl ether (2×50 mL). The aqueous layer was made basic with 0.1 M sodium hydroxide (50 mL) and extracted with dichloromethane (2×50 mL). The organic layer was then dried (anhydrous sodium sulfate) and rotary evaporated. This provided 78 mg (7%) of (1S,2S,5S)-trans-myrtanylamine as a light yellow oil.

(1R,2R,5R)-trans-Myrtanylamine

In a similar manner, (1R,2R,5R)-trans-myrtanylamine was prepared from (1R,2R,5R)-trans-myrtanylazide (4.10 g, 26.8 mmol), platinum(IV) oxide hydrate (0.41 g), and ethanol (75 mL) yielding 2.00 g (48.8%) of (1R,2R,5R)-trans-myrtanylamine.

N-[(1S,2S,5S)-trans-Myrtanyl]-2-quinoxalinecarboxamide (225)

In a similar manner to (162), (225) was prepared from 2-quinoxaloyl chloride (49 mg, 0.25 mmol), (1S,2S,5S)-trans-myrtanylamine (35 mg, 0.23 mmol), and pyridine (5 mL) yielding 8 mg (10%) of (225):

rt=11.23 min.; m/z (rel. int.) 309 (M+, 25), 187 (15), 186 (39), 174 (12), 158 (14), 157 (29), 152 (20), 131 (6), 130

(47), 130 (47), 129 (100), 103 (15), 102 (41), 93 (9), 91 (6), 81 (12), 79 (12), 77 (9), 76 (11), 75 (10), 69 (14), 67 (17), 55 (8), 54 (5), 53 (7), 51 (7), 43 (6), 41 (25).

N-[(1R,2R,5R)-trans-Myrtanyl]-2-quinoxalinecarboxamide (226)

In a similar manner, (226) was prepared from 2-quinoxaloyl chloride (193 mg, 1.0 mmol), (1R,2R,5R)-trans-myrtanylamine (138 mg, 0.90 mmol), and pyridine (5 mL) yielding 27 mg (10%) of (226):

rt=11.19 min.; m/z (rel. int.) 309 (M+, 21), 186 (47), 186 (18), 174 (17), 158 (16), 157 (34), 152 (30), 131 (6), 130 (47), 130 (47), 129 (100), 121 (6), 103 (15), 102 (40), 93 (11), 91 (6), 81 (12), 79 (11), 77 (8), 76 (10), 75 (9), 69 (14), 67 (17), 55 (7), 53 (6), 51 (5), 43 (5), 41 (18).

Example 13

Preparation of N-[N'-(R)-α-Methylbenzyl-2-acetamido]-3-aminoquinoline dihydrochloride (156)

N-(R)-α-Methylbenzyl-2-chloroacetamide (R)-α-Methylbenzylamine (2.4 g, 20 mmol) in dichloromethane (50 mL) was added to chloroacetyl chloride (2.25 g, 20 mmol) in dichloromethane (70 mL) and pyridine (10 mL). The reaction solution was stirred, then diluted with diethyl ether (500 mL), washed with water (3×30 mL), dried (anhydrous magnesium sulfate), and rotary evaporated. This provided 3.60 g of N-(R)-α-methylbenzyl-2-chloroacetamide.

N-(R)-α-Methylbenzyl-2-iodoacetamide

A solution of sodium iodide (10.37 g, 69 mmol) in dry acetone was slowly added to a solution of N-(R)-α-methylbenzyl-2-chloroacetamide (3.39 g, 17 mmol) in dry acetone, and the reaction mixture was refluxed for 16 h. The reaction mixture was then filtered, and the filtrate was rotary evaporated. Diethyl ether was added, and the mixture was stirred for 20 min. The mixture was then filtered, and the filtrate was rotary evaporated and then put under high vacuum to provide N-(R)-α-methylbenzyl-2-iodoacetamide.

N-[N'-(R)-α-Methylbenzyl-2-acetamido]-3-aminoquinoline Dihydrochloride (156)

A mixture of 3-aminoquinoline (0.15 g, 1.0 mmol) and potassium fluoride on Celite (50%) (0.30 g, 2.5 mmol) in acetonitrile (20 mL) was stirred for 1 h. N-(R)-α-Methylbenzyl-2-iodoacetamide (0.31 g, 1.0 mmol) in acetonitrile was added, and the reaction mixture was refluxed for 64 h. The mixture was filtered, and the filtrate was rotary evaporated. The resulting material was taken up in diethyl ether and washed with 1 M sodium hydroxide (3×30 mL). The combined aqueous layers were saturated with sodium chloride and were then extracted with chloroform (4×). The combined organic layer were dried (anhydrous magnesium sulfate) and rotary evaporated. The resulting material was dissolved in chloroform (10 mL), 1 M hydrogen chloride in diethyl ether (5 mL) was added, and the solution was rotary evaporated. The resulting material was dissolved in chloroform (5 mL) and filtered through a 0.45 μm filter 10 disc, and the filtrate was evaporated. This provided 13 mg (3%) of (156):

rt=10.43 min.; m/z (rel. int.) 328 (M+, 11), 182 (12), 181-(86), 180 (37), 167 (22), 166 (25), 165 (17), 162 (53), 161 (95), 160 (37), 148 (32), 145 (18), 135 (21), 132 (16), 122 (9), 120 (22), 119 (20), 107 (19), 106 (13), 105 (100), 104 (22), 103 (19), 90 (12), 79 (25), 78 (11), 77 (38), 51 (10), 41 (11).

Example 14

Preparation of 1-(1-Adamantyl)-2-(benzothiazol-2-ylsulfanyl)ethanone (273)

Sodium hydride (36.5 mg, 1.52 mmol, 60% in mineral oil) was washed with pentane (4×), dried under $N_2$, suspended in dimethylformamide (DMF, 10 mL) and cooled to 0° C. With stirring, a solution of 2-mercaptobenzothiazole (253.3 mg, 1.52 mmol) in DMF (5 mL) was added dropwise. The reaction was stirred 20 minutes at 0° C. and treated with a solution of 1-adamantanebromomethyl ketone (389.8 mg, 1.52 mmol) in DMF (8 mL). The reaction was stirred 30 minutes at ambient temperature and diluted with diethyl ether (100 mL). The resulting solution was washed with water (5×30 mL) and the remaining organic solution dried over anhydrous $MgSO_4$, filtered, and concentrated to a solid. Recrystallization from hot ethanol afforded 287 mg (55%) of the desired product: GC/EI-MS gave m/z (rel. int.) 343 (M+, 10), 315 (2), 180 (2), 148 (10), 135 (100), 107 (9), 93 (17), and 79 (20).

Example 15

Preparation of N-(trans-4-methylcyclohexyl)quinoline-4-carboxamide (403)

A solution of quinoline-4-carboxylic acid (173 mg, 1 mmol), and 1,1'-carbonyldiimidazole (162 mg, 1 mmol) in dimethylformamide (2 mL) was heated at 50° C. for 1 hour. After this time, trans-4-methylcyclohexylamine hydrochloride (150 mg, 1 mmol), and N,N-diisopropylethylamine (0.262 mL, 1.5 mmol) were added and the mixture heated at 50° C. for 16 hours. The reaction mixture was cooled, and diluted with chloroform (10 mL). The organic solution was washed with water (3×10 mL), 1 N NaOH (10 mL), brine (10 mL), dried over anhydrous $MgSO_4$, filtered and concentrated to afford 156 mg (58%) of 403:

rt=10.0 min.; m/z (rel. int.) 268 (M+, 30), 211 (4) 173 (100), 156 (71), 128 (74), 101 (26).

Example 16

Preparation of N-(trans-4-methylcyclohexyl)quinoline-8 carboxamide (404)

A solution of quinoline-4-carboxylic acid (173 mg, 1 mmol), and 1,1'-carbonyldiimidazole (162 mg, 1 mmol) in dimethylformamide (2 mL) was heated at 50° C. for 1 hour. After this time, trans-4-methylcyclohexylamine hydrochloride (150 mg, 1 mmol), and N,N-diisopropylethylamine (0.262 mL, 1.5 mmol) were added and the mixture heated at 50° C. for 16 hours. The reaction mixture was cooled, and diluted with chloroform (10 mL). The organic solution was washed with water (3×10 mL), 1 N NaOH (10 mL), brine (10 mL), dried over anhydrous $MgSO_4$, filtered and concentrated to afford 224 mg (84%) of 404:

rt=10.2 min.; m/z (rel. int.) 268 (M+, 24), 267 (26), 211 (9) 173 (14), 156 (100), 129 (47), 112 (26).

Example 17

Preparation of
N-(trans-4-methylcyclohexyl)isoquinoline
1-carboxamide (405)

A solution of isoquinoline-1-carboxylic acid (346 mg, 2 mmol), and 1,1'-carbonyldiimidazole (325 mg, 2 mmol) in dimethylformamide (4 mL) was heated 3 o at 50° C. for 1 hour. After this time, trans-4-methylcyclohexylamine hydrochloride (300 mg, 2 mmol), and N,N-diisopropylethylamine (0.523 mL, 3 mmol) were added and the mixture heated at 50° C. for 16 hours. The reaction mixture was cooled, and diluted with ethyl acetate (20 mL). The organic solution was washed with water (3×15 mL), brine (20 mL), dried over anhydrous $MgSO_4$, filtered and concentrated to afford 429 mg (80%) of 405:

rt=9.19 min.; m/z (rel. int.) 268 ($M^+$, 24), 211 (18), 197 (16), 173 (1), 156 (23), 128 (100), 112 (64).

Example 18

Preparation of N-(trans-4-methylcyclohexyl)iso-
quinoline-3-carboxamide (406)

A solution of isoquinoline-3-carboxylic acid (346 mg, 2 mmol), and 1,1'-carbonyldiimidazole (325 mg, 2 mmol) in dimethylformamide (4 mL) was heated at 50° C. for 1 hour. After this time, trans-4-methylcyclohexylamine hydrochloride (300 mg, 2 mmol), and N,N-diisopropylethylamine (0.523 mL, 3 mmol) were added and the mixture heated at 50° C. for 16 hours. The reaction mixture was cooled, and diluted with ethyl acetate (20 mL). The organic solution was washed with water (3×15 mL), brine (20 mL), dried over anhydrous $MgSO_4$, filtered and concentrated to afford 377 mg (70%) of 406:

rt=9.65 min.; m/z (rel. int.) 268 ($M^+$, 9), 240 (6), 223 (16), 211 (17), 197 (13), 173 (22), 156 (55), 128 (100), 112 (38), 101 (15), 77 (10).

Example 19

Preparation of
N-(3-quinolinyl)quinoxaline-2-carboxamide
Hydrochloride (407)

A solution of 2-quinoxaloyl chloride (193 mg, 1 mmol) in dichloromethane (20 mL) was treated with trans-4-methylcyclohexylamine hydrochloride (150 mg, 1 mmol), and pyridine (0.2 mL) and stirred at ambient temperature for 60 min. After this time the reaction mixture was diluted with diethyl ether (50 mL). The organic solution was washed with 1 N NaOH (2×10 mL), brine (20 mL), dried over anhydrous $MgSO_4$. Treatment with excess 1 M HCl in diethyl ether afforded 331 mg (98%) of 407:

rt=12.61 min.; m/z (rel. int.) 300 ($M^+$, 43), 271 (49), 245 (7), 171 (14), 129 (100), 116 (20), 102 (48), 89 (26), 76 (16).

Example 20

Preparation of N-(trans-4-methylcyclohexyl)-6-(1-
pyrazole)nicotinamide (408)

A solution of 6-(1-pyrazole)nicotinic acid (96 mg, 0.51 mmol), and 1,1'-carbonyldiimidazole (83 mg, 0.51 mmol) in dimethylformamide (2 mL) was heated at 50° C. for 1 hour. After this time, trans-4-methylcyclohexylamine hydrochloride (76 mg, 0.51 mmol), and N,N-diisopropylethylamine (0.135 mL, 0.77 mmol) were added and the mixture heated at 50° C. for 16 hours. The reaction mixture was cooled, and diluted with chloroform (10 mL). The organic solution was washed with water (4×10 mL), brine (10 mL), dried over anhydrous $MgSO_4$, filtered and concentrated to afford 75 mg (52%) of 408:

rt=10.5 min.; m/z (rel. int.) 284 ($M^+$, 18), 189 (48), 172 (100), 144 (13), 117 (23), 90 (10).

Example 21

Preparation of
N-(trans-4-methylcyclohexyl)-6-bromopicolinamide
(409)

A solution of 6-bromopicolinic acid acid (3 g, 14.85 mmol), and 1,1'-carbonyldiimidazole (2.41 g, 14.85 mmol) in dimethylformamide (30 mL) was heated at 50° C. for 2 hours. After this time, trans-4-methylcyclohexylamine hydrochloride (2.2 g, 14.85 mmol), and N,N-diisopropylethylamine (3.88 mL, 22.3 mmol) were added and the mixture heated at 50° C. for 16 hours. The reaction mixture was cooled, and diluted with ethyl acetate (300 mL). The organic solution was washed with water (4×300 mL). The aqueous extracts were washed with ethyl acetate (2×250 mL). The combined organic extracts were dried over anhydrous $MgSO_4$, filtered and concentrated. Chromatography of the crude product through a Biotage silica cartridge (15×4 cm i.d.) using ethyl acetate-hexane (1:3, containing 1% diethylamine) afforded 3.84 g (87%) of 409:

rt=8.36 min.; m/z (rel. int.) 298 ($M^+$, 10), 296 (M+, 10), 239 (28), 241 (28), 201 (38), 203 (38), 184 (44), 186 (44), 158 (47), 156 (47), 112 (100).

Example 22

Preparation of N-(trans-4-methylcyclohexyl)-6-
(phenoxy)picolinamide (410)

A nitrogen purged mixture of N-(trans-4-methylcyclohexyl)-6-bromo picolinamide (446 mg, 1.5 mmol), sodium phenoxide (209 mg, 1.8 mmol), and [1,1'-bis(diphenylphosphino)ferrocene]dichloropalldium(II) (1:1 complex with dichloromethane; 83 mg, 0.1 mmol) in toluene-tetrahydrofuran (9:1, 5 mL) was treated with bis(dibenzylideneacetone)palladium(II) (86 mg, 0.15 mmol) and the mixture heated at reflux overnight. After this time the reaction mixture was diluted with ethyl acetate (25 mL) and filtered. The organic solution was washed with water (2×20 mL), brine, dried over anhydrous $MgSO_4$, filtered and concentrated. Chromatography of the crude product on silica (2 mm, chromatotron) with ethyl acetate-hexane (1:3, containing 1% diethylamine) afforded 97 mg (21%) of 410:

rt=8.36 min.; m/z (rel. int.) 310 ($M^+$, 31), 265 (M+, 33), 253 (28), 239 (6), 215 (30), 198 (33), 185 (16), 170 (100), 112 (75), 77 (47).

Example 23

Preparation of
N-(adamantyl)-5-(1-piperidine)nicotinamide (411)

In a sealed tube, a solution of N-(adamantyl)-5-bromonicotinamide (335 mg 1 mmol), piperidine (2 mL), and 1,8-diazabicyclo[5.4.0]undec-7-ene (1 mL, 6.7 mmol) was heated at 200° C. for 5 days. Workup and chromatography through a Biotage silica cartridge (8×4 cm i.d.) using a gradient of chloroform to 5% methanol in chloroform afforded 10 mg (3%) of 411:

rt=12.8 min.; m/z (rel. int.) 339 (M+, 100), 298 (3), 282 (15), 204 (10), 189 (12), 161 (15).

Example 24

Preparation of N-(trans-4-methylcyclohexyl) benzothiazole-2-carboxamide (412)

Using the method of Skraup (Chem. Ber., 1922, 55, 1089–1090), a solution of potassium permaganate (4.75 g, 30 mmol) in water (100 mL) was treated with 2-methylbenzothiazole (2.2 g, 15 mmol) and the mixture heated at reflux for 2.5 hours. After this time the reaction was filtered hot and the filtrate allowed to cool. The solution was then extracted once with diethyl ether (200 mL) and the remaining aqueous phase acidified (pH 1) by the addition of concentrated HCl. The aqueous phase was then extracted with dichloromethane (1×200 mL, 2×100 mL). The combined organic extracts were dried over anhydrous $MgSO_4$, filtered and concentrated to afford 400 mg (15%) of benzothiazole-2-carboxylic acid.

A solution of benzothiazole-2-carboxylic acid (359 mg, 2 mmol), and 1,1'-carbonyldiimidazole (325 mg, 2 mmol) in dimethylformamide (4 mL) was heated at 50° C. for 1 hour. After this time, trans-4-methylcyclohexylamine hydrochloride (300 mg, 2 mmol), and N,N-diisopropylethylamine (0.525 mL, 3 mmol) were added and the mixture heated at 50° C. for 3 hours. The reaction mixture was cooled, and treated with 10% HCl (15 mL). The solution was extracted with ethyl acetate (15 mL). The ethyl acetate extract was then washed with 10% HCl (15 mL), water (15 mL), and brine (15 mL). Dilution of the remaining solution with ethyl acetate (50 mL) and cooling to −20° C. afforded 25 mg (5%) 412:

rt=9.62 min.; m/z (rel. int.) 274 (M+, 43), 229 (8), 217 (29), 203 (18), 179 (29), 162 (100), 135 (69), 134 (67), 112 (53).

Example 25

Preparation of N-[2-(2,3-difluorophenyl)ethyl]quinoxaline-2-carboxamide (413)

Preparation of 2,3-difluorophenylethylamine 2,3-Difluorobenzyl bromide (5 g, 24.2 mmol) in acetonitrile (20 mL) was treated with 18-crown-6 (638 mg, 2.4 mmol) and potassium cyanide (5 g, 77 mmol). The reaction was heated at reflux for 5.5 hours. The reaction was diluted with diethyl ether (100 mL). The resulting organic solution was washed with 1 N NaOH (3×25 mL), dried over anhydrous $MgSO_4$, filtered, and concentrated to afford 3.71 g of crude 2,3-difluorobenzyl cyanide.

Without further purification, 1 g of the crude nitrile was treated with borane-tetrahydrofuran complex (20 mL of 1 M) and heated at reflux for 1 hour. After this time the reaction mixture was cooled in an ice bath and treated dropwise with 10% HCl (10 mL) followed by concentrated HCl (10 mL). The mixture was heated-at reflux for 30 min and poured over ice. The mixture was basified by the addition of 10 N NaOH (30 mL). The mixture was equilibrated with diethyl ether (300 mL) and the aqueous phase removed. The organic solution was then extracted with 10% HCl (3×100 mL). The combined aqueous extracts were basified using 10 N NaOH. The resulting basic solution was equilibrated with diethyl ether. The orangic extract was separated, dried over anhydrous $MgSO_4$, filtered, and concentrated to afford crude product. Kugelrohr distillation yielded 424 mg (41% from 2,3-difluorobenzyl bromide) of 2,3-difluorophenylethylamine:

rt=4.55 min.; m/z (rel. int.) 156 (M−1, 8), 140 (7), 135 (7), 127 (100), 109 (22), 107 (31), 101 (50), 81 (16), 77 (15), 75 (22).

N-[2-(2,3-difluorophenyl)ethyl]quinoxaline-2-arboxamide (413)

A solution of 2,3-difluorophenylethylamine (212 mg, 1.35 mmol) in dichloromethane (100 mL) was treated with 2-quinoxaloyl chloride (260 mg, 1.35 mmol), followed by pyridine (2 mL), followed by triethylamine (0.5 mL). The reaction was stirred 1 hour and diluted with diethyl ether (300 mL). The organic solution was washed with 10% HCl (4×100 mL), 1 N NaOH (4×100 mL), brine, dried over anhydrous $MgSO_4$, filtered and concentrated to solid. Chromatography through a Biotage silica cartridge (8×4 cm i.d.) using a gradient of hexane to 25% ethyl acetate (in hexane) afforded 209 mg (49%) of 413:

rt=10.08 min.; m/z (rel. int.) 313 (M+, 25), 186 (67), 157 (33), 129 (100), 102 (36), 75 (11), 51 (5).

Example 26

Preparation of N-[2-(2,4-difluorophenyl)ethyl]quinoxaline-2-carboxamide (414)

Preparation of 2,4-difluorophenylethylamine 2,4-Difluorophenylacetic acid (5 g, 29 mmol) in thionyl chloride (50 mL) was heated at reflux for 10 min and the excess thionyl chloride removed by distillation. The acid chloride in dichloromethane (10 mL) was added to a cooled (−78° C.) solution of $NH_3$ (20 mL) in dichloromethane (250 mL). Triethylamine (40 mL) was added and the reaction stirred at ambient temperature for 60 min. The solvents were then evaporated and the remaining solid dissolved in diethyl ether (500 mL). The organic solution was washed with 10% HCl (4×100 mL), 1 N NaOH (4×100 mL), dried over anhydrous $MgSO_4$, filtered and concentrated to afford 630 mg (13%) of 2,4-difluorophenylacetamide.

Without further purification, the crude amide (630 mg) in tetrahydrofuran (100 mL) was treated with borane-tetrahydrofuran complex (10 mL of 1 M) and heated at reflux for 16 hours. After this time the reaction mixture was cooled in an ice bath and treated dropwise with 10% HCl (10 mL) followed by concentrated HCl (10 mL). The mixture was heated at reflux for 30 min, cooled, and basified by the addition of 10 N NaOH (30 mL). The mixture was equilibrated with diethyl ether (50 mL) and the aqueous phase removed. The organic solution was then extracted with 10% HCl (4×50 mL). The combined aqueous extracts were basified using 10 N NaOH. The resulting basic solution was equilibrated with diethyl ether (50 mL). The orangic extract was separated, dried over anhydrous $MgSO_4$, filtered, and concentrated to afford 147 mg (25%) of 2,4-difluorophenylethylamine.

rt=4.27 min.; m/z (rel. int.) 157 (M+, 10), 140 (7), 135 (9), 127 (100), 109 (23), 107 (31), 101 (47), 81 (16), 77 (13), 75 (17).

N-[2-(2,4-difluorophenyl)ethyl]quinoxaline-2-carboxamide (414)

A solution of 2,4-difluorophenylethylamine (147 mg, 0.94 mmol) in dichloromethane (50 mL) was treated with 2-quinoxaloyl chloride (192 mg, 1 mmol), followed by pyridine (2 mL), followed by triethylamine (0.5 mL). The reaction was stirred 1 hour and diluted with diethyl ether (300 mL). The organic solution was washed with 10% HCl (4×100 mL), 1 N NaOH (4×100 mL), brine, dried over anhydrous MgSO$_4$, filtered and concentrated to solid. Chromatography through a Biotage silica cartridge (8×4 cm i.d.) using a gradient of hexane to 20% ethyl acetate (in hexane) afforded 95 mg (32%) of 414:

rt=9.41 min.; m/z (rel. int.) 313 (M$^+$, 12), 256 (2), 186 (43), 157 (31), 140 (36), 129 (100), 102 (35), 75 (11), 51 (6).

In a similar manner, the following substituted N-[2-(difluorophenyl)ethyl]quinoxaline-2-carboxamides were prepared:

Example 27

Preparation of N-[2-(2,5-difluorophenyl)ethyl]quinoxaline-2-carboxamide (415)

2,5-Difluorophenylacetic acid (5 g, 29 mmol) yielded 987 mg (48%) of 2,5-difluorophenylethylamine. 2,5-Difluorophenylethylamine (314 mg, 2 mmol), and 2-quinoxaloyl chloride (384 mg, 2 mmol) afforded 411 mg (66%) of 415:

rt=9.49 min.; m/z (rel. int.) 313 (M$^+$, 25), 256 (3), 186 (47), 157 (33), 140 (25), 129 (100), 102 (35), 75 (11).

Example 28

Preparation of N-[2-(2,6-difluorophenyl)ethyl]quinoxaline-2-carboxamide (416)

2,6-Difluorophenylacetic acid (5 g, 29 mmol) yielded 744 mg (68%) of 2,5-difluorophenylethylamine. 2,6-Difluorophenylethylamine (314 mg, 2 mmol), and 2-quinoxaloyl chloride (384 mg, 2 mmol) afforded 481 mg (77%) of 416:

rt=9.48 min.; m/z (rel. int.) 313 (M$^+$, 21), 256 (1), 186 (59), 157 (32), 140 (10), 129 (100), 102 (33), 75 (10).

Example 29

Preparation of N-[2-(3,4-difluorophenyl)ethyl]quinoxaline-2-carboxamide (417)

3,4-Difluorophenylacetic acid (5 g, 29 mmol) yielded 559 mg (46%) of 3,4-difluorophenylethylamine. 3,4-Difluorophenylethylamine (314 mg, 2 mmol), and 2-quinoxaloyl chloride (384 mg, 2 mmol) afforded 340 mg (54%) of 417:

rt=9.65 min.; m/z (rel. int.) 313 (M$^+$, 12), 256 (3), 186 (54), 157 (28), 140 (43), 129 (100), 102 (37), 75 (11).

Example 30

Preparation of N-[2-(3,5-difluorophenyl)ethyl]quinoxaline-2-carboxamide (418)

3,5-Difluorophenylacetic acid (5 g, 29 mmol) yielded 1.26 g (78%) of 3,5-difluorophenylethylamine. 3,5-Difluorophenylethylamine (314 mg, 2 mmol), and 2-quinoxaloyl chloride (384 mg, 2 mmol) afforded 298 mg (48%) of 418:

rt=9.84 min.; m/z (rel. int.) 313 (M$^+$, 27), 256 (3), 186 (63), 157 (33), 140 (9), 129 (100), 102 (31), 76 (11).

Example 31

Preparation of N-(trans-4-methylcyclohexyl)-6-methoxyquinoline-3-carboxamide (419)

6-Methoxyquinoline-3-carboxylic acid was prepared from p-anisidine using the methods of Erickson (J. Med. Chem., 1979, 22, 7, 816–823). A solution of 6-methoxyquinoline-3-carboxylic acid hydrochloride (500 mg, 2.09 mmol) in thionyl chloride (25 mL) was heated at reflux for 1 hour. After this time the excess thionyl chloride was removed by distillation and the remaining solid dried under vacuum. The solid was suspended in dichloromethane (25 mL) and treated with trans-4-methylcyclohexylamine hydrochloride (368 mg, 2.46 mmol), pyridine (5 mL), and triethylamine (0.345 mL). The reaction was stirred at ambient temperature overnight. After this time the reaction mixture was diluted with diethyl ether (200 mL) and the resulting organic solution washed with 1 N NaOH (3×50 mL) and then brine (1×). The organic solution was then dried over anhydrous MgSO$_4$, filtered, and concentrated to a solid. Chromatography of the crude product through a Biotage silica cartridge (8×4 cm i.d.) using a gradient of hexane to 50% ethyl acetate (in hexane) afforded 100 mg (16%) of 419:

rt=10.95 min.; m/z (rel. int.) 298 (M$^+$, 3), 202 (56), 186 (66), 158 (100), 143 (16), 116 (34), 101 (22), 88 (25), 77 (45), 55 (44), 41 (85).

In a similar manner, the following substituted quinoline-3-carboxamides were prepared:

Example 32

Preparation of N-(trans-4-methylcyclohexyl)-7-methoxyquinoline-3-carboxamide (420)

7-Methoxyquinoline-3-carboxylic acid hydrochloride (302 mg, 1.26 mmol) and trans-4-methylcyclohexylamine hydrochloride (188 mg, 1.26 mmol) afforded crude product. Chromatography of the crude product through a Biotage silica cartridge (8×4 cm i.d.) using a gradient of hexane to 50% ethyl acetate (in hexane) afforded 21 mg of semi-pure product. Recrystallization (2×) from hot toluene afforded 4 mg (1%) of 420:

rt=10.95 min.; m/z (rel. int.) 298 (M$^+$, 2), 202 (73), 186 (100), 158 (87), 143 (11), 131 (16), 116 (42), 101 (24), 88 (32), 77 (54), 55 (54), 41 (97).

Example 33

Preparation of N-(trans-4-methylcyclohexyl)-8-methoxyquinoline-3-carboxamide (421)

8-Methoxyquinoline-3-carboxylic acid hydrochloride (250 mg, 1.04 mmol), oxalyl chloride, and trans-4-methylcyclohexylamine hydrochloride (156 mg, 1.04 mmol) afforded crude product. Chromatography of the crude product through a Biotage silica cartridge (8×4 cm i.d.) using a gradient of hexane to 75% ethyl acetate (in hexane) afforded 52 mg (17%) of 421:

rt=10.95 min.; m/z (rel. int.) 298 (M$^+$, 100), 269 (24), 201 (63), 186 (91), 158 (48), 128 (39), 116 (12), 101 (11), 88 (5), 77 (7), 55 (5), 41 (8).

Example 34

Preparation of N-(trans-4-methylcyclohexyl)-5-fluoroquinoline-3-carboxamide (422) and N-(trans-4-methylcyclohexyl)-7-fluoroquinoline-3-carboxamide (423)

The methods of Erickson (J. Med. Chem., 1979, 22, 7, 816–823) were used to prepare a mixture of 5-fluoroquinoline-3-carboxylic acid hydrochloride and 7-fluoroquinoline-3-carboxylic acid hydrochloride from m-fluoroaniline. A mixture of these two acids (500 mg, 2.2 mmole) in dichloromethane (25 mL) was treated with a solution of oxalyl chloride in dichloromethane (1.2 mL of 2 M, 2.4 mmol) followed by dimethylformamide (5 drops). The reaction was stirred overnight, filtered (Gelman Acrodisc CR PTFE 0.45 micron) and concentrated to a solid. The solid was dissolved in dichloromethane (25 mL) and then treated with trans-4-methylcyclohexylamine hydrochloride (330 mg, 2.2 mmol) followed by 4-N,N'-dimethylaminopyridine (1.22 g, 10 mmol). The reaction was stirred 1 hour at ambient temperature. Chromatography of the crude reaction mixture through a Biotage silica cartridge (8×4 cm i.d.) using a gradient of hexane to 30% ethyl acetate (in hexane) afforded three fractions. Recrystallization of fraction A from hot heptane afforded 30 mg of N-(trans-4-methylcyclohexyl)-7-fluoro-quinoline-3-carboxamide (423):

rt=9.62 min.; m/z (rel. int.) 286 (M$^+$, 18), 191 (97), 174 (100), 146 (77), 126 (12), 119 (20), 99 (10), 81 (10).

Recrystallization of fraction C from hot heptane (2×) and heptane/dichloromethane (1×) afforded 8 mg of N-(trans-4-methylcyclohexyl)-5-fluoroquinoline-3-carboxamide (422):

rt=9.54 min.; m/z (rel. int.) 286 (M$^+$, 15), 191 (95), 174 (100), 146 (80), 126 (20), 119 (23), 99 (12), 81 (12).

Example 35

Preparation of N-(trans-4-methylcyclohexyl)-6-fluoroquinoline-3-carboxamide (424)

6-Fluoroquinoline-3-carboxylic acid hydrochloride (500 mg, 2.2 mmol), oxalyl chloride, and trans-4-methylcyclohexylamine hydrochloride (330 mg, 2.2 mmol) afforded crude product. Chromatography through a Biotage silica cartridge (8×4 cm i.d.) using a gradient of hexane to 40% ethyl acetate (in hexane) afforded 56 mg (9%) of 424:

rt=9.54 min.; m/z (rel. int.) 286 (M$^+$, 12), 191 (100), 174 (88), 146 (83), 126 (13), 119 (19), 99 (9), 81 (11).

Example 36

Preparation of N-(trans-4-methylcyclohexyl)-8-fluoroquinoline-3-carboxamide (425)

8-Fluoroquinoline-3-carboxylic acid hydrochloride (500 mg, 2.2 mmol), oxalyl chloride, and trans-4-methylcyclohexylamine hydrochloride (330 mg, 2.2 mmol) afforded crude product. Chromatography through a Biotage silica cartridge (8×4 cm i.d.) using a gradient of hexane to 40% ethyl acetate (in hexane) afforded 81 mg (13%) of 425:

rt=10.12 min.; m/z (rel. int.) 286 (M$^+$, 17), 191 (100), 174 (83), 146 (67), 126 (20), 119 (7), 99 (7), 81 (7).

Example 37

Preparation of N-(trans-4-methylcyclohexyl)-6,7-methylenedioxyquinoline-3-carboxamide (426)

Ethyl 4-chloro-6,7-methylenedioxyquinoline-3-carboxylate was prepared from 3,4-(methylenedioxy)aniline using the methods of Erickson (J. Med. Chem., 1979, 22, 7, 816–823).

Ethyl 4-chloro-6,7-methylenedioxyquinoline-3-carboxylate (18.5 g, 66.2 mmol) was dissolved in dioxane (100 mL) and treated with 50 mL 5 NNaOH and heated at reflux for 2 hour. After this time the solution was concentrated on a rotary evaporator, cooled and extracted with dichloromethane (2×100 mL). The remaining aqueous solution was then acidified with concentrated HCl and the precipitate collected and dried to afford 7 g of crude 4-hydroxy-6,7-methylenedioxyquinoline-3-carboxylic acid hydrochloride.

The crude acid (500 mg) was treated with thionyl chloride (20 mL) and heated at reflux for 1 hour. After this time the excess thionyl chloride was removed by distillation and the remaining solid pumped dry. The solid was dissolved in dichloromethane and treated with trans-4-methylcyclohexylamine hydrochloride (150 mg, 1 mmol), followed by triethylamine (0.3 mLs). The reaction was stirred 30 min and concentrated. The crude reaction mixture was partitioned between water (50 mL) and dichloromethane (4×25 mL). The combined dichloromethane extracts, were dried over anhydrous MgSO$_4$, filtered and concentrated to afford crude N-(trans-4-methylcyclohexyl)-4-chloro-6,7-methylenedioxyquinoline-3-carboxamide.

Without purification the amide was dissolved in hot toluene (25 mL) and diluted with ethanol (100 mL). p-Toluene sulfonic acid (400 mg) and 10% Pd on carbon (200 mg) were added and the reaction shook under 60 p.s.i. H$_2$, for 75 min at ambient temperature. The reaction was filtered, washing with ethanol and chloroform. The solvents were evaporated and the remaining solid dissolved in dichloromethane (50 mL) and equilibrated with 1 N NaOH. The organic layer was removed and the remaining aqueous phase extracted an additional two times with dichloromethane (2×50 mL). The combined organic washes were dried over anhydrous MgSO$_4$, filtered and concentrated to a solid (352 mg). Chromatography of this material through a Biotage silica cartridge (8×4 cm i.d.) using a gradient of hexane to 75% ethyl acetate (in hexane) afforded 147 mg (47% from trans-4-methylcyclohexylamine) of 426:

rt=11.50 min.; m/z (rel. int.) 312 (M$^+$, 16), 216 (79), 200 (100), 172 (60), 142 (10), 114 (19), 89 (10), 87 (10).

In a similar manner, the following substituted quinoline-3-carboxamides were prepared:

Example 38

Preparation of N-(trans-4-methylcyclohexyl)-6,7-ethylenedioxyquinoline-3-carboxamide (427)

Ethyl 4-chloro-6,7-ethylenedioxyquinoline-3-carboxylate was prepared using the methods of Erickson (J. Med. Chem., 1979, 22, 7, 816–823).

Hydrolysis of ethyl 4-chloro-6,7-ethylenedioxyquinoline-3-carboxylate (19.8 g, 66.2 mmol) afforded 13 g of crude 4-hydroxy-6,7-methylenedioxyquinoline-3-carboxylic acid hydrochloride.

The crude acid (500 mg), thionyl chloride, trans-4-methylcyclohexylamine hydrochloride (150 mg, 1 mmol), and triethylamine (0.3 mLs) afforded crude N-(trans-4-methylcyclohexyl)-4-chloro-6,7-ethylenedioxyquinoline-3-carboxamide.

Dehalogenation of the crude amide was accomplished in 1:1 ethanol-acetic acid (100 mL) with 10% Pd on carbon (200 mg) at 60 p.s.i. H$_2$ for 24 hours (ambient temperature). Workup and chromatography through a Biotage silica cartridge (8×4 cm i.d.) using a gradient of hexane to 60% ethyl acetate (in hexane) afforded 40 mg (12% from trans-4-methylcyclohexylamine) of 427:

rt=12.58 min.; m/z (rel. int.) 326 (M$^+$, 18), 230 (100), 214 (96), 186 (55), 131 (13), 103 (11), 75 (8), 55 (8) 41 (10).

Example 39

Preparation of N-(trans-4-methylcyclohexyl)-6,8-difluoroquinoline-3-carboxamide (428)

Ethyl 4-chloro-6,8-difluoroquinoline-3-carboxylate was prepared from 2,4-difluoroanilne (12.9 g, 100 mmol) using the methods of Erickson (J. Med. Chem., 1979, 22, 7, 816–823).

Hydrolysis of ethyl 4-chloro-6,8-difluoroquinoline-3-carboxylate afforded 10.5 g of crude 4-hydroxy-6,8-difluoroquinoline-3-carboxylic acid hydrochloride. The crude acid (2 g,), thionyl chloride, trans-4-methylcyclohexylamine hydrochloride (748 mg, 5 mmol), and triethylamine (0.3 mLs) afforded crude N-(trans-4-methylcyclohexyl)-4-chloro-6,8-difluoroquinoline-3-carboxamide.

Dehalogentaion of the crude amide was accomplished in 5:1 tetrahydrofuran-triethylamine (300 mL) with 10% Pd on carbon (2.25 g) at 60 p.s.i. $H_2$ for 4 hours (ambient temperature). Workup and chromatography through a Biotage silica cartridge (8×4 cm i.d.) using a gradient of hexane to 20% ethyl acetate (in hexane) afforded 150 mg (49% from trans-4-methylcyclohexylamine) of 428:

rt=9.66 min.; m/z (rel. int.) 304 ($M^+$, 14), 209 (100), 192 (84), 164 (76), 144 (22), 87 (7), 81 (12).

Example 40

Preparation of N-(trans-4-methylcyclohexyl)-5,7-difluoroquinoline-3-carboxamide (429)

Ethyl 4-chloro-5,7-difluoroquinoline-3-carboxylate was prepared from 3,5-difluoroanilne (12.9 g, 100 mmol) using the methods of Erickson (J. Med. Chem., 1979, 22, 7, 816–823).

Hydrolysis of ethyl 4-chloro-5,7-difluoroquinoline-3-carboxylate afforded 9.6 g of crude 4-hydroxy-6,8-difluoroquinoline-3-carboxylic acid hydrochloride.

The crude acid (500 mg,), thionyl chloride, trans-4-methylcyclohexylamine hydrochloride (250 mg, 1.67 mmol), and triethylamine (0.3 mLs) afforded crude N-(trans-4-methylcyclohexyl)-4-chloro-5,7-difluoroquinoline-3-carboxamide.

Dehalogentaion of the crude amide was accomplished in 4:1 tetrahydrofuran-triethylamine (75 mL) with 10% Pd on carbon (300 mg) under a $H_2$ balloon for 35 min (ambient temperature). Workup and chromatography through a Biotage silica cartridge (8×4 cm i.d.) using a gradient of hexane to 30% ethyl acetate (in hexane) afforded 134 mg (26% from trans-4-methylcyclohexylamine) of 429:

rt=9.23 min.; m/z (rel. int.) 304 ($M^+$, 14), 209 (94), 192 (100), 164 (65), 144 (18), 137 (14), 81 (16).

Example 41

Preparation of N-(trans-4-methylcyclohexyl)-6-methoxy-7-fluoroquinoline-3-carboxamide (430)

Ethyl 4-chloro-6-methoxy-7-fluoroquinoline-3-carboxylate was prepared from 3-fluoro-p-anisidine (14.1 g, 100 mmol) using the methods of Erickson (J. Med. Chem., 1979, 22, 7, 816–823).

Hydrolysis of ethyl 4-chloro-6-methoxy-7-fluoroquinoline-3-carboxylate afforded 13 g of crude 4-hydroxy-6-methoxy-7-fluoroquinoline-3-carboxylic acid hydrochloride.

The crude acid (1 g,), thionyl chloride, trans-4-methylcyclohexylamine hydrochloride (150 mg, 1 mmol), and triethylamine (0.3 mLs) afforded crude N-(trans-4-methylcyclohexyl)-4-chloro-6-methoxy-7-fluoroquinoline-13-carboxamide.

Dehalogentaion of the crude amide was accomplished in 1:1 tetrahydrofuran-dichloromethane (100 mL) with 10% Pd on carbon (300 mg) at 60 p.s.i. $H_2$ for 4 hours (ambient temperature). Workup and chromatography through a Biotage silica cartridge (8×4 cm i.d.) using a gradient of hexane to 40% ethyl acetate (in hexane) afforded 150 mg (47% from trans-4-methylcyclohexylamine) of 430:

rt=10.77 min.; m/z (rel. int.) 316 ($M^+$, 16), 221 (60), 220 (58), 204 (100), 176 (69), 161 (12), 133 (12), 101 (8), 81 (6), 55 (6), 41 (12).

In a similar manner, the following substituted quinoline-3-carboxamides were prepared:

Example 42

Preparation of N-(trans-4-methylcyclohexyl)-7-trifluoromethylquinoline-3-carboxamide (431)

4-Hydroxy-7-trifluoromethyl-3-carboxylic acid (514 mg, 2 mmol), thionyl chloride, trans-4-methylcyclohexylamine hydrochloride (225 mg, 1.5 mmol), and triethylamine (2 mL) afforded crude product. Chromatography through a Biotage silica cartridge (8×4 cm i.d.) using a gradient of hexane to 40% ethyl acetate (in hexane) afforded 514 mg (92%) of N-(trans-4-methylcyclohexyl)-4-chloro-7-trifluoromethylquinoline-3-carboxamide:

rt=9.74 min.; m/z (rel. int.) 370 ($M^+$, 8), 275 (100), 258 (80), 230 (42), 203 (13), 81 (23).

The amide (253 mg, 0.68 mmol) in 3:1 tetrahydrofuran-dichloromethane (75 mL) containing 10% Pd on carbon (150 mg) was hydrogenated at 40 p.s.i. $H_2$ for 10 min (ambient temperature). Filtration of the reaction mixture and chromatography through a Biotage silica cartridge (8×4 cm i.d.) using a gradient of hexane to 20% ethyl acetate (in hexane) afforded 40 mg (12%) of 431:

rt=9.38 min.; m/z (rel. int.) 336 ($M^+$, 13), 317 (3), 241 (100), 224 (85), 196 (90), 176 (12), 169 (23), 81 (17).

Example 43

Preparation of N-(trans-4-methylcyclohexyl)-6-trifluoromethylquinoline-3-carboxamide (432)

4-Hydroxy-6-trifluoromethyl-3-carboxylic acid (514 mg, 2 mmol), thionyl chloride, trans-4-methylcyclohexylamine hydrochloride (225 mg, 1.5 mmol), and triethylamine (2 mL) afforded crude N-(trans-4-methylcyclohexyl)-4-chloro-6-trifluoromethylquinoline-3-carboxamide:

m/z (rel. int.) 370 ($M^+$, 10), 351 (2), 335 (2), 275 (100), 258 (81), 230 (42), 203 (18), 97 (16), 81 (23).

The crude amide in 3:1 tetrahydrofuran-dichloromethane (100 mL) containing 10% Pd on carbon (250 mg) was hydrogenated at 20 p.s.i. $H_2$ for 4 hours (ambient temperature). Filtration of the reaction mixture and chromatography through a Biotage silica cartridge (8×4 cm i.d.) using a gradient of hexane to 30% ethyl acetate (in hexane) afforded 100 mg (20% from trans-4-methylcyclohexylamine) of 432:

rt=9.33 min.; m/z (rel. int.) 336 ($M^+$, 12), 317 (2), 241 (100), 224 (84), 196 (63), 176 (40), 169 (23), 81 (20).

Example 44

Preparation of N-(trans-4-methylcyclohexyl)-8-trifluoromethylquinoline-3-carboxamide (433)

4-Hydroxy-8-trifluoromethyl-3-carboxylic acid (514 mg, 2 mmol), thionyl chloride, trans-4-methylcyclohexylamine hydrochloride (225 mg, 1.5 mmol), and triethylamine (2 mL) afforded crude N-(trans-4-methylcyclohexyl)-4-chloro-8-trifluoromethylquinoline-3-carboxamide:

m/z (rel. int.) 370 (M+, 10), 351 (2), 335 (2), 275 (100), 258 (76), 230 (33), 210 (29), 203 (13), 81 (33).

The crude amide in 3:1 tetrahydrofuran-dichloromethane (100 mL) containing 10% Pd on carbon (250 mg) was hydrogenated at 20 p.s.i. $H_2$ for 15 min (ambient temperature). An additional quantity of Pd on carbon (250 mg) was added and the reaction hydrogenated at 20 p.s.i. $H_2$ for 15 min (ambient temperature). Filtration of the reaction mixture and chromatography through a Biotage silica cartridge (8×4 cm i.d.) using a gradient of hexane to 30% ethyl acetate (in hexane) afforded 35 mg (7% from trans-4-methylcyclohexylamine) of 433:

rt=9.83 min.; m/z (rel. int.) 336 (M+, 14), 317 (2), 241 (100), 224 (80), 196 (64), 176 (40), 169 (23), 81 (20).

Example 45

Preparation of N-(trans-4-methylcyclohexyl)-6-fluoroquinoxaline-2-carboxamide (434)

Synthesis of N-(4-fluoro-2-nitrophenyl)alanine Ethyl Ester.

Using the methods of Lumma (*J. Med. Chem.*, 1981, 24, 93–101), a suspension of DL-alanine ethyl ester hydrochloride (24.1 g, 157 mmol) in dichloromethane (200 mL) was treated with 16 mL of 10 N NaOH (160 mmol) and the mixture stirred 15 min. Anhydrous $MgSO_4$ was added and the mixture stirred until a thick paste formed. The dichloromethane was decanted from the aqueous paste and further dried over anhydrous $MgSO_4$. The organic solution was filtered, and concentrated to approximately 50 mL in volume. This was added to a solution of 2,5-difluoronitrobenzene (25 g, 157 mmol) in toluene (50 mL). The reaction was heated at reflux until the total volume was less than 50 mL. A reflux condenser was added to the reaction flask and the solution heated at reflux for 2 hours. After this time, triethylamine (22 mL, 158 mmol) was added and the reaction heated at reflux for an additional 1 hour. The reaction mixture was then cooled, diluted with chloroform and adsorbed on to silica. Chromatography through silica (20× 4.5 cm i.d.) using a gradient of hexane to ethyl acetate afforded 17.4 g (43%) of N-(4-fluoro-2-nitrophenyl)alanine ethyl ester:

rt=8.40 min; m/z (rel. int.) 256 (8, M+), 183 (100), 137 (21), 122 (12), 109 (14), 95 (10), 83 (9).

Synthesis of 7-fluoro-3-methyl-3,4-dihydro-2(1H)-ketoquinoxailne

Using the methods of Lumma (*J. Med. Chem.*, 1981, 24, 93–101), a solution of N-(4-fluoro-2-nitrophenyl)alanine ethyl ester (17.4 g, 67.9 mmol) in ethanol was treated with mossy tin (35 g, 295 mmol) followed by concentrated HCl (75 mL). As the vigorous reflux subsided, the reaction was heated to, and maintained at reflux and for 1 hour. The solution was decanted from the remaining tin and concentrated to afford 3.69 g of crude 7-fluoro-3-methyl-3,4-dihydro-2(1H)-ketoquinoxaline:

rt=8.18 min; m/z (rel. int.) 180 (M+, 29), 165 (42), 137 (100), 110 (17), 83 (15).

Synthesis of 7-fluoro-3-methyl-2(1H)-quinoxalinone

Using the methods of Lumma (*J. Med. Chem.*, 1981, 24, 93–101), the crude 7-fluoro-3-methyl-3,4-dihydro-2(1H)-ketoquinoxaline (3.69 g) in ethanol is (500 mL) was treated with 30% $H_2O_2$ (25 mL), and 1 N NaOH (50 mL) and the mixture heated at reflux overnight. After this time the reaction was cooled, acidified (pH ~3) with concentrated HCl, and the resulting solution extracted with chloroform (4×300 mL). The combined organic washes were dried over anhydrous $MgSO_4$, filtered, and concentrated to afford 3.2 g of crude 7-fluoro-3-methyl-2(1H)-quinoxalinone:

rt=8.42 min; m/z (rel. int.) 178 (M+, 45), 150 (71), 149 (100), 122 (12), 108 (18).

Synthesis of 2-chloro-3-methyl-7-fluoroquinoxaline

Without purification, 3.2 g of crude 7-fluoro-3-methyl-2 (1H)-quinoxalinone in phosphorous oxychloride (50 mL) was headed at 100° C. for 30 min, then poured over ice. The mixture was basified (pH ~10) with 10 N NaOH and the resulting solution extracted with chloroform (4×300 mL). The combined organic washes were dried over anhydrous $MgSO_4$, filtered, and concentrated to afford 6.47 g of crude 2-chloro-3-methyl-7-fluoroquinoxaline:

rt=6.23 min; m/z (rel. int.) 198 (M+, 13), 196 (M+, 40), 161 (100), 134 (12), 120(20), 100 (12).

Synthesis of 2-methyl-6-fluoroquinoxaline

Without purification, 6.47 g of crude 2-chloro-3-methyl-7-fluoroquinoxaline, in a mixture of chloroform (200 mL), methanol (50 mL), and triethylamine (200 mL), was treated with palladium on carbon (2 g, 10% Pd) and stirred under a balloon of hydrogen for 45 min at ambient temperature. After this time the reaction was filtered and concentrated. Chromatography through a Biotage silica cartridge (8×4 cm i.d.) using a gradient of hexane to 20% ethyl acetate (in hexane) afforded 2.03 g (18% from of N-(4-fluoro-2-nitrophenyl)alanine ethyl ester) of 2-methyl-6-fluoroquinoxaline rt=5.24 min; m/z (rel. int.) 162 (M+, 96), 135 (100), 94 (49).

Synthesis of 6-fluoroquinoxaline-2-carboxaldehyde

Using the method of Kepez (*Monatahefte fur Chemie*, 1989, 120, 127–130), a solution of 2-methyl-6-fluoroquinoxaline (225 mg 1.39 mmol) in ethyl acetate (30 mL) was treated with selenium dioxide (2.5 g) and the reaction mixture heated at reflux for 36 hours. The reaction was filtered hot and concentrated. Chromatography through a Biotage silica cartridge (8×4 cm i.d.) using a gradient of hexane to 10% ethyl acetate (in hexane) afforded 71 mg (29%) of 6-fluoroquinoxaline-2-carboxaldehyde.

rt=5.84 min; m/z (rel. int.) 176 (M+, 92), 148 (76), 121 (100), 100 (33), 94 (63), 75 (17).

Synthesis of 6-fluoroquinoxaline-2-carboxylic Acid

Using the method of Dodd (*Synthesis*, 1993, 295–297), a solution of 6-fluoroquinoxaline-2-carboxaldehyde (71 mg, 0.4 mmol) in formic acid (2 mL) was cooled in an ice bath and treated with hydrogen peroxide (2 mL of 30%). The reaction was stirred in the ice bath for 3 hours. After this time the reaction mixture was diluted with 10% HCl (25 mL) and extracted with dichloromethane (4×25 mL). The combined organic extracts were dried over anhydrous $MgSO_4$, filtered and concentrated to afford 35 mg (45%) of 6-fluoroquinoxaline-2-carboxylic acid.

N-(trans-4-methylcyclohexyl)-6-fluoroquinoxaline-2-carboxamide (434)

A solution of 6-fluoroquinoxaline-2-carboxylic acid (35 mg, 0.18 mmol) in dimethylformamide (4 mL) was treated with 1,1'-carbonyldiimidazole (29 mg, 0.18 mmol) and the reaction stirred for 16 hours at ambient temperature. After this time the reaction mixture was treated with trans-4-methylcyclohexylamine hydrochloride (27 mg, 0.18 mmol) and N,N-diisopropylethylamine (0.05 mL, 0.29 mmol) and the reaction stirred 2 hours at ambient temperature. The solvent was evaporated to a solid (700 mg). The solid was dissolved in chloroform (10 mL) and added to diethyl ether (30 mL) The organic solution was washed with water (1×25 mL) and brine. The remaining organic solution was dried over anhydrous MgSO$_4$, filtered, and concentrated to a solid (35 mg) HPLC (10 micron silica, 250×20 mm i.d.) of this material using a gradient of chloroform to 10% ethanol (in chloroform) afforded 20 mg (39%) of 434:

Rt=8.88 min; m/z (rel. int.) 287 (M$^+$, 23), 259 (1), 230 (9), 216 (3), 192 (22), 175 (36), 147 (100), 120 (28), 112 (47).

Example 46

Assay of mGluR Group I Antagonist Activity

HEK-293 cells expressing a recombinant receptor as described in WO 97/05252 were loaded with 2 μM Fura-2 acetoxymethylester by incubation for 30–40 minutes at 37° C. in SPF-PCB (126 mM NaCl, 5 mM KCl, 1 mM MgCl$_2$, 20 mM Na-HEPES, 1.0 mM CaCl$_2$, 1 mg/mL glucose, and 0.5% BSA, pH 7.4).

The cells were washed 1–2 times in SPF-PCB, resuspended to a density of 4–5 million cells/mL and kept at 37° C. in a plastic beaker. For recording fluorescent signals, the cells were diluted five-fold into a quartz cuvette with BSA-free 37° C. SPF-PCB to achieve a final BSA concentration of 0.1% (1.2 mL of 37° C. BSA-free SPF-PCB+0.3 mL cell suspension). Measurements of fluorescence were performed at 37° C. with constant stirring using a custom-built spectrofluorimeter (Biomedical Instrumentation Group, University of Pennsylvania). Excitation and emission wavelengths were 340 and 510 nm, respectively. To calibrate fluorescence signals, digitonin (Sigma Chemical Co., St. Louis, Mo.; catalog #D-5628; 50 μg/mL, final) was added to obtain maximal fluorescence ($F_{max}$), and the apparent minimal fluorescence ($F_{min}$) was determined by adding TRIS-Base/EGTA (10 mM, pH 8.3, final). Concentrations of intracellular Ca$^{2+}$ were calculated using a dissociation constant (Kd) of 224 nM and applying the equation:

$$[Ca^{2+}]_i = (F - F_{min}/F_{max}) \times Kd;$$

where F is fluorescence measured at any particular time of interest and F falls between $F_{max}$ and $F_{min}$.

Control responses to the addition of 5 mM Ca$^{2+}$ (final extracellular calcium concentration, 6 mM) were determined in separate cuvettes. Control responses to changes in extracellular calcium were determined throughout the length of the experiment. Compounds were tested at a single concentration per cuvette of cells, and all compounds were prepared in DMSO. Appropriate dilutions were made such that compounds were added in no greater volume than 10 μl per a total volume of 1500 μl (final DMSO not greater than 0.67%) to achieve any particular testing concentration.

Once a stable intracellular calcium baseline was achieved, the compound was added to the cuvette. The response or lack of response to the compound addition was allowed to stabilize for 1–3 minutes and then 5 mM calcium was added to determine the effect of the compound on the subsequent calcium response. Once the peak for the subsequent calcium response was obtained, digitonin and EGTA were added in a sequential manner to determine $F_{max}$ and $F_{min}$, respectively. Data were expressed as changes in intracellular calcium concentrations in nM. These changes in the calcium response post compound addition were compared to the control (no compound) calcium response. Responses to calcium in the presence of test compounds were normalized as a percent, change from that of controls. Data were entered into a Levenberg-Marquardt analysis for non-linear least squares and an IC$_{50}$ and 95% confidence intervals thereof were determined for each compound.

The invention thus has been disclosed broadly and illustrated in reference to representative embodiments described above. Those skilled in the art will recognize that various modifications can be made to the present invention without departing from the spirit and scope thereof.

What is claimed is:

1. A compound represented by the formula I,

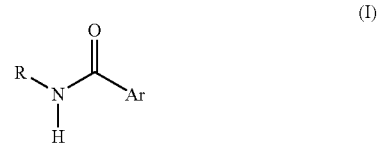

wherein R is an aralkyl, cycloalkyl, or alkylcycloalkyl group containing 5–12 carbon atoms that is optionally substituted with one or more substituents independently selected from the group consisting of F, Cl, OH, OMe, =O and —COOH;

wherein Ar is a quinoline moiety that is optionally substituted with at least one substituent selected from the group consisting of C$_1$–C$_6$-alkyl, F, Cl, Br, I, —OMe, —CF$_3$ and —O—(CH$_2$)$_n$—O—, wherein the oxygen radicals are bonded to adjacent positions on the quinoline ring and n is selected from the group consisting of 1 and 2, and wherein the amide carbonyl is attached at position 2–8 of the quinoline moiety or a pharmaceutically acceptable salt thereof.

2. The compound according to claim 1, wherein R is cycloalkyl.

3. The compound according to claim 2, wherein cycloalkyl is selected from optionally substituted cyclohexyl and optionally substituted adamantyl.

4. The compound according to claim 1, wherein R is selected from the group consisting of adamantyl, 2-adamantyl, (1S, 2S, 3S, 5R)-isopinocamphenyl, tricyclo[4.3.1.1(3, 8)]undec-3-yl, (1S, 2R,5S)-cis-myrtanyl, (1R,2R,4S)-isobornyl (1R,2R,3R,5S)-isopinocamphenyl, (1S, 2S,5S)-trans-myrtanyl, (1R,2R,5R)-trans-myrtanyl, (1R,2S,4S)-bornyl, 1-adamantanemethyl, 3-noradamantyl, (1S, 2S, 3S, 5R)-3-pinanemethyl, cyclooctyl, α,α-dimethylphenethyl, (S)-2-phenyl-1-propyl, cycloheptyl, 4-methyl-2-hexyl groups, 2,2,3,3,4,4,4-heptafluorobutyl, 4-ketoadamantyl, 3-phenyl-2-methylpropyl, 3,5-dimethyladamantyl, trans-2-phenylcyclopropyl, 2-methylcyclohexyl, 3,3,5-trimethylcyclohexyl, 2-(o-methoxyphenyl)ethyl, 2- (1,2,3,4-tetrahydronaphthyl), 4-phenylbutyl, 2-methyl-2-phenylbutyl, 2-(m-fluorophenyl)ethyl, 2-(p-fluorophenyl)ethyl, 2-(3-hydroxy-3-phenyl)propyl, (S)-2-hydroxy-2-phenylethyl, (R)-2-hydroxy-2-phenylethyl, 2-(3-m-chlorophenyl-2-methyl) propyl, 2-(3-p-chlorophenyl-2-methyl) propyl, 4-tert-butyl-cyclohexyl, (S)-1-(cyclohexyl)ethyl, 2-(3-(3,4-dimethylphenyl)-2-methyl)propyl, 3,3-dimethylbutyl, 2-(5-methyl)hexyl, 1-myrtanyl, 2-bornyl, 3-pinanemethyl, 2,2,3, 3,4,4,5,5-octafluoropentyl, p-fluoro-α,α-dimethylphenethyl, 2-naphthyl, 2-bornanyl, cyclohexylmethyl, 3-methylcyclohexyl, 4-methylcyclohexyl, 3,4-dimethylcyclohexyl, 5-chloro-tricyclo [2.2.1]heptyl, o-α,α-dimethylphenethyl, 2-indanyl, 2-spiro [4.5]decyl, 2-phenylethyl, 1-adamantylethyl, 1-(1-bicyclo[2.2.1]hept-2-yl)ethyl, 2-(2-methyl-2-phenylpropyl), 2-(o-fluorophenyl)ethyl, 1-(cyclohexyl)ethyl, and cyclohexyl.

5. The compound according to claim 1, wherein Ar has the formula:

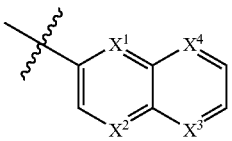

wherein one of $X^1$, $X^2$, $X^3$, and $X^4$ independently can be N or CH, provided that not more than one of $X^1$, $X^2$, $X^3$, and $X^4$ can be N.

6. The compound according to claim 5, wherein $X^1$ is N.
7. The compound according to claim 5, wherein $X^2$ is N.
8. The compound according to claim 5, wherein $X^3$ is N.
9. The compound according to claim 5, wherein $X^4$ is N.
10. A pharmaceutical composition comprising a compound according to claim 1, and a pharmaceutically acceptable diluent or excipient.
11. The compound according to claim 1, wherein said compound is selected from the group consisting of N-[6-(2-Methylquinolyl)]-1-adamantanecarboxamide, N-(6-Quinolyl)-1-adamantanecarboxamide, N-(2-Quinolyl)-1-adamantanecarboxamide, N-(3-Quinolyl)-1-adamantanecarboxamide, N-(1-Adamantyl)-3-quinoline-carboxamide, N-(1-Adamantyl)-2-quinolinecarboxamide, N-(1-Adamantyl)-6-quinolinecarboxamide, 1-Adamantyl-3-quinolinecarboxylate, and pharmaceutically acceptable salts thereof.
12. The compound according to claim 1, wherein said compound is selected from the group consisting of N-(1-Adamantyl)-3-quinolinecarboxamide, N-(1-Adamantyl)-2-quinolinecarboxamide, N-(1-Adamantyl)-6-quinolinecarboxamide, and pharmaceutically acceptable salts thereof.
13. The compound according to claim 1, wherein said compound is selected from the group consisting of N-[6-(2-Methylquinolyl)]-1-adamantanecarboxamide, N-(6-Quinolyl)-1-adamantanecarboxamide, N-(2-Quinolyl)-1-adamantanecarboxamide, and N-(3-Quinolyl)-1-adamantanecarboxamide, and pharmaceutically acceptable salts thereof.
14. The compound according to claim 1, wherein said compound is selected from the group consisting of N-(trans-4-Methylcyclohexyl)-2-quinolinecarboxamide, N-(trans-4-Methylcyclohexyl)-3-quinolinecarboxamide, and N-(trans-4-Methylcyclohexyl)-6-quinolinecarboxamide, and pharmaceutically acceptable salts thereof.
15. The compound according to claim 1, wherein said compound is selected from the group consisting of N-(1-Adamantyl)-7-trifluoromethylquinoline-3-carboxamide, Methyl N-(3-quinolyl)-3-carboxyadamantane-1-carboxamide and pharmaceutically acceptable salts thereof.
16. The compound according to claim 1, selected from the group consisting of N-(6-quinolinyl)-4-methylcyclohexane-1-carboxamide, N-(trans-4-methylcyclohexyl)-6-methoxyquinoline-3-carboxamide, N-(trans-4-methylcyclohexyl)-7-methoxyquinoline-3-carboxamide, N-(trans-4-methylcyclohexyl)-5-fluoroquinoline-3-carboxamide, N-(trans-4-methylcyclohexyl)-7-fluoroquinoline-3-car-boxamide, N-(trans-4-methylcyclohexyl)-6-fluoroquinoline-3-carboxamide, N-(trans-4-methylcyclohexyl)-8-fluoroquinoline-3-carboxamide, N-(trans-4-methylcyclohexyl)-6,7-methylenedioxyquinoline-3-carboxamide, N-(trans-4-methylcyclohexyl)-6,7-ethylenedioxyquinoline-3-carboxamide, N-(trans-4-methylcyclohexyl)-6,8-difluoroquinoline-3-carboxamide, N-(trans-4-methylcyclohexyl)-6-methoxy-7-fluoroquinoline-3-carboxamide, N-(trans-4-methylcyclohexyl)-7-trifluoromethylquinoline-3-carboxamide, N-(trans-4-methylcyclohexyl)-8-trifluoromethylquinoline-3-carboxamide and pharmaceutically acceptable salts thereof.

17. The compound according to claim 1, selected from the group consisting of N-(trans-4-methylcyclohexyl)quinoline-2-carboxamide, N-(trans-4-methylcyclohexyl)quinoline-3-carboxamide, and N-(trans-4-methylcyclohexyl)quinoline-6-carboxamide, and pharmaceutically acceptable salts thereof.

18. A compound having the structure

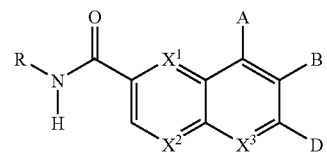

wherein $X^1$ and $X^2$ are selected from CH or N, $X^3$ is selected from N or C-E, wherein only one of $X^1$, $X^2$, and $X^3$ is N;

A, B, D, and E independently are selected from the group consisting of H, $C_{1-6}$-alkyl, OMe, F, Cl, Br, I, _and $CF_3$, or B and D together are —O—$(CH_2)$—O— or —O—$(CH_2)_2$—O—, R is selected from the group consisting of:

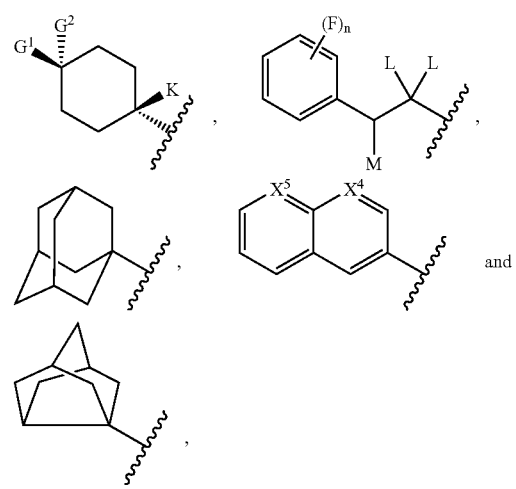

wherein

K is H or Me, $G^1$ is H, Me, or phenyl, $G^2$, K, L, and M independently are H or Me, n is 0, 1 or 2, and $X^4$ and $X^5$ independently are N or CH or a pharmaceutically acceptable salt thereof.

19. A compound according to claim 18, wherein R is

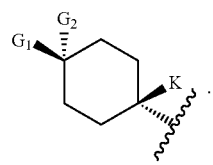

20. A method of making a compound according to claim 11, comprising reacting a compound of the formula R—NH$_2$ with a compound selected from the group consisting of Ar-(activated carboxylic acid group), ArC(O)OH, and salts thereof.

21. The method according to claim 20, wherein the compound of the formula R—NH$_2$ is reacted with Ar-(activated carboxylic acid group).

22. The method according to claim 21, wherein Ar-(activated carboxylic acid group) is a compound of the formula ArC(O)Cl.

23. The method according to claim 20, wherein said method is performed in the presence of a coupling reagent.

* * * * *